US009363996B2

(12) United States Patent
Goren et al.

(10) Patent No.: US 9,363,996 B2
(45) Date of Patent: Jun. 14, 2016

(54) COMPOSITIONS AND METHOD FOR BLOCKING ETHYLENE RESPONSE IN FIELD CROPS USING 3-(CY-CLOPROPYL-L-ENYL)-PROPANOIC SALT

(75) Inventors: Raphael Goren, Rechovot (IL); Moshe Huberman, Rechovot (IL); Eliezer Goldschmidt, Rehovot (IL); Joseph Riov, Petach Tikva (IL); Akiva Apelbaum, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 1127 days.

(21) Appl. No.: 13/144,638

(22) PCT Filed: Jan. 17, 2010

(86) PCT No.: PCT/IL2010/000043
§ 371 (c)(1),
(2), (4) Date: Oct. 31, 2011

(87) PCT Pub. No.: WO2010/082203
PCT Pub. Date: Jul. 22, 2010

(65) Prior Publication Data
US 2012/0040836 A1 Feb. 16, 2012

Related U.S. Application Data

(60) Provisional application No. 61/144,758, filed on Jan. 15, 2009.

(51) Int. Cl.
A01N 53/00 (2006.01)
A01G 1/00 (2006.01)
A01P 21/00 (2006.01)
A01N 37/06 (2006.01)
A23B 7/154 (2006.01)
A23B 9/26 (2006.01)

(52) U.S. Cl.
CPC ............... *A01N 37/06* (2013.01); *A23B 7/154* (2013.01); *A23B 9/26* (2013.01)

(58) Field of Classification Search
CPC ......... A01N 27/00; A01N 3/00; A01N 25/02; A01N 37/44; C07C 23/04; C07C 13/04
See application file for complete search history.

(56) References Cited

U.S. PATENT DOCUMENTS

2001/0019995 A1* 9/2001 Sisler ............................ 504/114
2004/0082480 A1* 4/2004 Daly et al. .................... 504/356
2007/0265166 A1* 11/2007 Bardella et al. ............... 504/357

FOREIGN PATENT DOCUMENTS

| CN | 101917841 | 12/2010 |
| EP | 1 856 976 A2 | 11/2007 |
| EP | 1856976 | 11/2007 |
| WO | WO 2009/002407 | 12/2008 |
| WO | WO 2009/002407 A1 | 12/2008 |
| WO | WO 2009/010981 | 1/2009 |
| WO | WO 2009/010981 A1 | 1/2009 |
| WO | WO 2010/082203 | 7/2010 |

OTHER PUBLICATIONS

Berge et al. Pharmaceutical Salts, Journal of Pharmaceutical Sciences, 1977, 66 (4), 1-19.*
International Preliminary Report on Patentability Dated Jul. 28, 2011 From the International Bureau of WIPO Re. Application No. PCT/IL2010/000043.
International Search Report and the Written Opinion Dated May 31, 2010 From the International Searching Authority Re. Application No. PCT/IL2010/000043.
Grichko "New Volatile and Water-Soluble Ethylene Antagonists", Russian Journal of Plant Physiology, XP019407768, 53(4): 523-529, Jul. 1, 2006. Introduction, p. 523, col. 2, Results, p. 524, col. 2-p. 527, col. 1, p. 525-526, Table 1, Compounds XI, XII, p. 527, Table 2, Compounds XI, XII, Discussion, p. 527, col. 1-p. 528, col. 1.
Grichko, V, "New Volatile and Water-Soluble Ethylene Antagonists", Russian Journal of Plant Physiology, 2006, vol. 53, No. 4, pp. 523-529.
Notice of Reason for Rejection Dated Jan. 7, 2014 From the Japanese Patent Office Re. Application No. 2011-545839 and Its Machine Translation in English.
Communication Pursuant to Article 94(3) EPC Dated Dec. 11, 2012 From the European Patent Office Re. Application No. 10709971.4.
Notification of Office Action Dated Mar. 5, 2013 From the State Intellectual Property Office of the People's Republic of China Re. Application No. 20108008642.6 and Its Translation Into English.
Conclusion on Patentability in the Invention Dated Jan. 30, 2013 From The Eurasian Patent Organization, The Eurasian Patent Office Re. Application No. 201190078 and Its Translation Into English.
Examination Report Dated May 14, 2012 From the Intellectual Property Office of New Zealand Re. Application No. 594072.
Communication Pursuant to Article 94(3) EPC Dated Feb. 12, 2015 From the European Patent Office Re. Application No. 10709971.4.

* cited by examiner

*Primary Examiner* — Johann R Richter
*Assistant Examiner* — Genevieve S Alley

(57) ABSTRACT

A method of inhibiting an ethylene response in a field crop is disclosed, comprising the step of applying to at least one portion of at least one plant of said field crop an amount of a solution of a water soluble cyclopropyl-1-enyl-propanoic acid salt (WS-CPD, Formula I) effective to produce inhibition of an ethylene response in said at least one plant, wherein M is chosen from the group consisting of Na, Li, K, and ½Ca.

9 Claims, 73 Drawing Sheets

| ACCUMULATION | 18 |
| --- | --- |
| RESOLUTION | 4 cm-1 |
| ZERO FILLING | ON |
| APODIZATION | COSINE |
| GAIN | 2 |
| SCANNING SPEED | 2mm/sec |
| DATE/TIME | 04/06/08 9:47 |
| OPERATOR | TAMILLA |
| FILE NAME | R-898 JWS |
| SAMPLE NAME | |
| COMMENT | KBr TABLET |

1: 3852.11, 100.0638       2: 3408.57, 82.2310       3: 3070.12, 81.6852
4: 2967.91, 56.3212        5: 2938.02, 81.6559       6: 2911.02, 62.9377
7: 2881.13, 59.2883        8: 2489.65, 105.0327      9: 1773.23, 80.2015
10: 1559.17, 2.8985        11: 1444.42, 24.5882      12: 1426.10, 18.3993
13: 1328.71, 66.0164       14: 1274.72, 89.2103      15: 1234.22, 78.3150
16: 1113.69, 100.2894      17: 1081.87, 95.6697      18: 1028.84, 61.7661
19: 994.12, 92.2720        20: 953.63, 81.4488

IR- SPECTRA

51107001/MI-018  PHYSICAL CHEMISTRY LAB
| METHOD | 00107 Na+ CONTENT IN SALT | 05/22/2008 9:30 |
|---|---|---|
| MEASURED | 05/22/2008 9:30 | |
| USER | TAMILLA | |
ALL RESULTS
| NO. | ID. | SAMPLE SIZE AND RESULTS | | |
|---|---|---|---|---|
| 1 | R-898 24.9 mg | 1.0 mL<br>R1=0.1828 mol/L<br>R2=1.821 mL | CONTENT<br>CONSUMPTION | |
24.9/134=0.1858
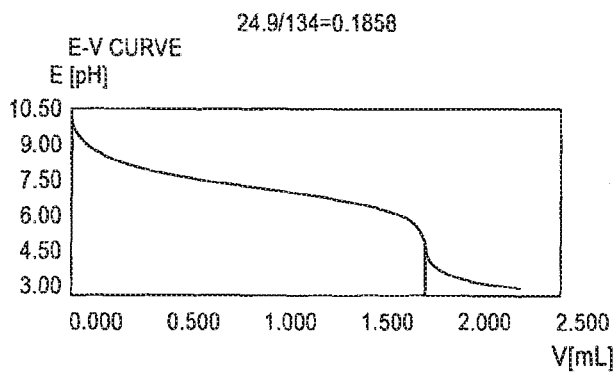
0.1828/0.1858=98.4%
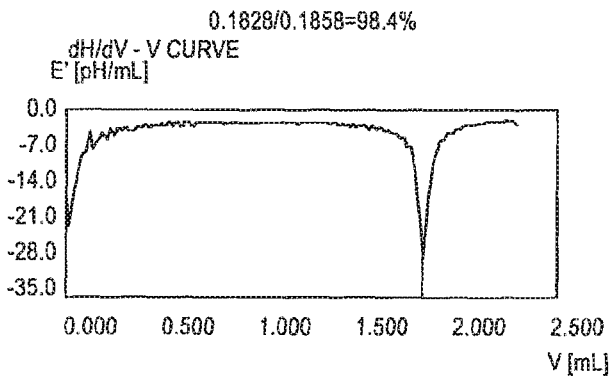
N.B. 536,18 POTENTIOMETRIC TITRATION OF SODIUM
Fig. 62

LICHRO 2 RIGHT-UV (OFFLINE)
SAMPLE ID: R-898 FREEZE
METHOD F:\LICHRO_2_R_UV\PROJECTS\BAPTA C12\METHOD\BAPTA C12 30 A MIN.MET
MOBILE PHASE: SOLVENT A (0.05%H3PO4 in 900ml H2O+0.5gr Amm ACETATE AND 100ml MeCN)
-SOLVENT B 0.05% H3PO4 IN MECN GRADIENT
FLOW 1ml/MIN DET.220nm
COLUMN: INERTSIL ODS 3V 250*4.6
DATA NAME: F:\L:CHRO_2_R_U\PROJECTS\BAPTA C12\DATA 04 2008\04.06.08 .03R898 F
INJ. VOLUME:10 μl
RUN TIME: 04/06/2008 11:28:56

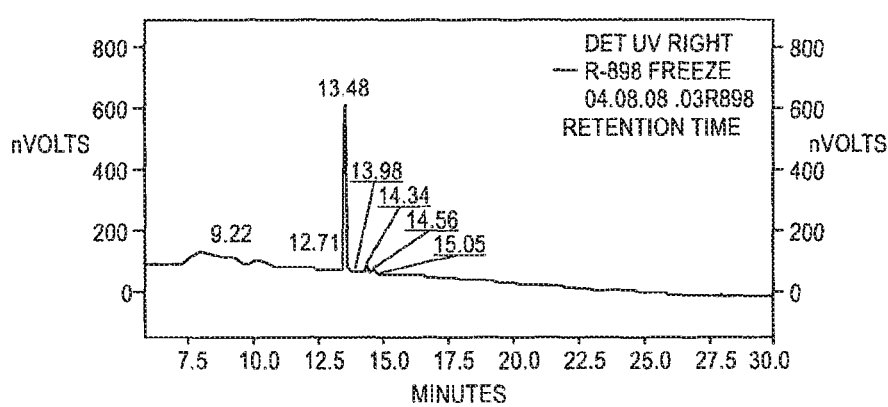

DET UV RIGHT RESULTS

| NAME | RETENTION TIME | AREA | AREA% | HEIGHT |
|---|---|---|---|---|
| | 9.22 | 34591 | 1.07 | 3938 |
| | 12.71 | 15622 | 0.48 | 3201 |
| | 13.48 | 2954232 | 91.16 | 545682 |
| | 13.98 | 5459 | 0.17 | 1191 |
| | 14.34 | 125907 | 3.89 | 25809 |
| | 14.56 | 87289 | 2.69 | 12620 |
| | 15.05 | 17440 | 0.54 | 12620 |
| | | | | 3399 |
| TOTALS | | 3240540 | 100.00 | 595840 |

$\triangle CU_2\text{-}CH_2\text{-}COONa$    HPLC ANALYSIS

FOR PROF. GOREN

Fig. 64

CERTIFICATE OF ANALYSIS

| Product Brand Name: | Agri-2 |
|---|---|
| Product Chemical Name: | 3-(1-Cyclopropenyl)propanoic acid, sodium salt |
| Manufacturer: | D-Pharm Ltd, Israel |
| Lot No.: | R-890 (lab. notebook 510. p.73) |
| Production Date: | 21-23 April, 2008 |
| Quantity: | 7 vials x 250mg each; 1 vial x 150mg |

| Name of Test | Test Results |
|---|---|
| Appearance: | White powder |
| Identification:<br>FT-IR<br>NMR<br>MS(ESI) | Spectra data correspond to the structure of the compound.<br>H-NMR spectral data corresp. to the structure of the compound.<br>MS(ESI): m/z 110.9 corresponds to $C_6H_7O_2$ |
| Chromatographic purity (HPLC): | 94.7% (RT: 13.36 min) |
| Sodium content: | 100.9% (potentiometric titration) |
| Main impurity: | 3.65% (RT 14.44 min) |

Store tightly closed at about (minus) -18°C. Allow to reach room temperature before opening.
Protect from light and humidity.
Transport is permitted at temperature of dry ice.
Test records: lab notebook 526. p.B3; lab notebook 536. p. 8
Date of analyses: April,2008
Next retest date: April,2009
Director, Chemical & Analytical R&D: Dr Israel Shapiro
Signature: *Shapiro*                                       Date: 28/04/2008

Fig. 66

COMPOSITIONS AND METHOD FOR BLOCKING ETHYLENE RESPONSE IN FIELD CROPS USING 3-(CY-CLOPROPYL-L-ENYL)-PROPANOIC SALT

RELATED APPLICATION

This application corresponds to PCT/IL2010/000043, filed Jan. 17, 2010, which claims the benefit under 35 USC 119(e) of U.S. Provisional Patent Application No. 61/144,758, filed Jan. 15, 2009, the disclosures of which are incorporated herein by reference in their entirety.

FIELD OF THE INVENTION

The present invention generally relates to water soluble compositions and methods of blocking ethylene responses in field crops, and particularly relates to methods of inhibiting various ethylene controlled vegetative, regenerative and reproductive processes in field crops by applying 3-cyclopropyl-1-enyl-propanoic sodium salt (WS-CPD).

BACKGROUND OF THE INVENTION

Ethylene is a volatile plant hormone that regulates a wide spectrum of plant growth processes. For example, it is involved in the control of the plant internal hormonal balance in such processes as blocking auxin transport and inducing the synthesis of abscisic acid (ABA). Ethylene is also involved in the control of various events in the life cycle of the plant, such as hastening fruit ripening, increasing enzyme activities, acceleration of aging and senescence, dormancy, inducing chlorophyll degradation, leaf and fruit abscission, epinasty, and other changes in vegetative growth orientation, as well as root growth and altering geotropic responses. Ethylene production in the plant is augmented by various forms of environmental stresses such as high temperature, chilling and freezing, drought and excessive water or flooding, radiation, mechanical stress, and attack by pathogens or insects. Since the early years of the $20^{th}$ century, ethylene has been used by growers to manipulate crops, both prior to and subsequent to harvesting. The need to control ethylene effects by either inhibiting ethylene action for such uses as prevention of pre-ripening fruit drop, decreasing fruit retention force, or applying for inducing leaf abscission in cotton as an aid to mechanical harvesting, extending fruit shelf life and the vase life of cut flowers, led scientists to attempt to develop on the one hand chemicals for blocking ethylene biosynthesis or action, and on the other hand to attempt to develop ethylene releasing chemicals. Ethephon™ is an example of an ethylene releasing chemical, commercially available by Rhône-Poulenc (hereinafter also 'ethephon'), while aminoethoxyvinylglycine (AVG) blocks ethylene biosynthesis and the volatile compound 1-methyl-cyclopropene (1-MCP) is an antagonist of ethylene action in plants. Although 1-MCP has become very popular during the last 15 years for postharvest handling for inhibiting fruit shelf life ripening and for delaying senescence of leafy vegetables and cut flowers, its major drawback is its volatility, which restricts its use to enclosed environments. Since 1-MCP is a very effective ethylene antagonist, a major thrust of the research conducted so far has been to develop non-volatile (and, as explained in detail below, preferably water-soluble), cyclopropene derivatives.

Application of ethylene, in the form of a gas or more often by means of ethylene releasing compounds, such as Ethephon™, is mainly used to thin fruitlets, to loosen ripe fruits for facilitation of mechanical harvesting, to cause plants to shed leaves for different purposes, to induce flowering, and to accelerate ripening (banana) or color break (citrus). Ethylene is also widely used to inhibit shoot growth. On the other hand, ethylene antagonists are also quite commonly used in agriculture. Examples of uses of ethylene antagonists are prevention of abscission of various plant organs, extension of the shelf life of flowers, fruits and vegetables, and blocking or delaying leaf senescence.

In various field crops, especially cereals, grain filling is mainly determined by the rate and duration of photosynthesis in the flag leaf and the various parts of the spikes in wheat and ears in maze. The contribution of the photoassimilatory parts of the spikes or ears alone to the final grain weight has been estimated to be approximately 25%. The main factor that limits the photoassimilate supply from the flag leaf and the green ear parts is senescence. Ethylene is one of the main factors that triggers the onset of senescence. Many field crops produce ethylene naturally, particularly under conditions of stress such as drought, to which agricultural crops are often subjected. It is has been reported that application of ethylene antagonists can increase grain yield in wheat. Presumably, this effectiveness arises from the ethylene antagonists ability to delay or retard senescence, thus extending the period of time of the plant photosynthetic activity. This property of ethylene antagonists is expected to be general for all field crops, since it affects metabolic processes common to all of them.

Solubility in water usually favors the penetration of applied chemicals into plant tissues. Many plant hormones as well as synthetic hormones and hormone antagonists are poorly water-soluble acids. For preparation of aqueous solutions of these chemicals it is necessary either to first dissolve them in an organic solvent or to keep the pH near or above 7. These practices, however, are not convenient for large scale applications. A common way to facilitate the use of the above chemicals is to convert them to a salt form, which readily dissolves in water. An example for this is the rooting hormone indole-3-acetic acid. For many years nurseries have been using it as a free acid mixed in talc powder, into which the bottom of the cuttings is dipped. The observation that dipping the bottom of the cuttings into a solution of the hormone is quite often more beneficial than dipping into the free acid led to the synthesis of the highly water soluble potassium salt of indole-3-butyric acid. This product is presently favored by many nurseries than the free acid. This and other observations have stimulated research and development of water soluble ethylene antagonists based on volatile cyclopropene derivatives.

Several publications, in particular those originating from Sisler's research group in the North Carolina University, have disclosed various approaches to the synthesis of cyclopropenyl alkanoic acids. See, for example, U.S. Pat. No. 6,365,549; *Tetrahedron* 1996, 52, 3409; *Tetrahedron* 1996, 52, 12509; and *Tetrahedron* 2004, 60, 1803. Of the methods therein disclosed, those that would be considered a priori to be most suitable for the synthesis of cyclopropenyl-propanoic acid have been found not to succeed. Therefore, new synthetic strategies for the production of cyclopropenyl-propanoic acid are needed.

Thus, an inhibitor of plant ethylene response that is usable in field crops, and which is a solid at room temperature, has long-term stability, and is highly water soluble remains a long felt need.

SUMMARY OF THE INVENTION

It is therefore an object of the present invention to disclose a method of inhibiting an ethylene response in a field crop, comprising the step of applying to at least one portion of at least one plant of said field crop an amount of a solution of a water soluble cyclopropyl-1-enyl-propanoic acid salt (WS-CPD, Formula I) effective to produce inhibition of an ethylene response in said at least one plant, wherein M is chosen from the group consisting of Na, Li, K, and ½Ca.

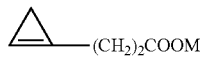

Formula I

It is a further object of this invention to disclose such a method, wherein M is sodium.

It is a further object of this invention to disclose such a method, wherein said solution is an aqueous solution.

It is a further object of this invention to disclose such a method, wherein said step of applying said solution further comprises the additional step of applying said solution according to a predetermined technique chosen from the group consisting of (a) contacting said at least one plant with said solution; (b) dipping at least part of said at least one plant in said solution; (c) spraying at least part of said at least one plant with said solution; (d) irrigating said at least one plant with said solution; (e) brushing at least part of said at least one plant with said solution; and (f) any combination of the above.

It is a further object of this invention to disclose such a method, wherein said ethylene response is selected from the group consisting of senescence, plant petiole abscission, and chlorophyll degradation.

It is a further object of this invention to disclose such a method, wherein said field crop is selected from the group consisting of cereals, legumes, oil-producing plants, fiber-producing plants, and tobacco.

It is a further object of this invention to disclose such a method, wherein said cereal is chosen from the group consisting of wheat, barley, rice, maize (corn), and oats.

It is a further object of this invention to disclose such a method, wherein said legume is chosen from the group consisting of soybeans, peas, peanuts, and beans.

It is a further object of this invention to disclose such a method, wherein said oil-producing plant is chosen from the group consisting of sunflower, safflower, castor plant, flax, sesame, perilla, and rape.

It is a further object of this invention to disclose such a method, wherein said fiber-producing plant is chosen from the group consisting of cotton and hemp.

It is a further object of this invention to disclose such a method, wherein said inhibition of an ethylene response is manifested by a difference chosen from the group consisting of (a) increase in the yield; (b) decrease in the rate of petiole abscission; (c) decrease in the rate of leaf chlorophyll content degradation; (d) delay in the senescence of the flag leaf; (e) delay in the senescence of the green organs of the spike and ears; and (f) any combination of the above, wherein said difference is measured relative to a plant in which said ethylene response is not inhibited.

It is a further object of this invention to disclose such a method, further comprising the additional step of adding an amount of a surfactant sufficient to produce a surface-active WS-CPD-containing aqueous solution.

It is a further object of this invention to disclose a method for delaying senescence in a field crop, comprising the step of applying to at least one portion of at least one plant of said field crop an amount of a solution of a water soluble cyclopropyl-1-enyl-propanoic acid salt (WS-CPD, Formula I) effective to prolong the life of said at least one plant, wherein M is chosen from the group consisting of Na, Li, K, and ½Ca.

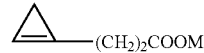

Formula I

It is a further object of this invention to disclose such a method, wherein M is sodium.

It is a further object of this invention to disclose such a method, wherein said solution is an aqueous solution.

It is a further object of this invention to disclose such a method, wherein said field crop is chosen from the group of leafy vegetables, spice-producing plants, and herbs.

It is a further object of this invention to disclose such a method, wherein said step of applying said solution further comprises the additional step of applying said solution according to a predetermined technique chosen from the group consisting of (a) contacting said at least one plant with said solution; (b) dipping at least part of said at least one plant in said solution; (c) spraying at least part of said at least one plant with said solution; (d) irrigating said at least one plant with said solution; (e) brushing at least part of said at least one plant with said solution; and (f) any combination of the above.

It is a further object of this invention to disclose such a method, wherein the field crop is selected from the group consisting of (a) Cereal and grain crops—Wheat, oats, barley, rye, rice, maize, grain sorghum; (b) Legumes for seeds—Peanut, field pea, cowpea, soybean, lima bean, mung bean, chickpea, pigeon pea, broad bean and lentil; (c) Forage crops—Grasses, legumes, crucifers, and other crops cultured and used for hay, pasture, fodder, silage or soilage; (d) Root crops—Sweet potato and cassava; (e) Fiber crops—Cotton, flax, ramie, kenaf and hemp; (f) Tuber crops—Potato; (g) Sugar crops—Sugarbeet, sugarcane; (h) Drug crops—Tobacco; and (i) Oil crops—Rapeseed/canola, sunflower, safflower, sesame, linseed, castor bean, and perilla.

It is a further object of this invention to disclose a method for increasing the yield of a field crop, comprising applying to at least part of at least one plant an amount of WS-CPD effective to prolong the life of the at least one plant, especially by reducing the senescence response to ethylene of the plant.

It is a further object of this invention to disclose a method for decreasing the rate of leaf abscission in a field crop, comprising applying to at least part of at least one plant an amount of WS-CPD effective to prolong the life of the at least one plant; especially by reducing the plant's leaf abscission response to ethylene.

It is a further object of this invention to disclose a method for delaying senescence of the "Flag leaf" and the green organs of the spike and ears which induces increase in grain yield in cereals (e.g., wheat, barley, maze or rice) comprising steps of applying to at least part of at least one plant an amount of WS-CPD effective to prolong the life of the at least one cereal.

It is a further object of this invention to disclose a method for delaying senescence of leafy vegetables (e.g., lettuce and baby lettuces, cabbage, spinach, or American celery) comprising steps of applying to at least part of at least one leafy vegetable an amount of WS-CPD effective to prolong the life of the at least one leafy vegetable.

It is a further object of this invention to disclose a method for delaying senescence of spice herbs comprising steps of applying to at least part of at least one herb an amount of WS-CPD effective to prolong the life of the at least one herb.

It is a further object of this invention to disclose a method for delaying senescence of cuttings comprising steps of applying to at least part of at least one plant an amount of WS-CPD effective to prolong the life of the at least one plant.

It is a further object of this invention to disclose method for decreasing the rate of leaf chlorophyll content degradation of a field crop, comprising applying to at least part of at least one plant an amount of WS-CPD effective to prolong the life of the at least one plant, especially by reducing the plant chlorophyll degradation response to ethylene.

It is a further object of this invention to disclose any of the above methods, wherein the applying step is carried out by a technique chosen from the group consisting of dipping, spraying, brushing, or irrigating at least part of the at least one plant in, on, or with an aqueous solution containing WS-CPD.

It is a further object of this invention to disclose such a method for inhibiting the ethylene response of a field crop, additionally comprising the step of admixing the WS-CPD with an amount of a surfactant sufficient to produce a surface-active WS-CPD-containing aqueous solution.

It is a further object of this invention to disclose a water-soluble cyclopropyl-1-enyl-propanoic acid sodium salt (WS-CPD) defined by formula I.

Formula I

It is a further object of this invention to disclose a water-soluble cyclopropyl-1-enyl-propanoic acid-sodium salt (WS-CPD) characterized by the following: (a) a $^1$H-NMR spectrum obtained in methanol solution that is characterized by the following peak positions ($\delta$ relative to TMS), splitting patterns, and integrations: 0.88 (s, 2H); 2.42 (t, 2H); 2.75 (t, 2H); and 6.52 (s, 1H); (b) a $^{13}$C{$^1$H}-NMR spectrum obtained in methanol solution that is characterized by the following peak positions ($\delta$ relative to TMS): 4.27, 23.58, 34.90, 97.21, 120.18, and 180.06; and (c) a $^{23}$Na{$^1$H}-NMR spectrum obtained in deuteromethanol solution that is characterized by a peak at $\delta$ −2.46 ppm.

It is a further object of this invention to disclose a water-soluble cyclopropyl-1-enyl-propanoic acid sodium salt (WS-CPD) characterized, when in the form of a powder, by an XRD pattern comprising at least one of the patterns chosen from the group containing (a) peaks at 2θ=10.6°, 15.94°, 28.42°, 47.3°, and 56.16°; (b) a broad peak centered at 2θ~23°.

It is a further object of this invention to disclose WS-CPD, in the form of an aqueous solution, adapted to be applied to at least a portion of a plant by means selected from the group consisting of dipping, brushing, spraying, irrigating, or any combination thereof.

It is a further object of this invention to disclose WS-CPD as defined above, wherein the WS-CPD is provided in the form of a surface-active aqueous solution.

BRIEF DESCRIPTION OF THE DRAWINGS

This invention will now be described in more detail, by presenting examples, with references to the accompanying drawings:

FIG. 62 Potentiometric titration of sodium CPD;

FIG. 64 The HPLC analysis of WS-CPD; and

FIG. 66 The analysis statement of WS-CPD;

DETAILED DESCRIPTION OF THE INVENTION

Figure 1:
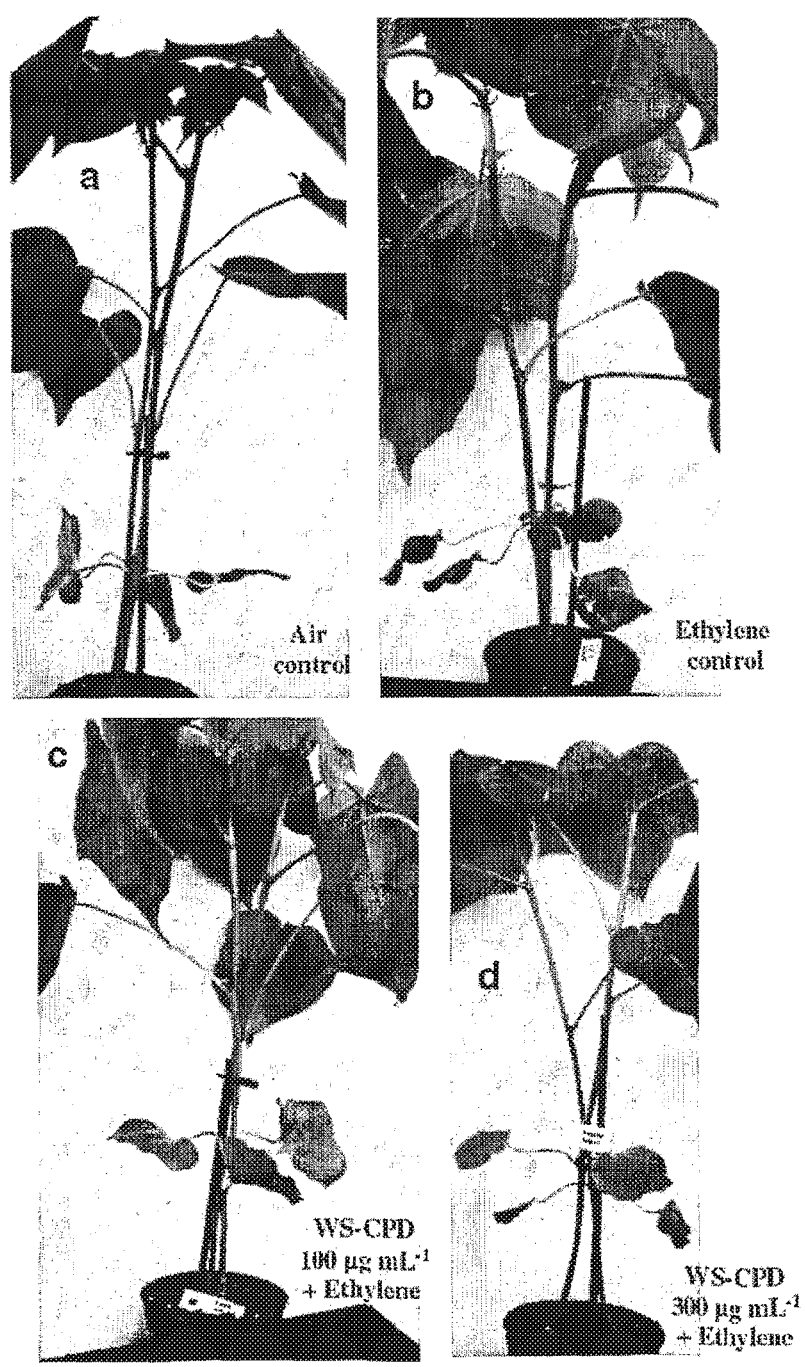
FIG. 1 Effect of pretreatment with WS-CPD spraying on ethylene (10 μL L$^{-1}$)-induced leaf epinasty of young cotton seedlings.

The present invention discloses means and method to provide WS-CPD: an inhibitor of plant ethylene response that is usable in field crops, and which is a solid at room temperature, has long-term stability, and is highly water soluble.

WS-CPD which is used to carry out the present invention is defined by Formula I:

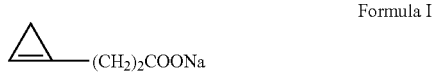

Formula I

The term "field crops" refers hereinafter is a generic term and includes all agricultural crops extensively grown except fruits, vegetables and flowers (that are defined as horticultural crops), and their agronomic classification. More specifically, and in a non-limiting manner, the term refers to (a) Cereal and grain crops—Wheat, oats, barley, rye, rice, maize, grain sorghum; (b) Legumes for seeds—Peanut, field pea, cowpea, soybean, lima bean, mung bean chick pea, pigeon pea, broad bean and lentil; (c) Forage crops—Grasses, legumes, crucifers, and other crops cultured and used for hay, pasture, fodder, silage or soilage; (d) Root crops—Sweet potato and cassava; (e) Fiber crops—Cotton, flax, ramie, kenaf and hemp (f) Tuber crops—Potato; (g) Sugar crops—Sugarbeet, sugarcane; (h) Drug crops—Tobacco; and (i) Oil crops—Rapeseed/canola, sunflower, safflower, sesame, linseed, castor bean, and perilla.

The term 'aqueous solution' refers hereinafter to water. The above definition notwithstanding, the WS-CPD is provided in various embodiments in the form of a powder, a tablet, an aerosol, an emulsion, a suspension, a water-miscible solution or in any other form that can be adapted for application of the WS-CPD to field crops.

Plant Models

The experimental models comprise (1) selection of sensitive and agriculturally important plants, and (2) standard physiological systems that represent the "generality", responses to plant hormone.

The plants chosen as representative examples for the model studies were cotton (*Gossyium hirsutum* barbadense L.); tobacco (*Nicotiana tabacum* var. 'Samsun'); and wheat (*Triticum turgidum* var. 'Gdera').

Four standard physiological systems were chosen for the model studies:

(1) Abscission—This is a very sensitive model system for studying the effects of plant hormones. Ethylene induces the process of abscission, while auxin delays it. In the laboratory the experimental system is based on plant organ explants, which include the abscission zone. Abscission is induced by exposure to ethylene and at the termination of the experiment the number of abscised organs, usually either leaf blades or petioles are counted and the fraction of abscission is calculated. In the case of fruit, the decrease in fruit retention force is analyzed. In cotton, when WS-CPD (the ethylene-action antagonist herein disclosed) is tested, the whole plants or explants are pretreated by spraying with the antagonist, dissolved in a phosphate buffer solution (10-20 mM, pH 7.0) including 0.1% commercially available Kinetic™ as surfactant, and left to incubate for a predetermined time, usually between 6 and 24 h. The plants or explants are then further exposed for 24 h to ethylene gas (5 to 20 µL L$^{-1}$). The plants or explants are then ventilated and incubated for the required time under controlled conditions. At the end of the experiment the percentage of abscission is determined.

(2) Chlorophyll degradation—This is a standard model for studying senescence. Plant material (whole plants, excised leaves or leaf discs) are pretreated. In cotton, tobacco and wheat, when WS-CPD is tested, the whole plants or explants are pretreated by spraying with the antagonist, dissolved in phosphate buffer solution (10-20 mM, pH 7.0) including 0.1% commercially available Kinetic™ surfactant, and left to incubate for a predetermined time, usually between 6 and 241. The plants or explants are then further exposed for 24 h to ethylene gas (1 to 100 µL L$^{-1}$), or sprayed with Ethephon™ (wheat; 250 to 750 µL L$^{-1}$). The plants or explants are then ventilated and incubated for the required time under controlled conditions. At the end of the experiment a dimethylsulfoxide (DMSO) extract of the plant tissue is prepared, and the chlorophyll content of the extract is determined by spectrophotometric analysis. The chlorophyll content is reported either on a fresh, dry weight basis, or on a surface area basis.

(3) Epinasty—This is also one of the classical methods for studying ethylene effects in plants. The extent of ethylene-induced epinasty of leaves is determined by measuring the change of the angle between the petiole and the stem shoot or blade. After exposure of the intact plant to ethylene, the upright grown leaves bend downward. The increase in the angle values (degrees) between petiole and the stem is used as a measure of the effect of the ethylene. When WS-CPD is tested on cotton and wheat plants, the whole plants are pretreated by spraying with the antagonist dissolved in phosphate buffer solution (10-20 mM, pH 7.6) including 0.1% Kinetic™ as surfactant, and left to incubate for a predetermined time, usually between 6 and 24 h. The plants are then further exposed for 24 h to ethylene gas (cotton, 5 to 10 µL L$^{-1}$), or sprayed with Ethephon™ (wheat, 250 to 750 µL L$^{-1}$). The plants are then ventilated and incubated for the required time under controlled conditions. The epinastic effect is expressed by measuring the degree values of the downward curvature between the blade and petiole (cotton, FIGS. 1-3) or between the blade and the stem (wheat, FIGS. 31 and 32).

(4) Wheat Grain yield—This is a common test of the effects of exposure of monocot plants either to environmental stresses such as drought that induce senescence by increasing endogenous ethylene production. Excessive internal or external ethylene will accelerate senescence which will lead to reduced grain yield. In this project the intact plants were grown in the greenhouse up to the spike hading at milky stage I and II. The plants were then sprayed with the dissolved WS-CPD in phosphate buffer solution (10 mM, pH 7.6) including 0.1% Kinetic™ as surfactant.

Young Cotton Seedlings

Figure 2:
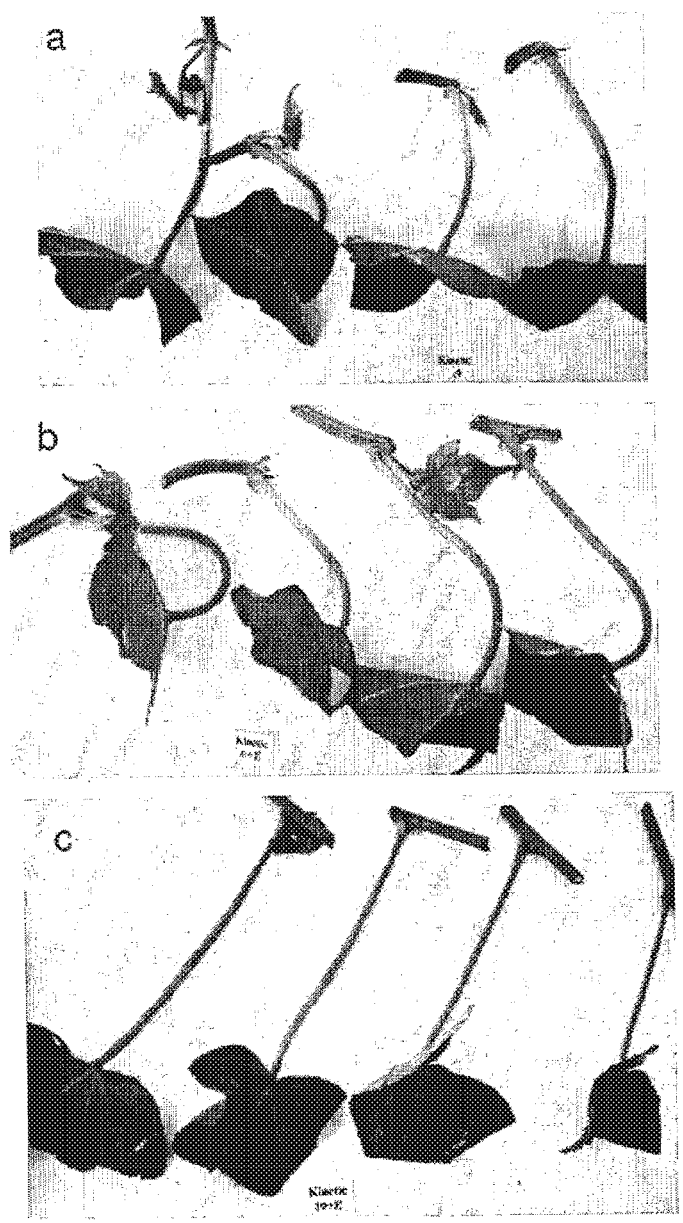
FIG. 2 Effect of pretreatment with WS-CPD spraying on ethylene (10 μL L$^{-1}$)-induced leaf epinasty of young cotton seedlings.
Figure 3:
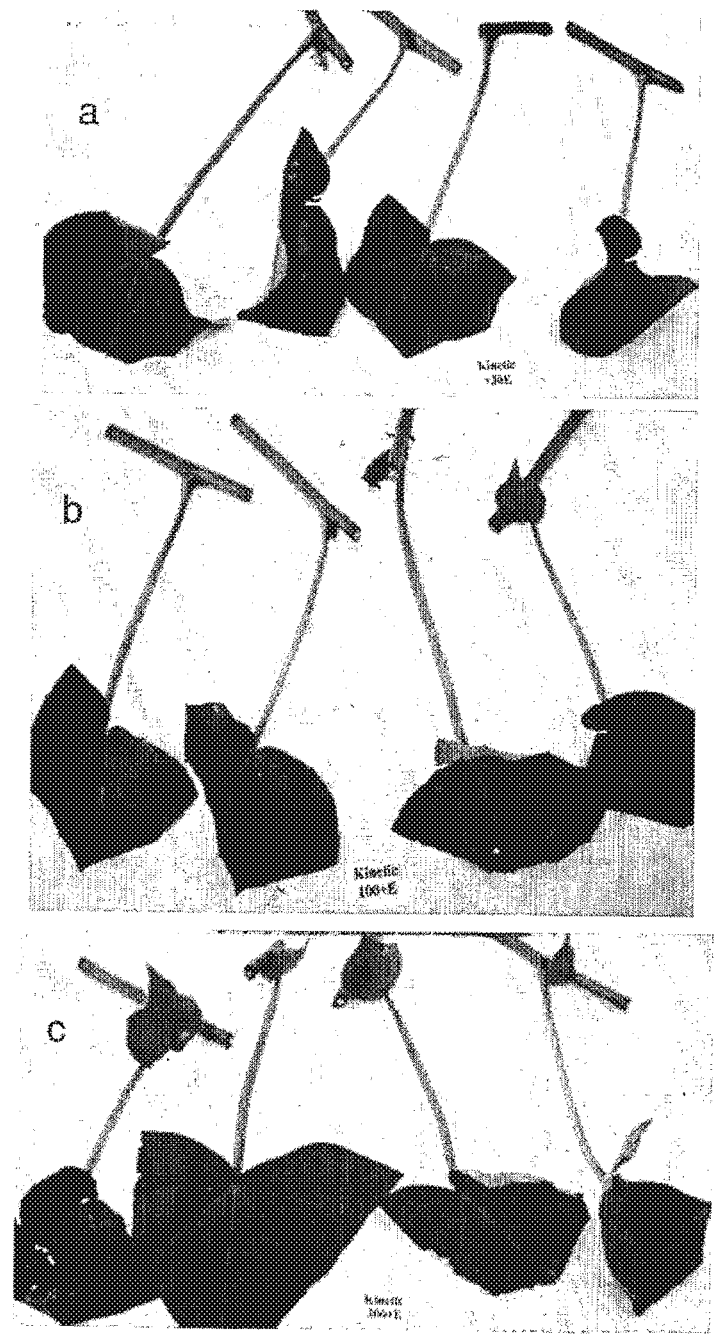
FIG. 3 Effect of pretreatment with WS-CPD spraying on ethylene (10 μL L$^{-1}$)-induced leaf epinasty of young cotton seedlings.
Figure 4:
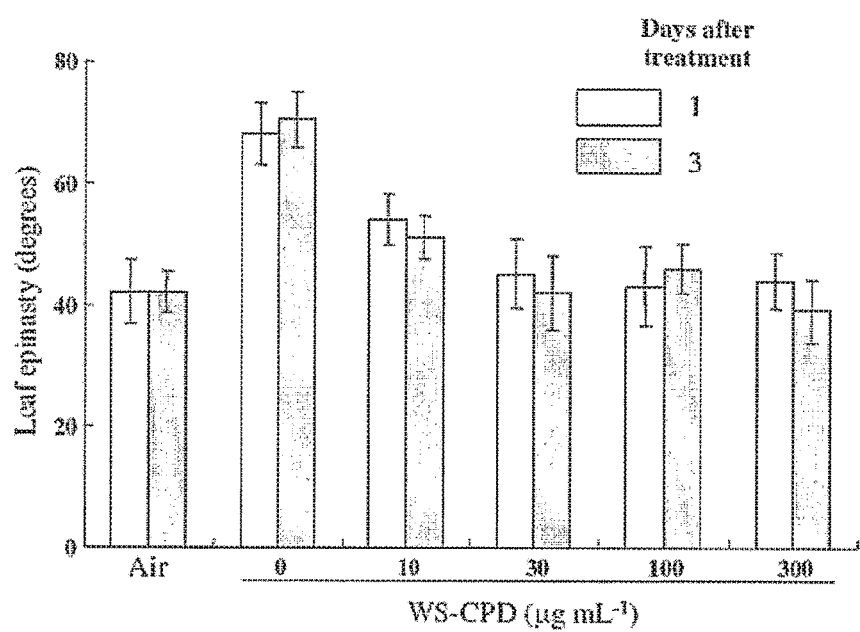
FIG. 4 Effect of pretreatment with WS-CPD spraying on ethylene (10 μL L$^{-1}$)-induced leaf epinasty of young cotton seedlings, expressed by the angle (degrees) between the petiole and the blade.

Epinasty—Three-week-old seedlings (FIGS. 1 to 3) were sprayed with WS-CPD (10 to 300 µg mL$^{-1}$). After 24 h, the seedlings were transferred to a closed system (85% humidity, 22° C., regular fluorescent light) and exposed to 10 μL L$^{-1}$ of ethylene gas for an additional 24 h. At the end of this treatment the seedlings were exposed to air for an additional 24 h. A close-up demonstration of the ethylene effect on petiole epinasty and the complete antagonistic effect of WS-CPD is depicted in FIG. 2. WS-CPD completely antagonized the ethylene-induced epinasty, which in the ethylene-treated seedlings lasted throughout the experimental period. It is evident that even 10 and 30 μg mL$^{-1}$ of WS-CPD (FIGS. 2 and 4, respectively) completely reversed the ethylene-induced leaf epinasty.

Figure 5:
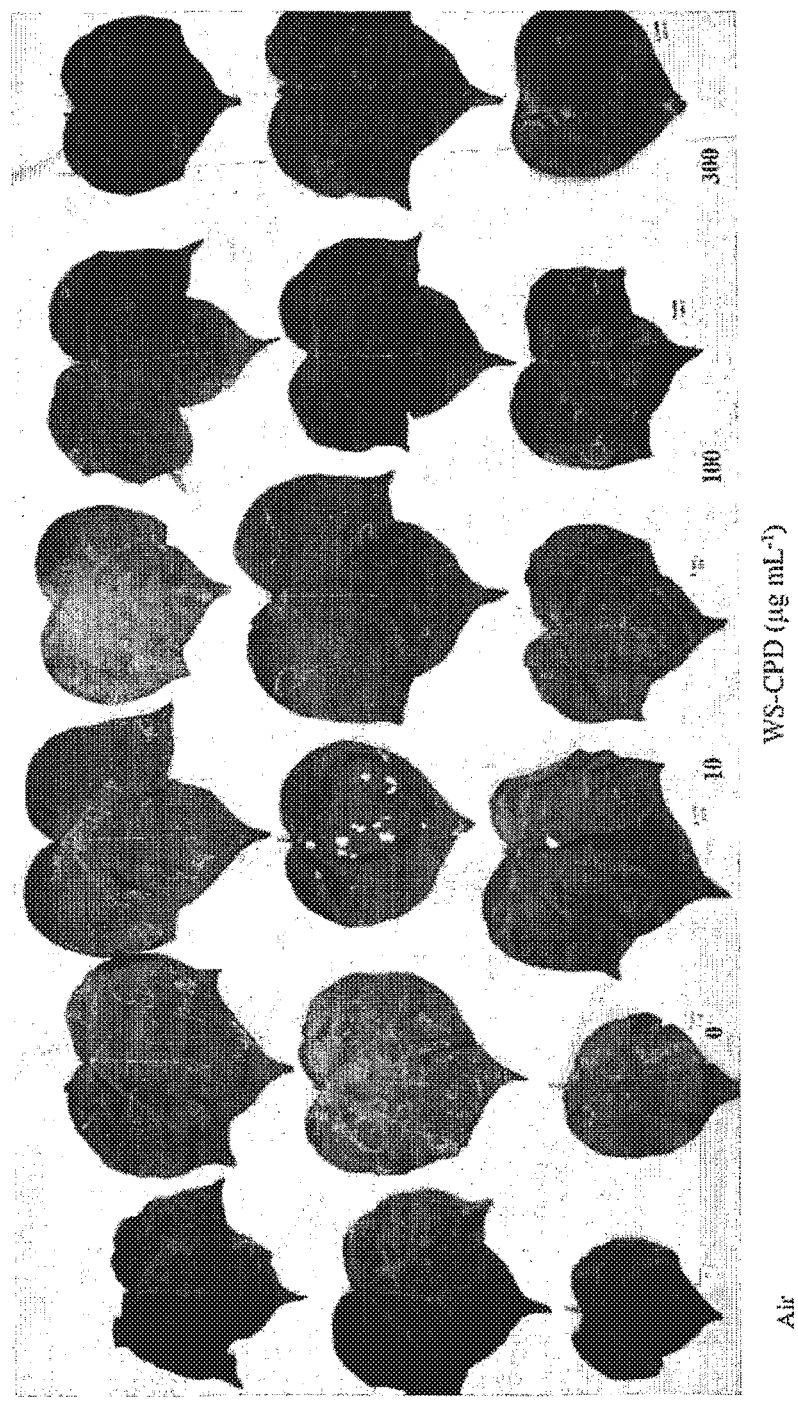
FIG. 5 Effect of pretreatment with WS-CPD spraying on ethylene (10 μL L$^{-1}$)-induced leaf senescence of young cotton seedlings.
Figure 6:
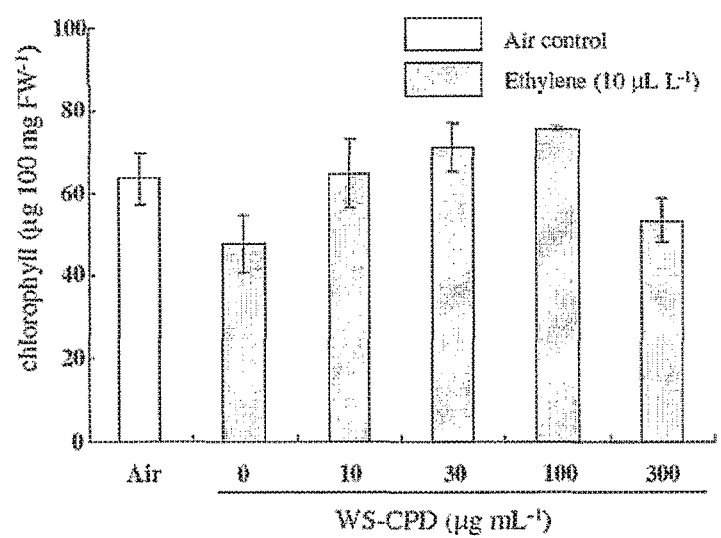
FIG. 6 Effect of pretreatment with WS-CPD spraying on ethylene (10 μL L$^{-1}$)-induced reduction in chlorophyll content in blades of young cotton seedlings.

Chlorophyll degradation—Three-week-old seedlings were pretreated by spraying with 10 to 300 μg mL$^{-1}$ WS-CPD. After 24 h leaf explants were prepared (FIGS. 2 and 3) and exposed to ethylene (10 μL L$^{-1}$) for additional 24 h in a closed environment (85% humidity, 22° C., regular fluorescent light). Pretreatment with 10 μg mL$^{-1}$ WS-CPD completely antagonized ethylene-induced chlorophyll degradation. The content of chlorophyll in the leaf blades of the treated plants remained the same as in the untreated control (FIGS. 5 and 6). Pretreatment with 30 and 100 μg L$^{-1}$ even increased the content of chlorophyll by 20 and 28%, respectively, as compared with the untreated control (FIG. 6). Higher concentrations of WS-CPD were less effective.

Figure 7:
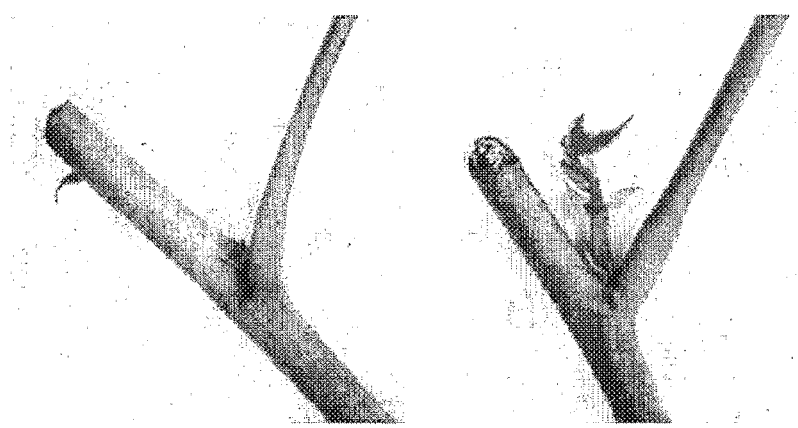
FIG. 7 Abscission model (explants) for studying leaf abscission of young cotton plants.
Figure 8:
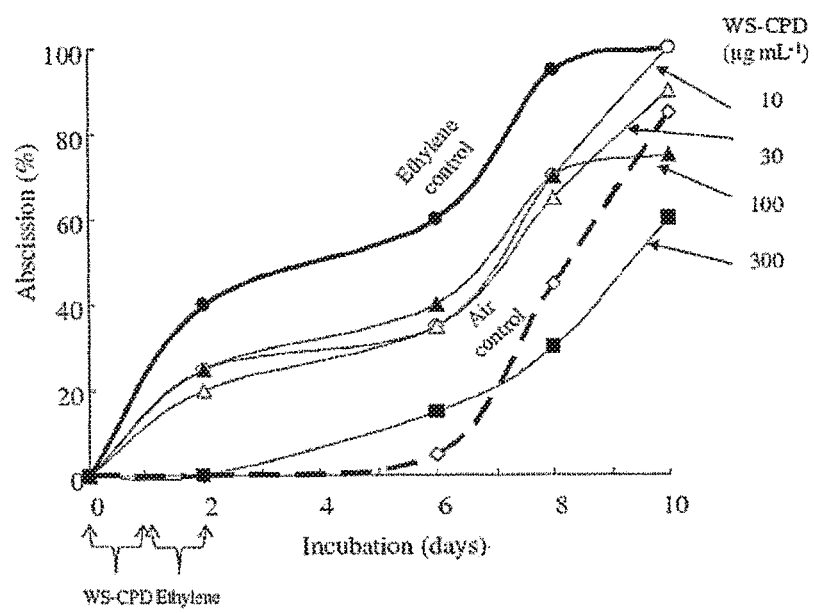
FIG. 8 Effect of pretreatment with WS-CPD spraying on ethylene (10 μL L$^{-1}$)-induced abscission of young cotton leaf explants.

Petiole abscission—Three-week-old intact seedlings were treated as described above with WS-CPD (10 to 300 μg mL$^{-1}$). At the termination of the standard treatment procedure, explants in which the abscission zone is located between the stem and the petiole (FIG. 7), were incubated in a closed environment (85% humidity, 22° C., regular fluorescent light). As expected, ethylene accelerated the rate of petiole abscission. WS-CPD, at 10 to 30 μg mL$^{-1}$, decreased abscission by about 20% throughout the experiment, while the abscission percentage of explants treated with 300 μg mL$^{-1}$ of WS-CPD was lower than the air control treatment.

Mature Cotton Plants

Figure 9:
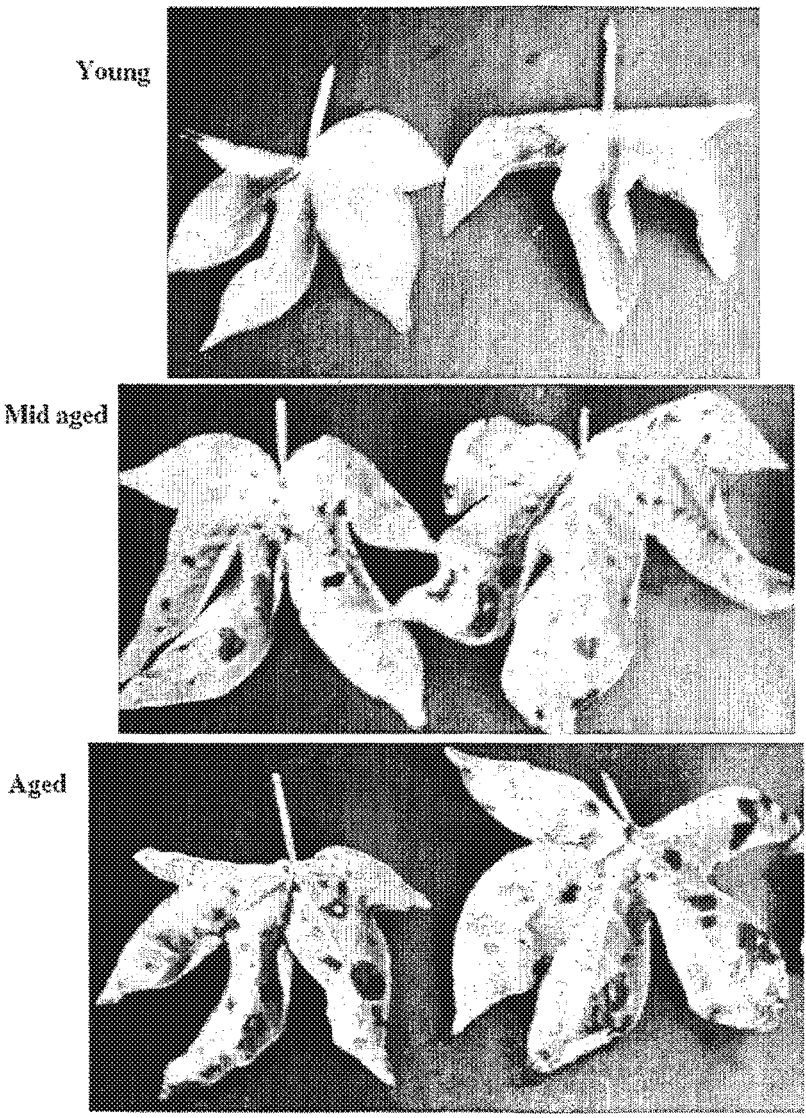
FIG. 9 Ethylene (10 μL L$^{-1}$)-induced senescence of excised cotton leaves at different developmental stages.
Figure 10:
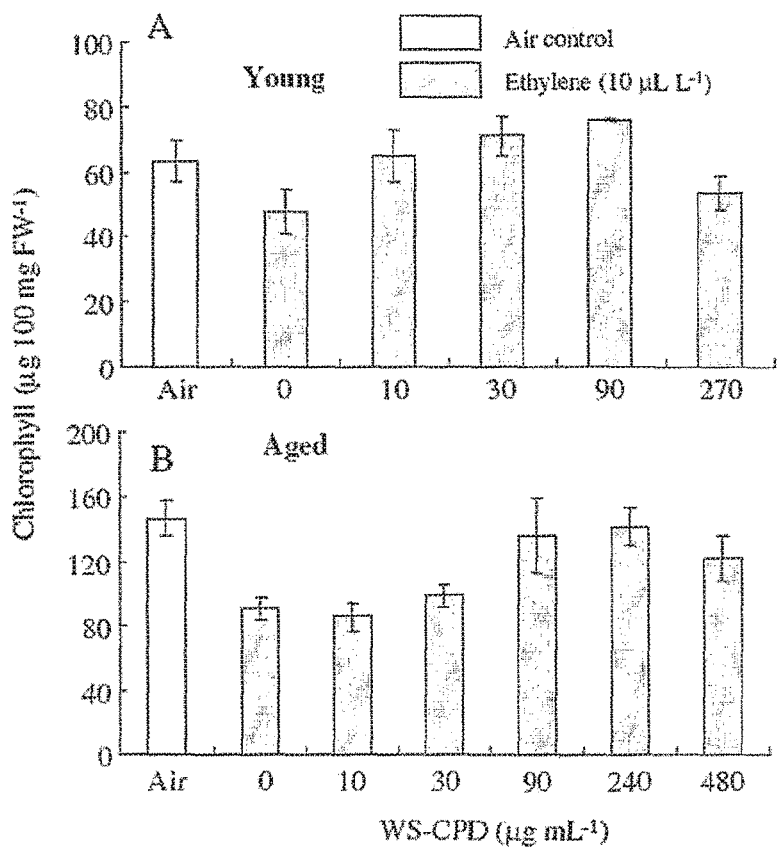
FIG. 10 Effect of pretreatment with WS-CPD spraying on ethylene (10 μL L$^{-1}$)-induced reduction in chlorophyll content of excised cotton leaves at different developmental stages.

Chlorophyll degradation—Shoots (6-month-old) with young, young-mature and mature leaves were harvested from mature plants, grown in a nearby field and processed as described above. Ten μg mL$^{-1}$ WS-CPD completely antagonized the ethylene-induced chlorophyll degradation (FIG. 9*a*) in young leaves, while higher concentrations (270 μg mL$^{-1}$) were less effective (FIG. 10*a*). Mature leaves (FIG. 9*c*) were less sensitive to the antagonizing effect of WS-CPD; higher concentrations of WS-CPD (90 and 240 μg mL$^{-1}$) were required in order to obtain 95% inhibition of ethylene-induced chlorophyll degradation. Higher concentrations (e.g. 480 μg L$^{-1}$) were less effective (FIG. 10*b*).

Figure 11:
FIG. 11 Abscission model (explants) for studying abscission of aged cotton plants.
Figure 12:
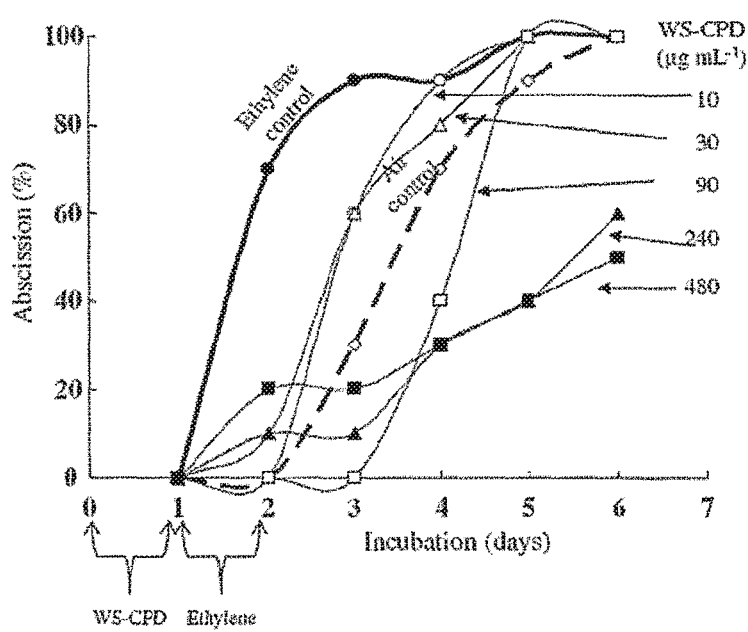
FIG. 12 Effect of pretreatment with WS-CPD spraying on ethylene (10 μL L$^{-1}$)-induced abscission of mature cotton leaf explants.

Petiole Abscission—Shoots (6-month-old) obtained as described above (for the chlorophyll degradation measurements) were sprayed with 10 to 480 μg mL$^{-1}$ of WS-CPD, and further exposed to 10 μL L$^{-1}$ ethylene. Leaf explants prepared from these shoots (FIG. 11) were incubated in a closed environment (85% humidity, 22° C., regular fluorescent light). Doses of 10 and 30 μg mL$^{-1}$ of the inhibitor decreased abscission by 20% after 3 days of incubation. Abscission percentage, following treatment with 90 μg mL$^{-1}$ WS-CPD was slightly lower than that of the untreated air control. However, all explants that were treated with three concentrations (10, 30 and 90 μg mL$^{-1}$) of WS-CPD reached 100% abscission on day 5, while explants treated with higher concentrations (240-480 μg mL$^{-1}$) reached only 50% abscission in the same period of time (FIG. 12).

Young Tobacco Seedlings (6 Weeks after Germination)

Figure 13:
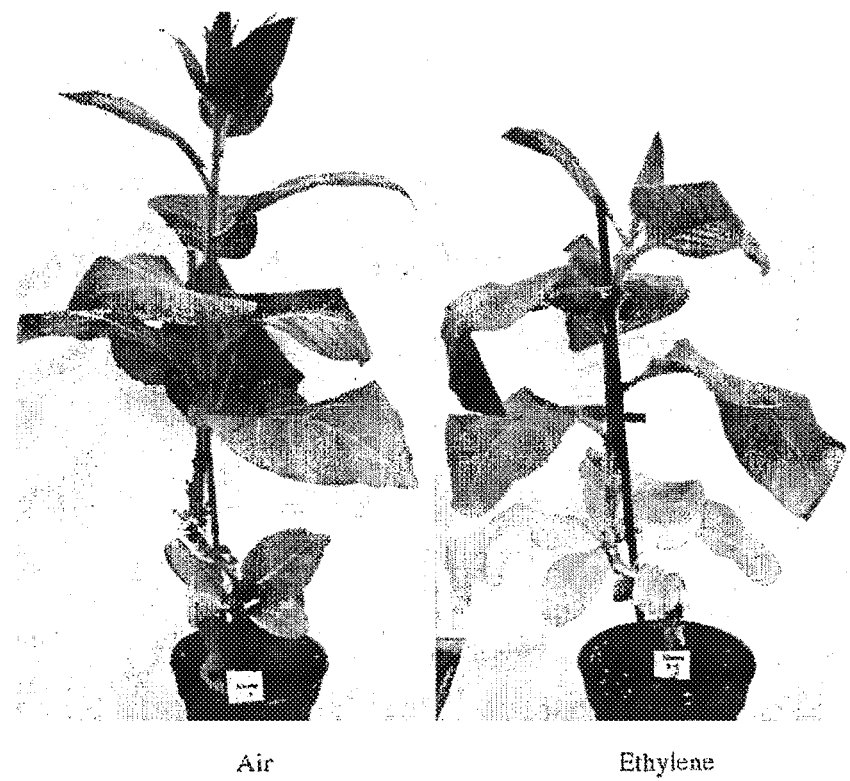
FIG. 13 Ethylene (10 μL L$^{-1}$)-induced senescence of tobacco leaves.
Figure 14:
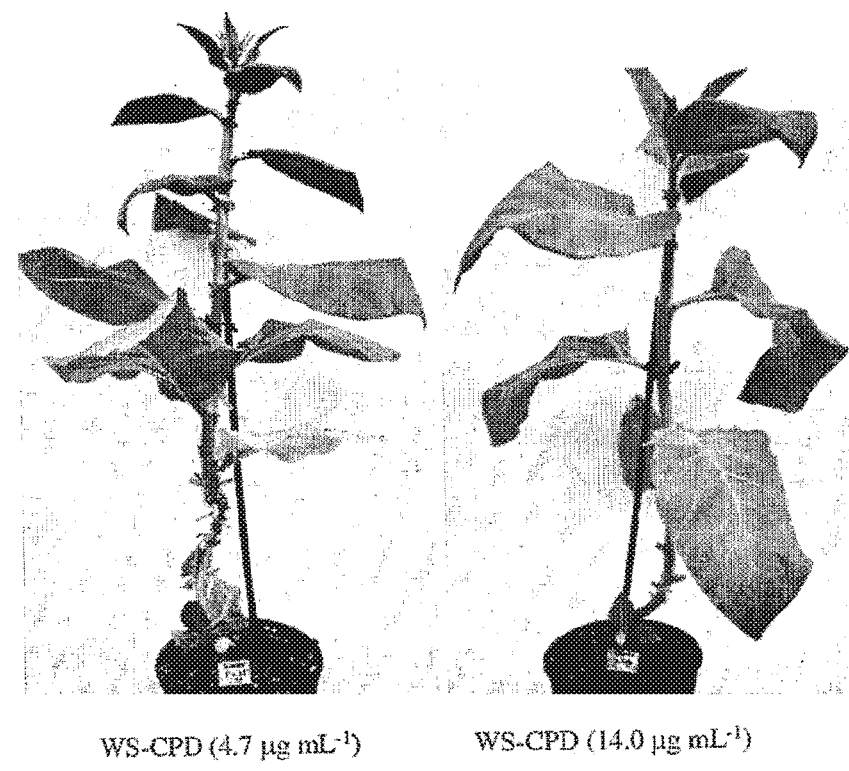
FIG. 14 Effect of pretreatment with WS-CPD spraying on ethylene (10 μL L$^{-1}$)-induced senescence of tobacco leaves.
Figure 15:
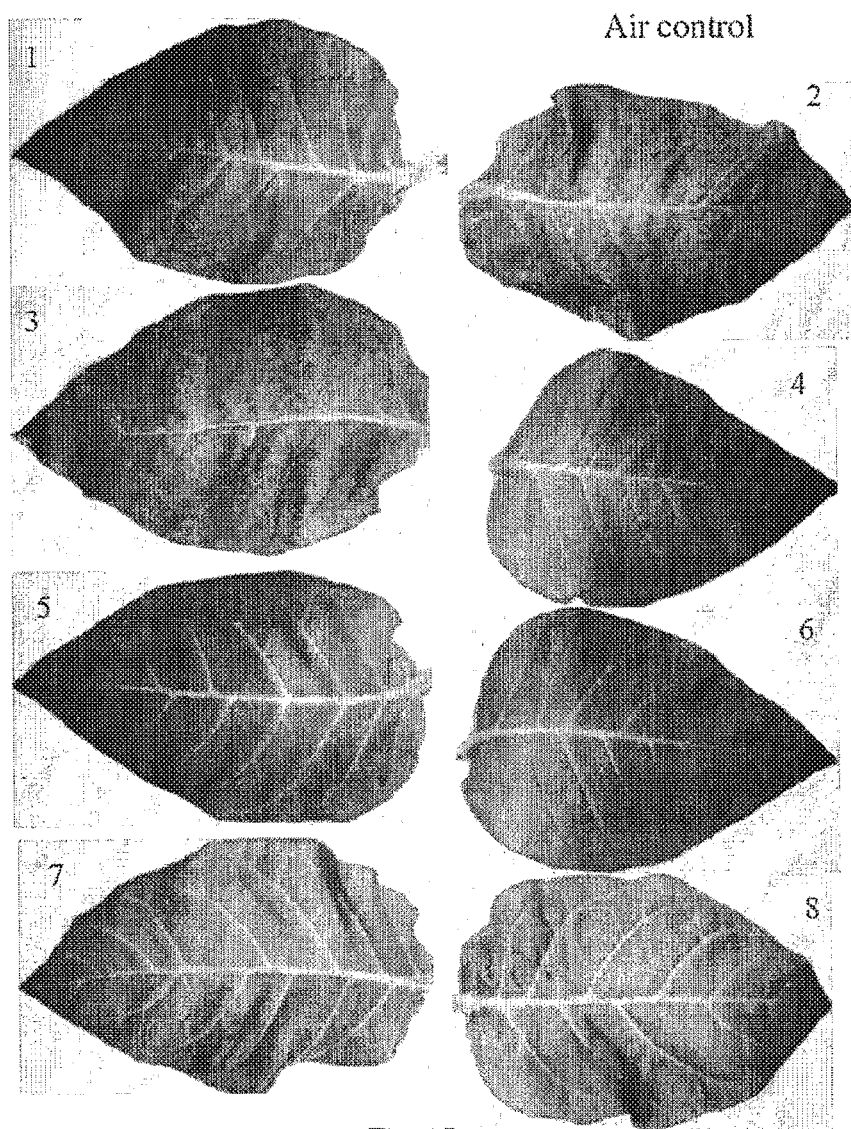
FIG. 15 Air control leaves of tobacco seedlings, from the top (leaf 1) to the base of the stem (leaf 8)
Figure 16:
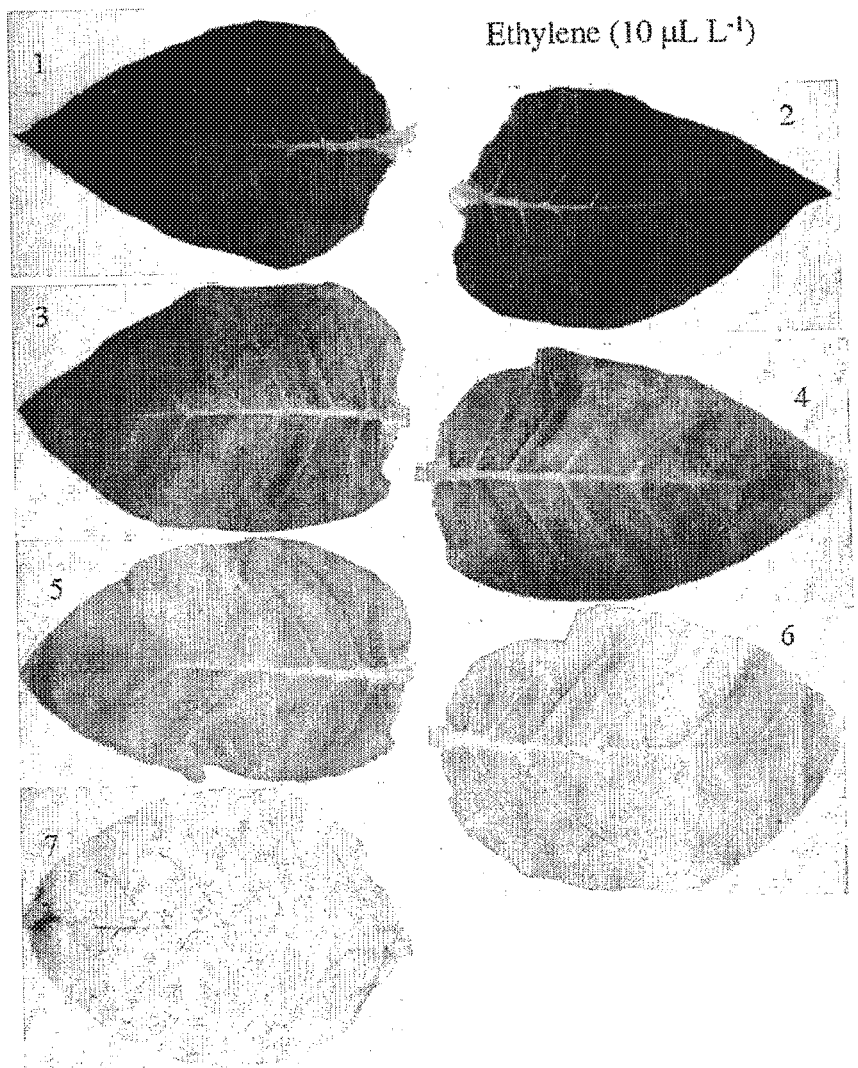
FIG. 16 Ethylene (10 μL L$^{-1}$)-induced leaf senescence of tobacco seedlings, from the top (leaf 1) to the base of the stem (leaf 7)
Figure 17:
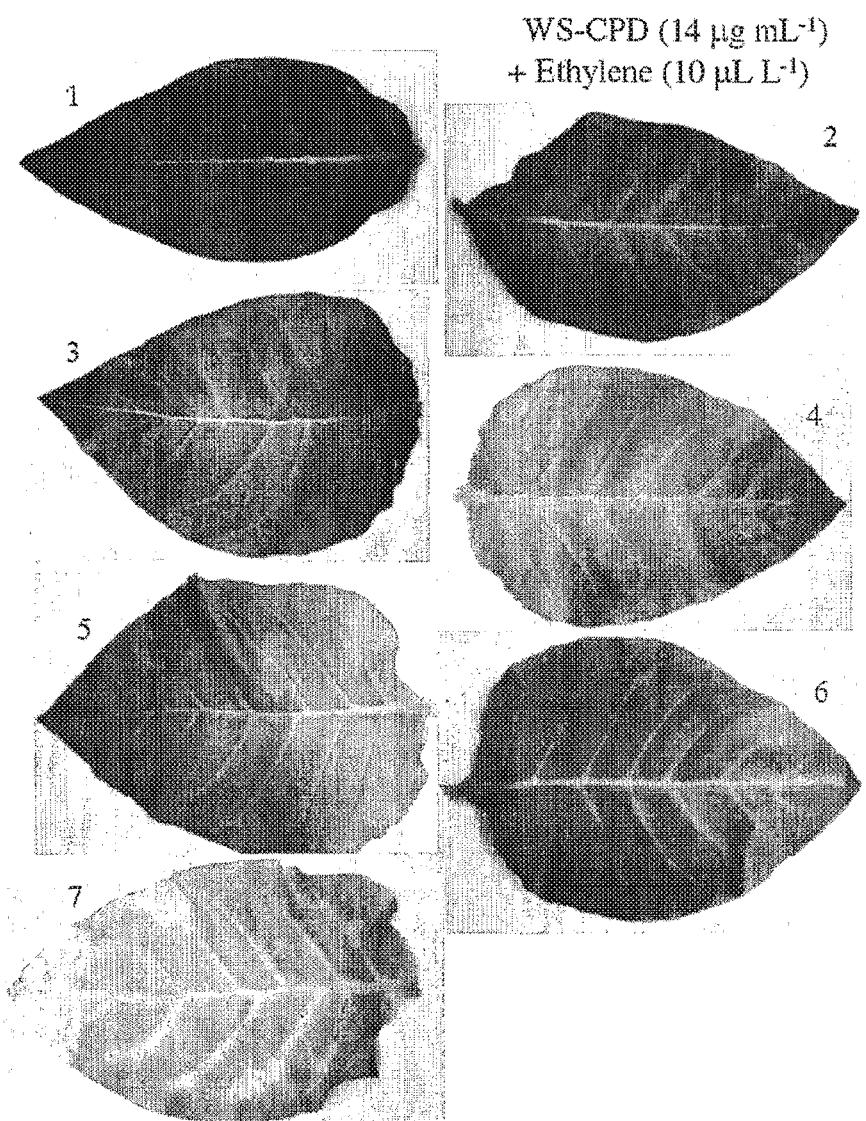
FIG. 17 Effect of pretreatment with WS-CPD spraying (14 μg mL$^{-1}$) on ethylene (10 μL L$^{-1}$)-induced senescence of tobacco leaves, from the top (leaf 1) to the base of the stem (leaf 7)
Figure 18:
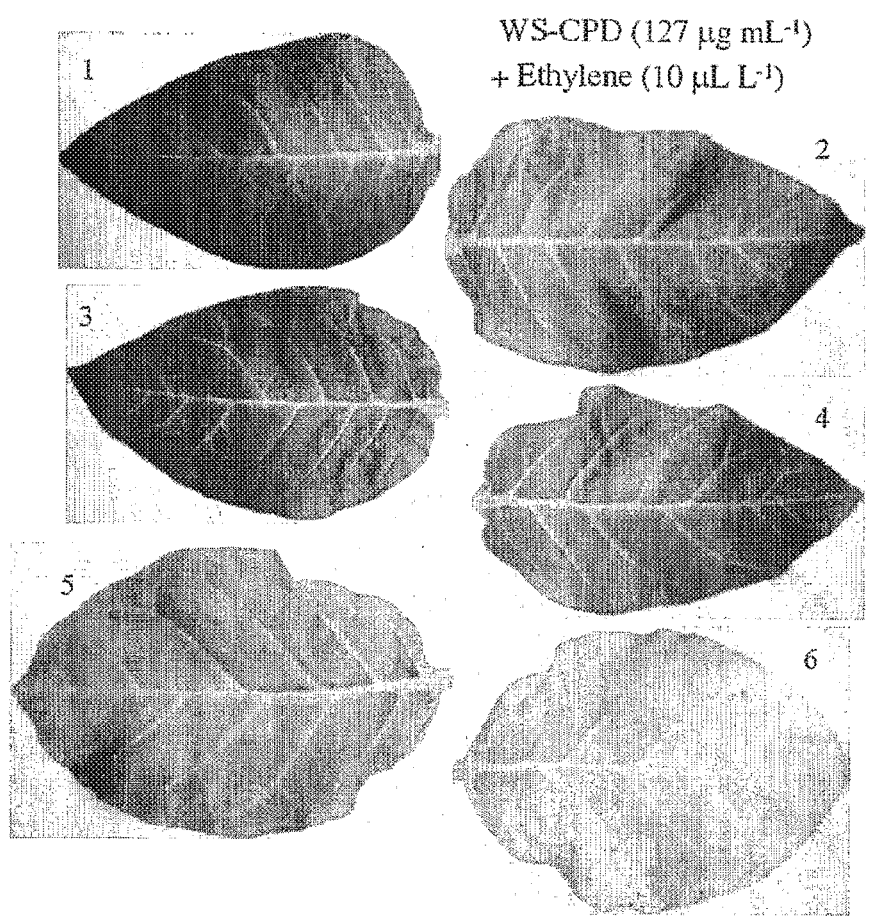
FIG. 18 Effect of pretreatment with WS-CPD spraying (127 μg mL$^{-1}$) on ethylene (10 μL L$^{-1}$)-induced senescence of tobacco leaves, from the top (leaf 1) to the base of the stem (leaf 6)
Figure 19:
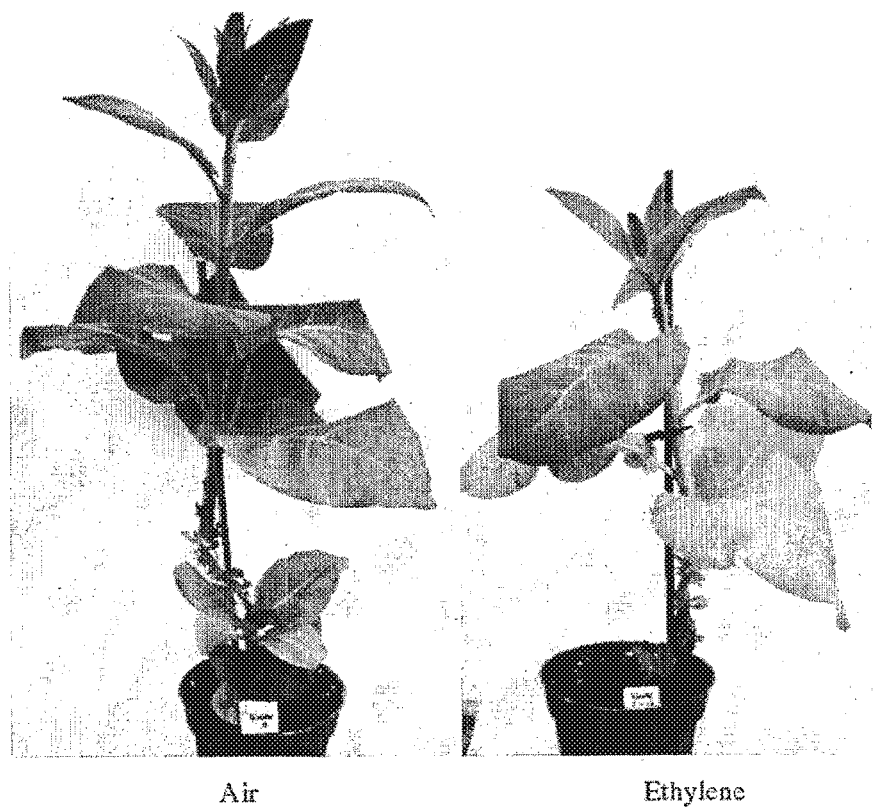
FIG. 19 Effect of pretreatment with WS-CPD spraying on ethylene (20 μL L$^{-1}$)-induced leaf senescence of tobacco seedlings.
Figure 20:
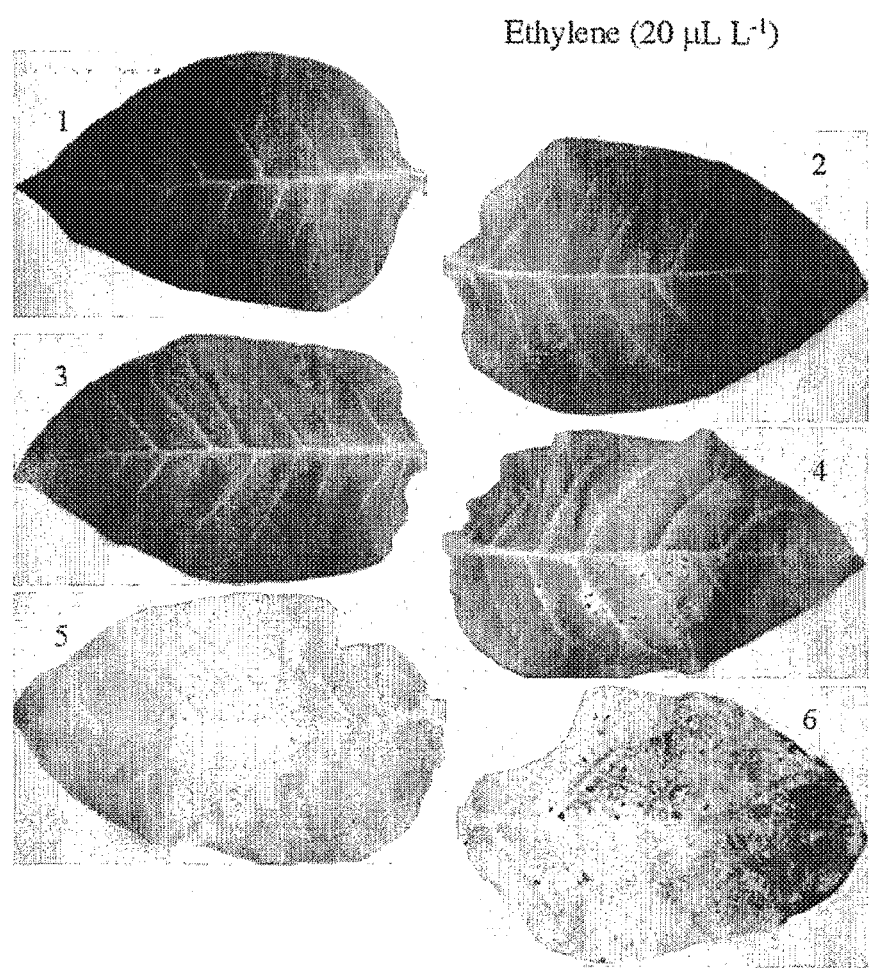
FIG. 20 Ethylene (20 μL L$^{-1}$)-induced leaf senescence of tobacco seedlings from the top (leaf 1) to the base of the stem (leaf 6)
Figure 21:
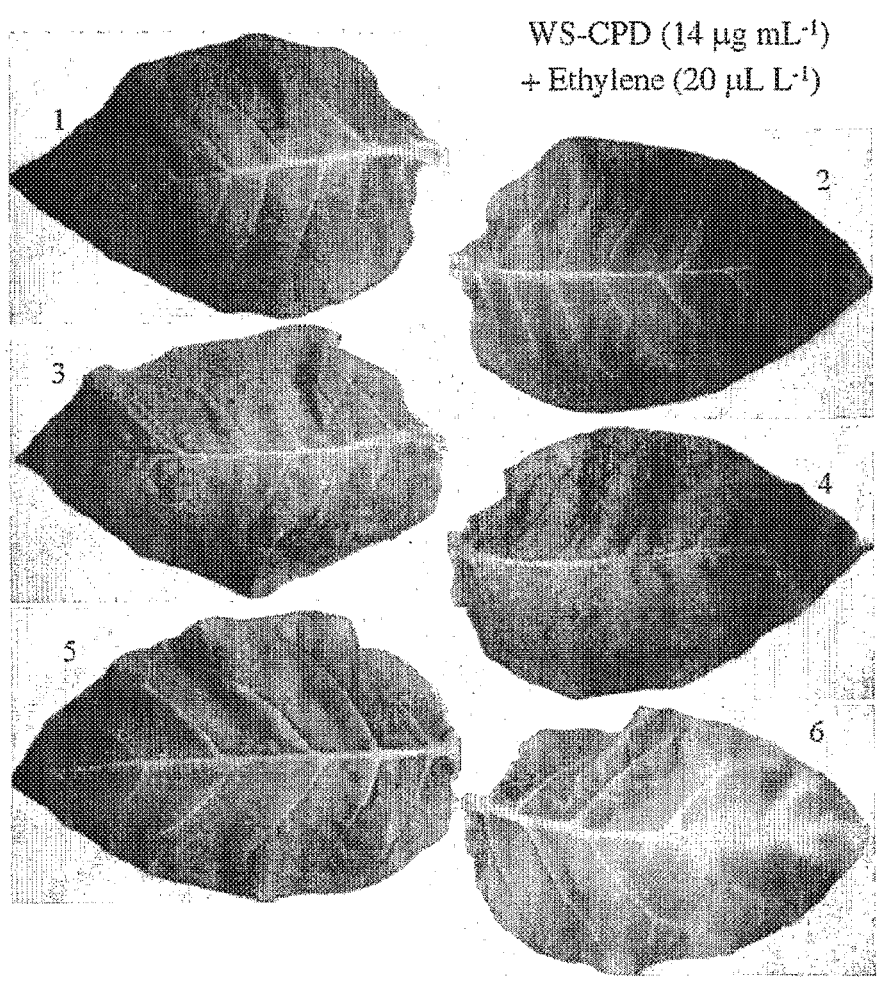
FIG. 21 Effect of pretreatment with WS-CPD spraying (14 μg mL$^{-1}$) on ethylene (20 μL L$^{-1}$)-induced senescence of tobacco leaves, from the top (leaf 1) to the base of the stem (leaf 6)
Figure 22:
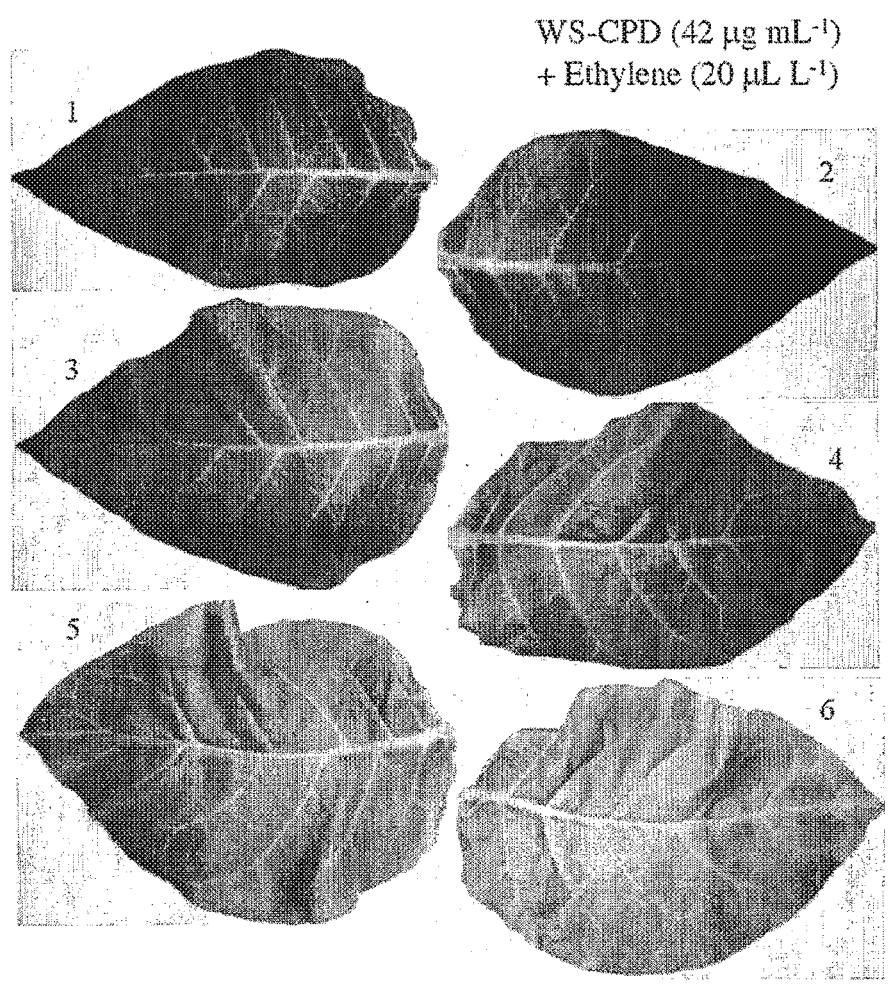
FIG. 22 Effect of pretreatment with WS-CPD spraying (42 μg mL$^{-1}$) on ethylene (20 μL L$^{-1}$)-induced senescence of tobacco leaves, from the top (leaf 1) to the base of the stem (leaf 6)
Figure 23:
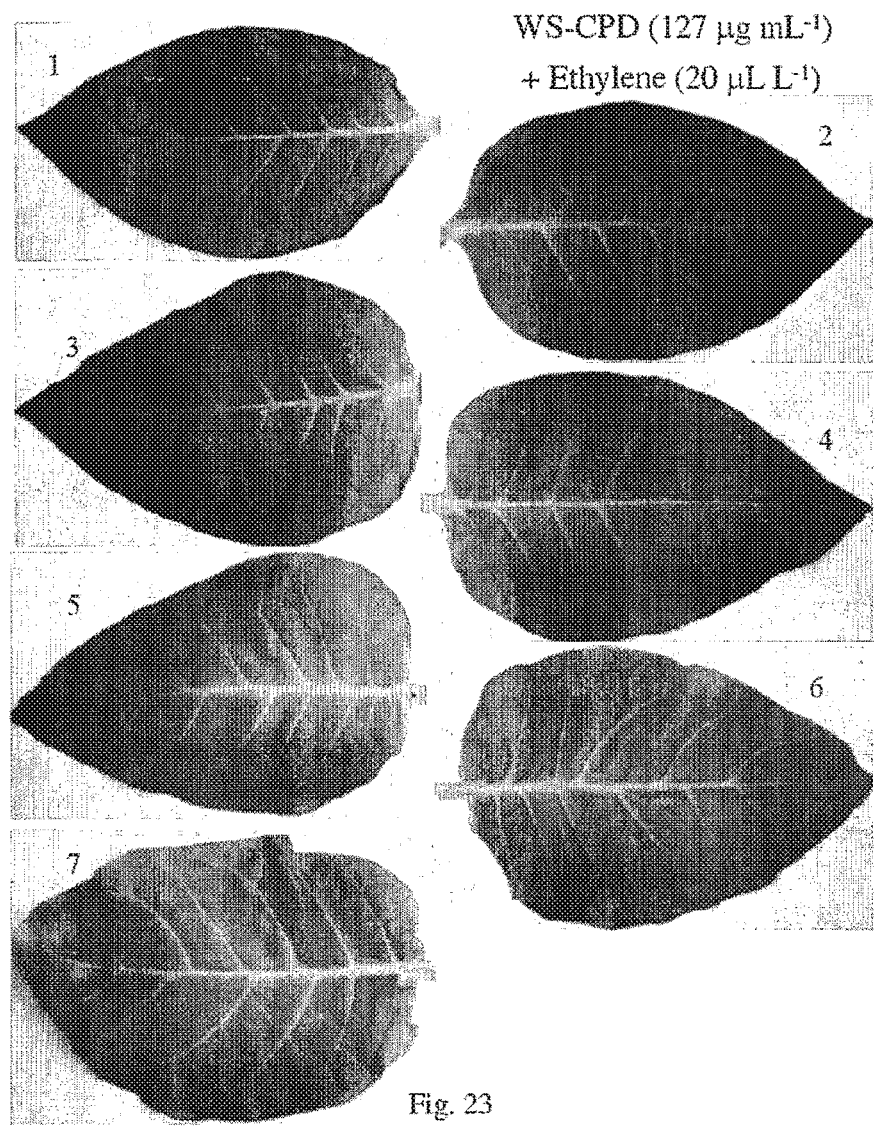
FIG. 23 Effect of pretreatment with WS-CPD spraying (127 μg mL$^{-1}$) on ethylene (20 μL L$^{-1}$)-induced senescence of tobacco leaves, from the top (leaf 1) to the base of the stem (leaf 7)

Leaf yellowing—Visible degreening of the leaf blade develops gradually and changes the leaf color from green to yellow as part of the senescence processes of intact seedlings. This change can be quantified by chlorophyll analysis. Tobacco leaves are very sensitive to ethylene-induced chlorophyll degradation. This sensitivity increases during leaf maturation (FIG. 13). Young leaves are resistant to ethylene and do not show any visual change in their green color after ethylene treatment (FIGS. 13, 15 and 16). By using the standard experimental procedure, namely a pretreatment spray with WS-CPD followed by exposure to ethylene (10 μL L$^{-1}$), and further incubation in a controlled growth camber (85% humidity, 22° C., regular fluorescent light). 14 μg mL$^{-1}$ of WS-CPD antagonized the ethylene-induced senescence only in mature leaves (FIGS. 14-17). A concentration of 127 μg mL$^{-1}$ WS-CPD was also slightly effective in young leaves (FIG. 18). By increasing the concentration of ethylene to 20 μL L$^{-1}$, leaf yellowing was intensified in mature leaves (FIGS. 19 and 20), but even in this case pretreatment with 14 to 127 μg mL$^{-1}$ of WS-CPD very significantly inhibited leaf yellowing (FIGS. 21-23).

Figure 24:
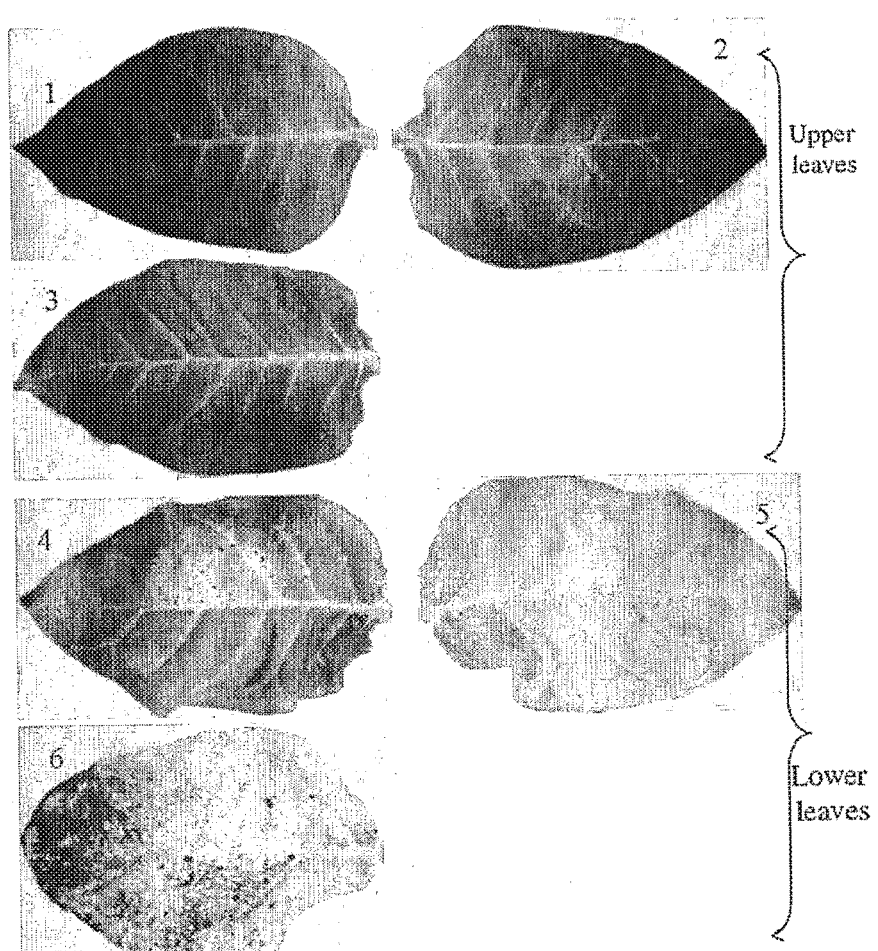
FIG. 24 Upper (leaves 1-3) and lower (leaves 4-6) leaves of tobacco seedling sampled for chlorophyll determination.
Figure 25:
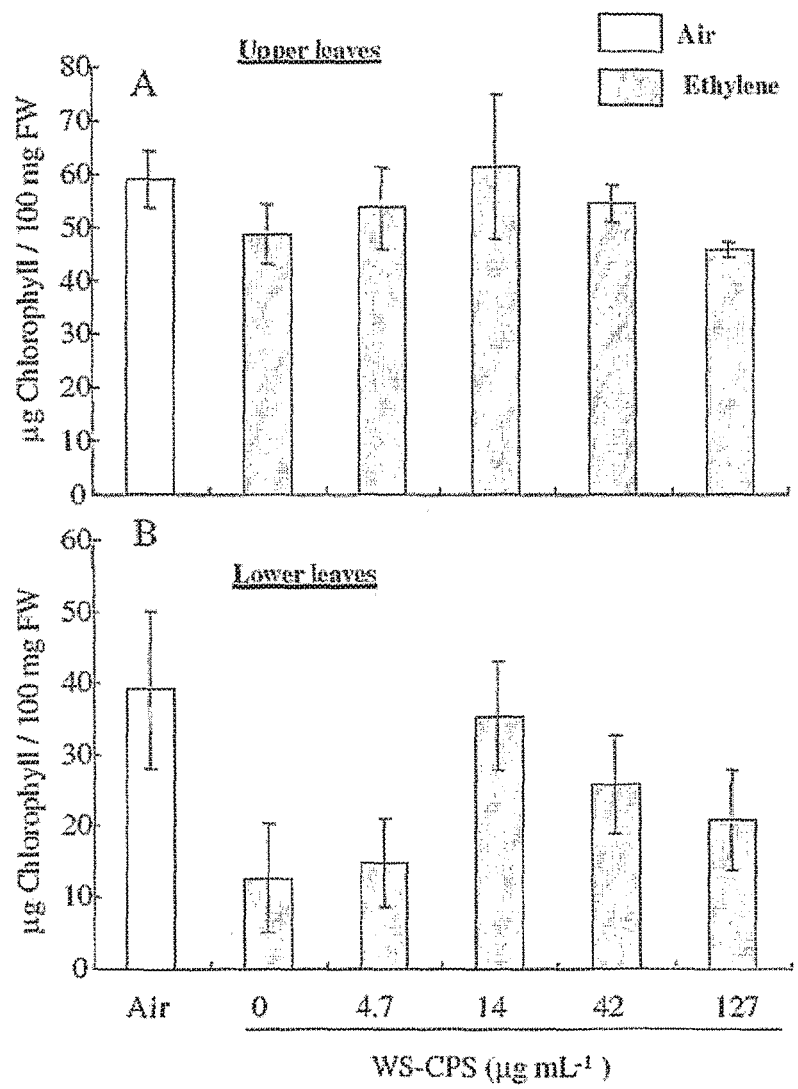
FIG. 25 Effect of pretreatment with WS-CPD spraying on ethylene (20 µL L$^{-1}$)-induced reduction in chlorophyll content in the upper and lower leaves of tobacco seedlings.

Chlorophyll degradation—Chlorophyll content was determined in both young (upper) and mature (lower) leaves of young seedlings (FIGS. 24 and 25). Although there was no visible degreening in young ethylene-treated leaves (FIG. 24), there was a 17% decrease in their chlorophyll content as compared with air-treated leaves (FIG. 25*a*). Ethylene reduced chlorophyll content by 72% in mature leaves (FIG. 25*a*). A pretreatment spray with 14 μg mL$^{-1}$ of WS-CPD completely reversed the ethylene-induced chlorophyll degradation in young and mature leaves (FIG. 25*a, b*), while higher concentrations were less effective.

Vegetative Growth of Young Wheat Seedlings

Figure 26:
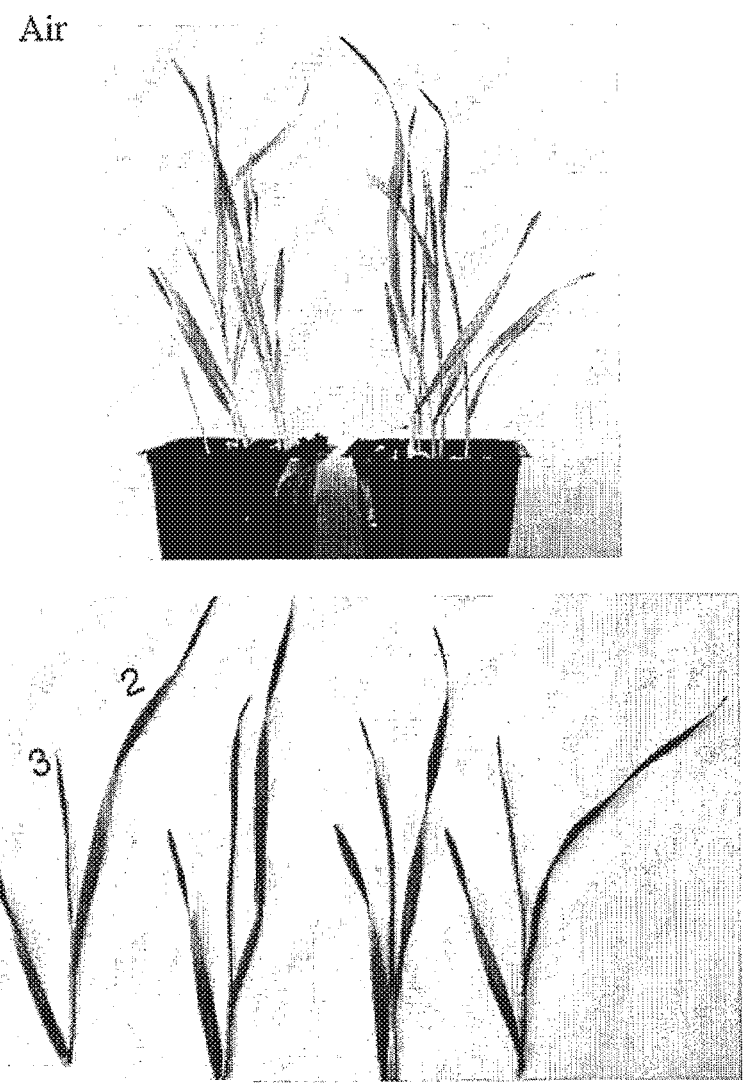
FIG. 26 Wheat seedlings 14 days after germination (air control)
Figure 27:
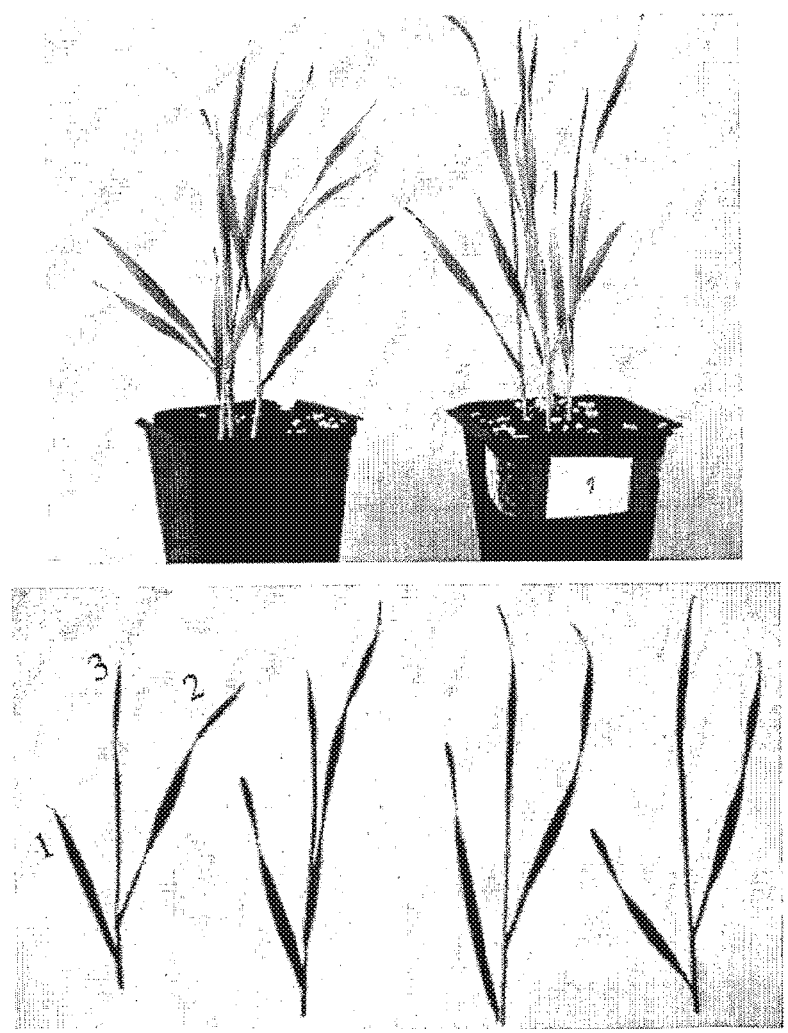
FIG. 27 Effect of 1 µL L$^{-1}$ ethylene exposure at day 10 on development of the 3$^{rd}$ leaf of wheat seedlings, 14 days after germination.
Figure 28:
FIG. 28 Effect of 10 µL L$^{-1}$ ethylene exposure at day 10 on development of the 3$^{rd}$ leaf of wheat seedlings, 14 days after germination.
Figure 29:
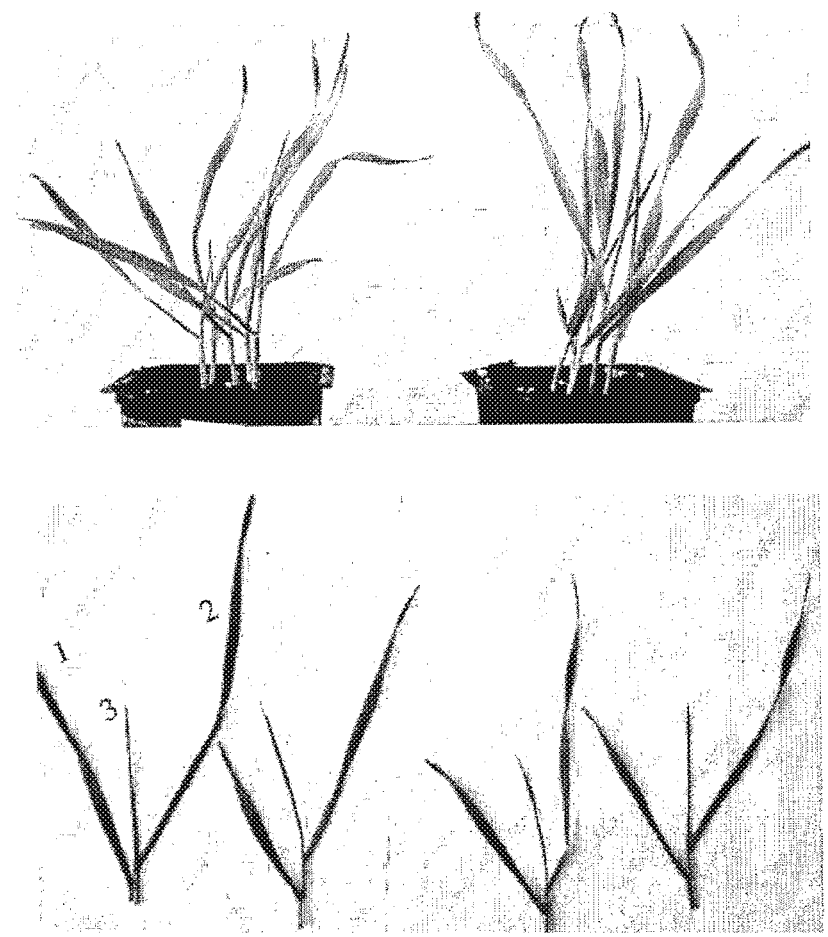
FIG. 29 Effect of 100 µL L$^{-1}$ ethylene exposure at day 10 on development of the 3$^{rd}$ leaf of wheat seedlings, 14 days after germination.
Figure 30:
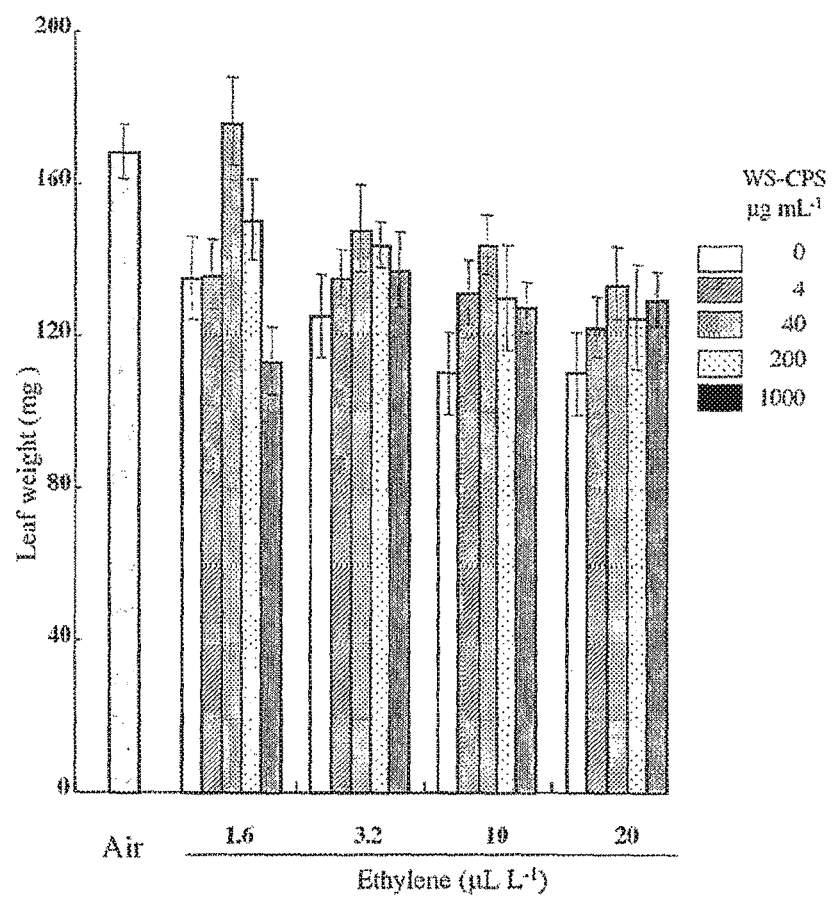
FIG. 30 Effect of pretreatment with WS-CPD spraying (4-1000 µg mL$^{-1}$), applied at day 10 after germination, on ethylene (1.6-20 µL L$^{-1}$)-induced delay of 3$^{rd}$ leaf weight of wheat seedlings. Results were recorded 14 days after germination.

Ten days after germination the first two leaves almost reached their final length. The third leaf reached its final length three days later (FIG. 26). Continuous exposure of the seedlings during this period to ethylene (1 μL L$^{-1}$) showed that the length of the third leaf was longer by 50% than the length of the same mature air-control leaf (FIG. 27). Exposure of the seedlings to 10 and 100 μL L$^{-1}$ ethylene inhibited the growth of the third leaf by 50 to 30%, respectively, compared to air control leaves (FIGS. 28 and 29). In an additional experiment, exposing the seedlings to 1.6-20 μL L$^{-1}$ ethylene inhibited the growth of the third leaf by 20 to 35%, respectively. A pretreatment spray with different concentrations of WS-CPD at day 10 after germination, and exposing the seedlings 24 h later to ethylene (1.6 to 40 μg L$^{-1}$) for an additional two days, demonstrated that only low concentrations of WS-CPD (4 and 40 μg mL$^{-1}$) effectively antagonized the inhibitory effect of ethylene of the third leaf growth and that 40 μg mL$^{-1}$ of WS-CPD reversed the inhibitory effect of 1.6 ethylene by 100% (FIG. 30).

Leaf Epinasty of Wheat Plants after Spike Heading

Figure 31:
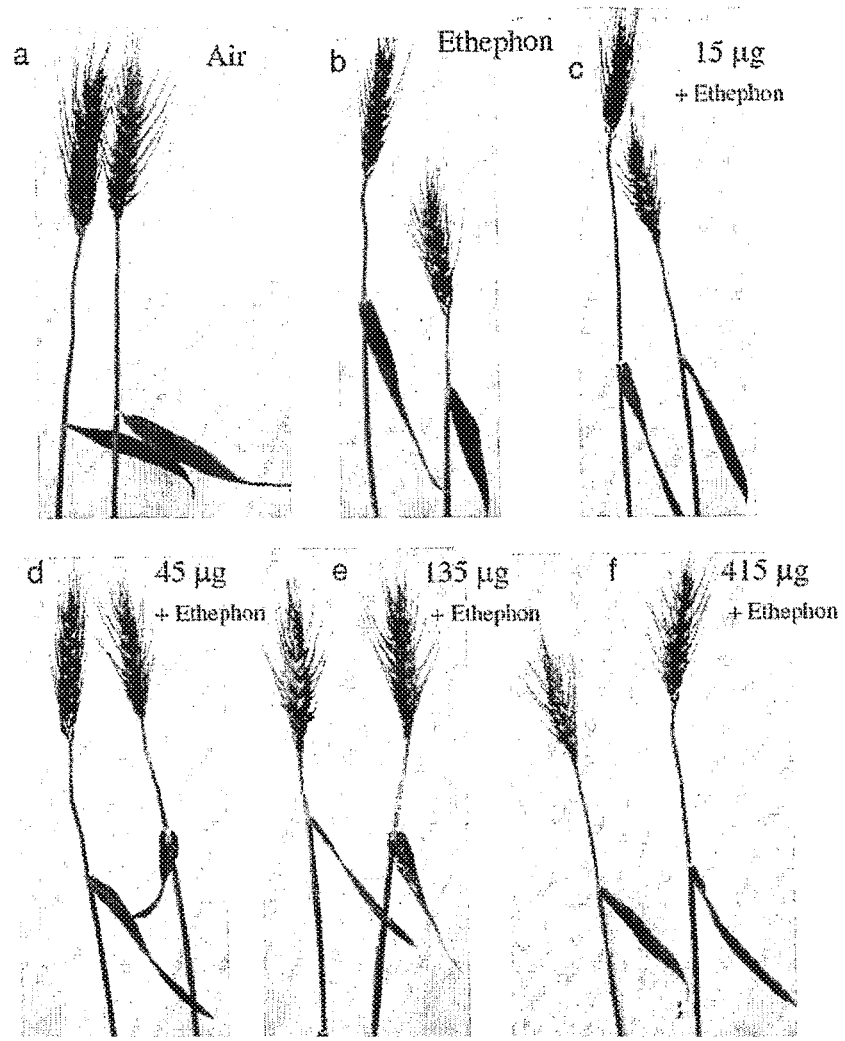
FIG. 31 Effect of pretreatment with WS-CPD spraying (15-415 µg mL$^{-1}$) followed by Ethephon™ (750 µL L$^{-1}$) treatment at milky stage I of the spike on the flag leaf epinasty.
Figure 32:
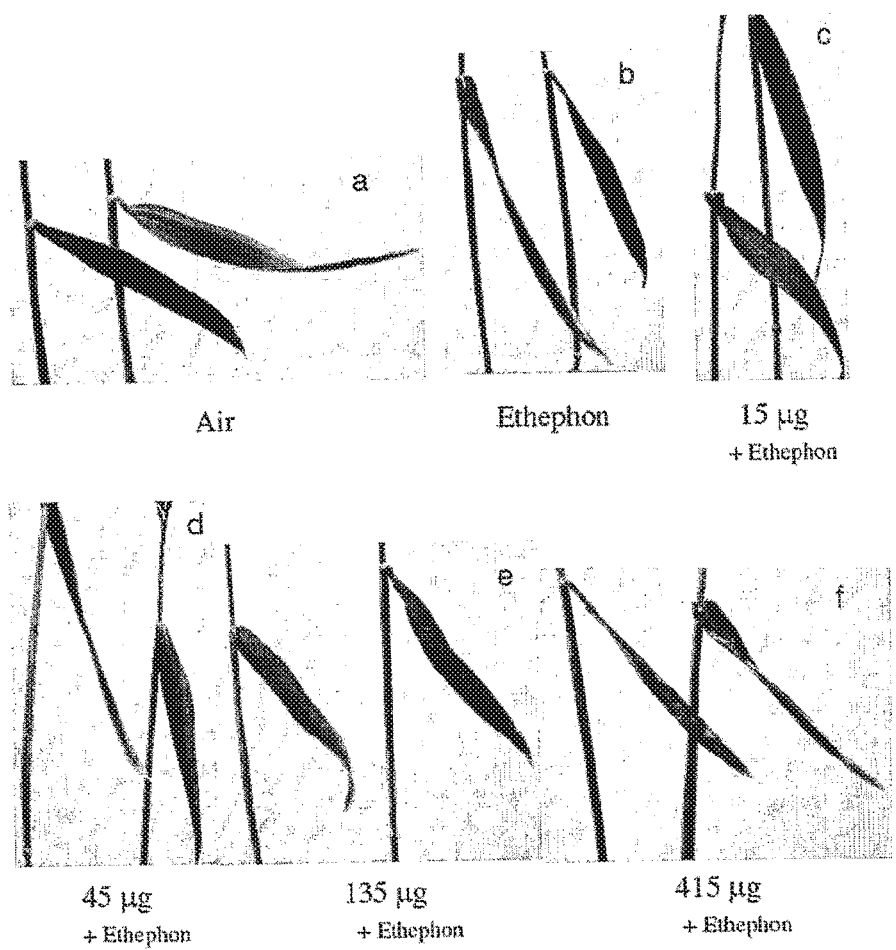
FIG. 32 Effect of pretreatment with WS-CPD spraying (15-415 µg mL$^{-1}$) followed by Ethephon™ (750 µL L$^{-1}$) treatment at milky stage I of the spike on the flag leaf epinasty.
Figure 33:
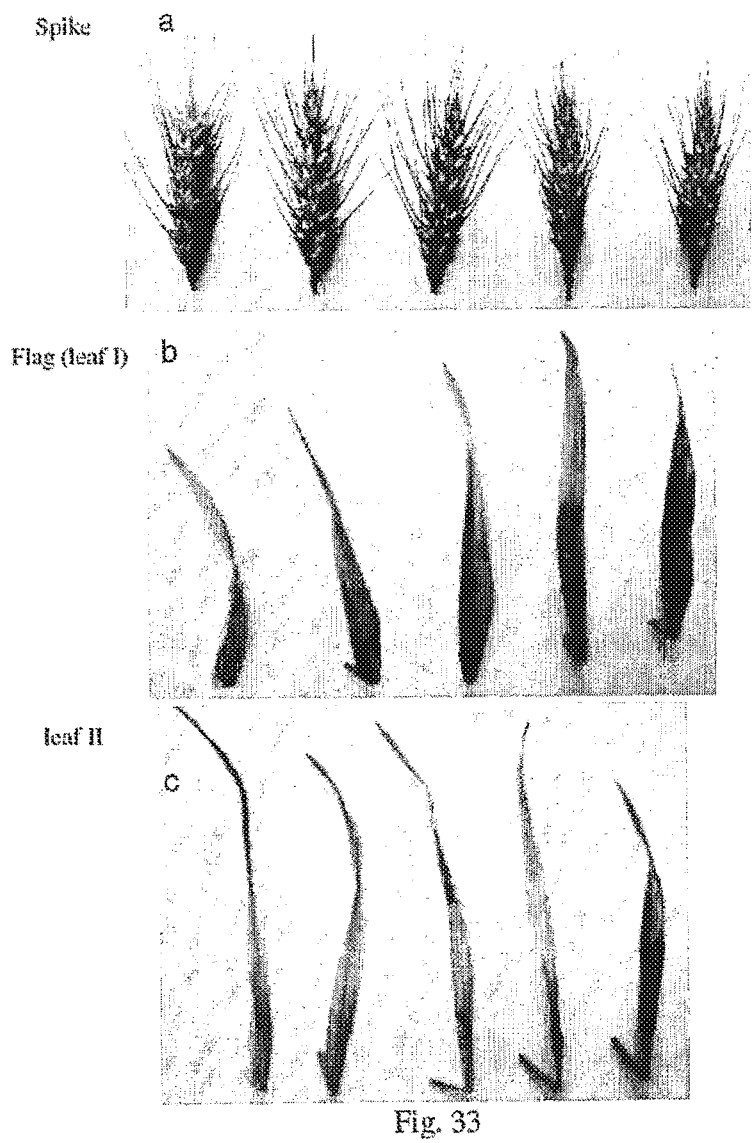
FIG. 33 Ethephon™ (750 µL L$^{-1}$)-induced leaf senescence of leaf I and II at the milky stage I of the spike.
Figure 34:
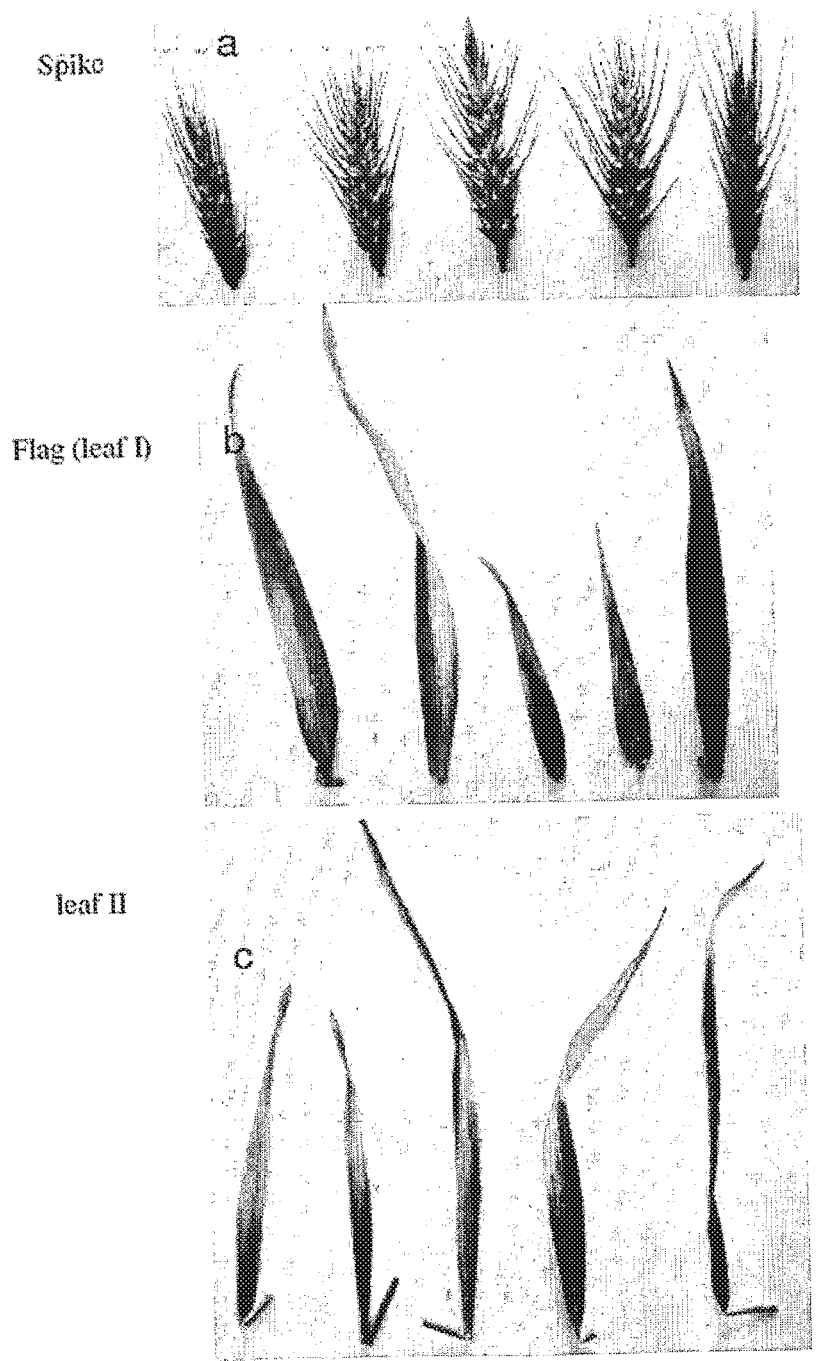
FIG. 34 Effect of pretreatment with WS-CPD (15 µg mL$^{-1}$) at milky stage I of the spike on Ethephon™ (750 µL L$^{-1}$)-induced leaf senescence of leaf I and II.
Figure 35:
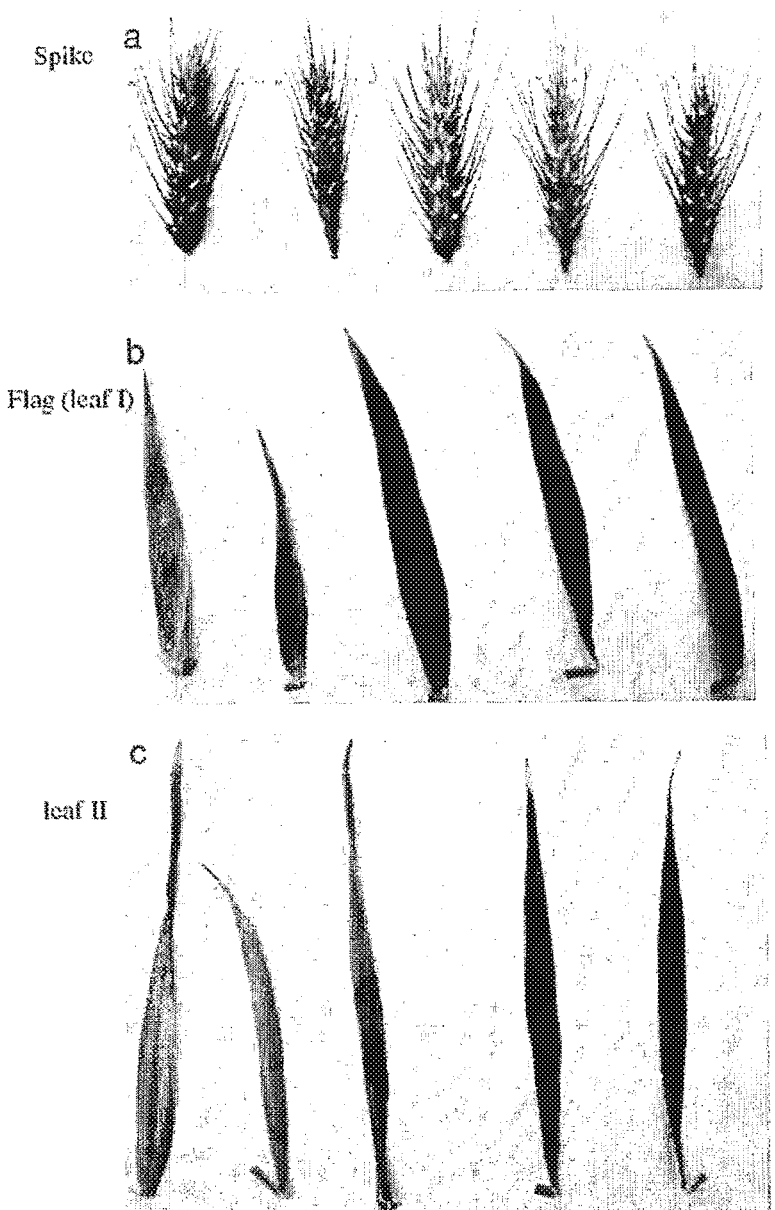
FIG. 35 Effect of pretreatment with WS-CPD (45 µg mL$^{-1}$) at milky stage I of the spike on Ethephon™ (750 µL L$^{-1}$)-induced leaf senescence of leaf I and II.
Figure 36:
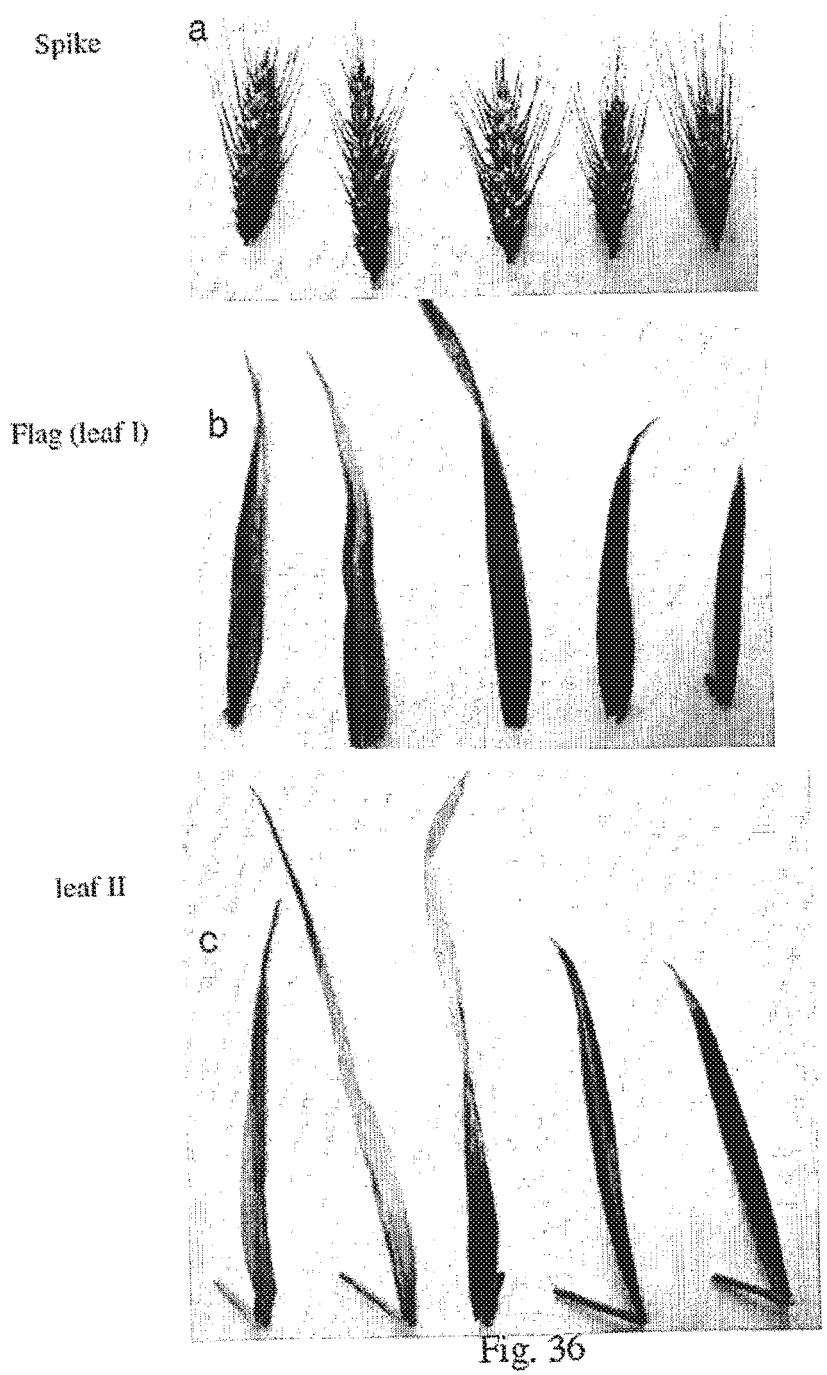
FIG. 36 Effect of pretreatment with WS-CPD (135 µg mL$^{-1}$) at milky stage I of the spike on Ethephon™ (750 µL L$^{-1}$)-induced leaf senescence of leaf I and II.
Figure 37:
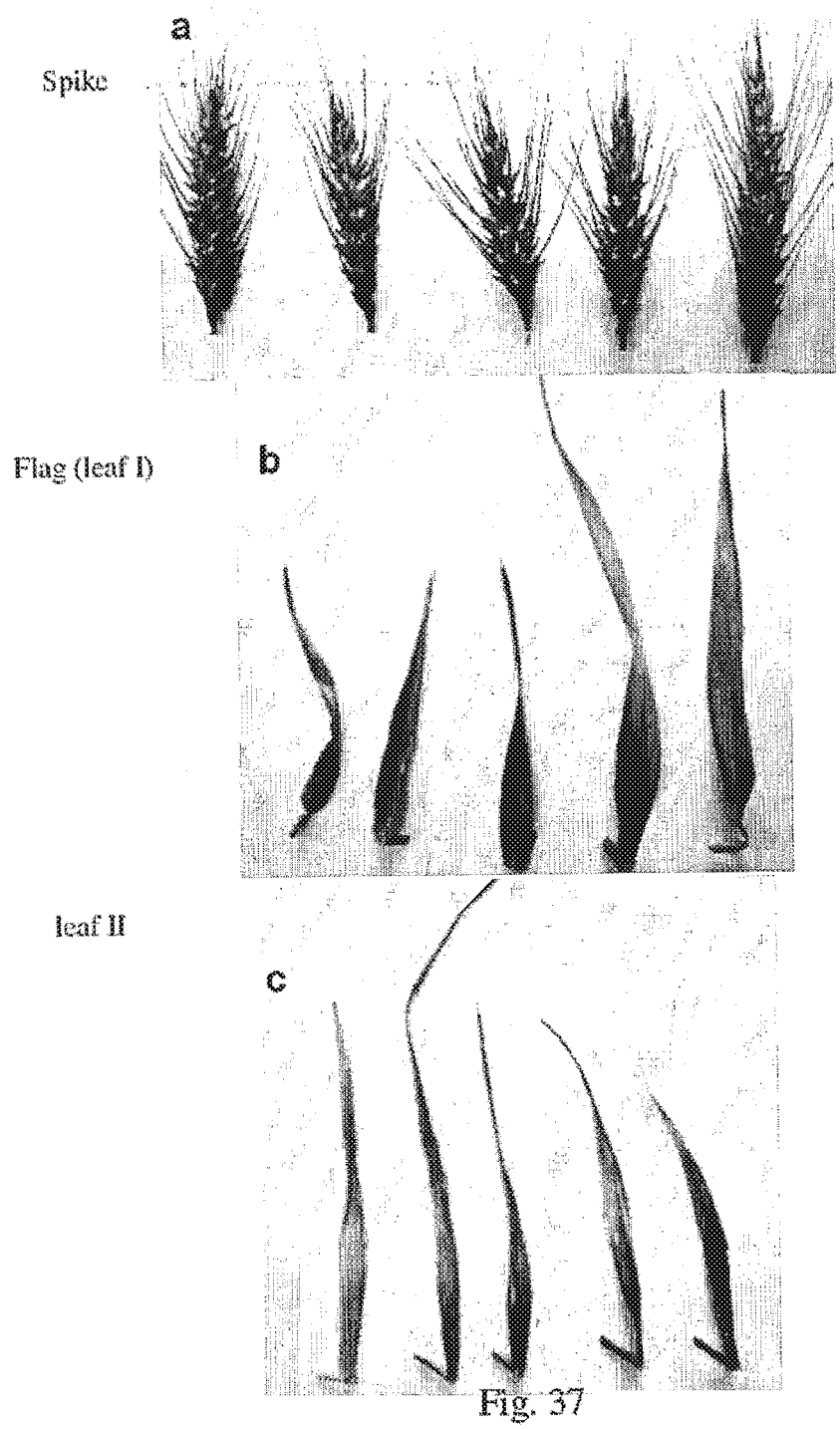
FIG. 37 Effect of pretreatment with WS-CPD (450 µg mL$^{-1}$) at milky stage I of the spike on Ethephon™ (750 µL L$^{-1}$)-induced leaf senescence of leaf I and II.
Figure 38:
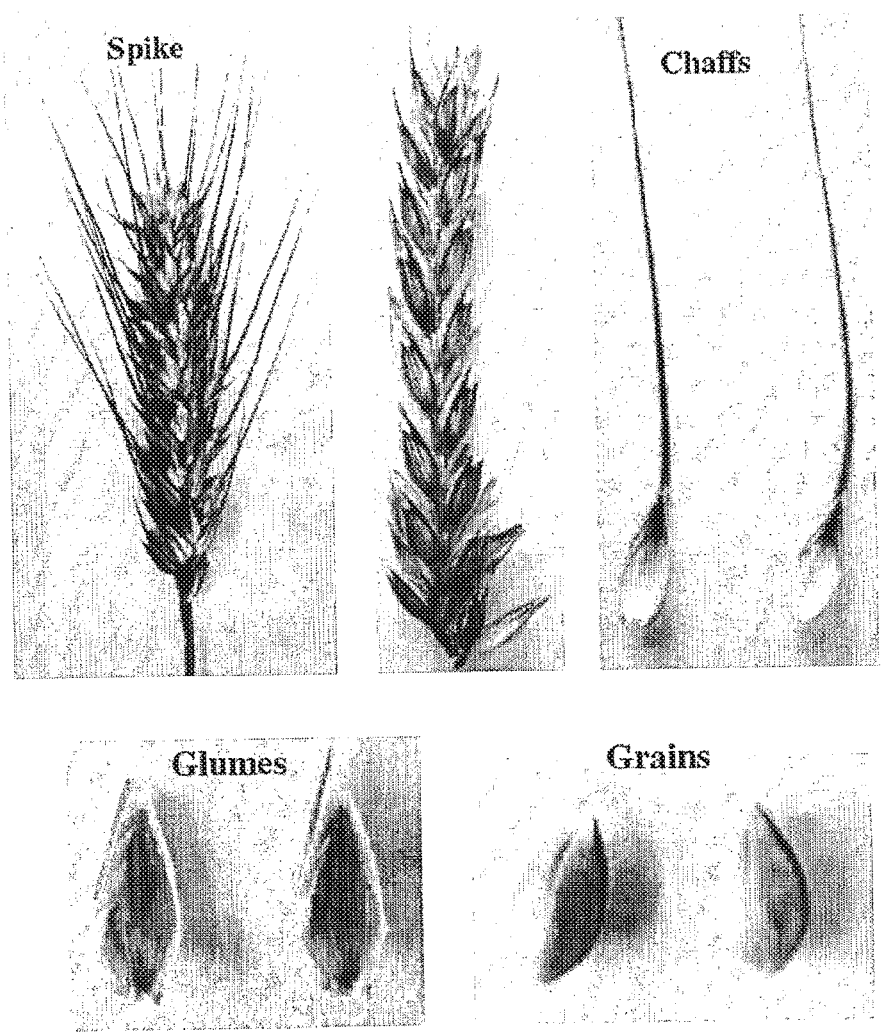
FIG. 38 Demonstration of the organs of the wheat spike.

After the spike heading stage (6 months after germination), the plants were sprayed with Ethephon™ (750 μL L$^{-1}$) following a pretreatment spray with WS-CPD (15 to 415 μg mL$^{-1}$). The flag leaf showed a strong leaf epinasty in response to Ethephon™ treatment. Pretreatment with 135 and 415 μg mL$^{-1}$ partly protected the flag leaf from Ethephon™-induced leaf epinasty (FIGS. 31 and 32).

Leaf Yellowing and Chlorophyll Degradation in Wheat Plants

Following the spike heading period the grains accumulated the photosynthetic products. The development of the grains consists of two stages, milky stage I and II, which are followed by the drying stage. These stages were accompanied by gradual decrease of the amount of chlorophyll in flag leaf and leaf II at stage I, from 245 and 260 μg 100 mg$^{-1}$ FW (FIG. 39) to 120 and 150 μg at stage II (FIG. 43), respectively. A gradual decrease of chlorophyll was also detected in glumes and chaffs of the spike from 80 and 170 µg in stage I (FIG. 40) to 45 and 70 µg 100 mg$^{-1}$ (FW) at stage II (FIG. 44), respectively.

Figure 39:
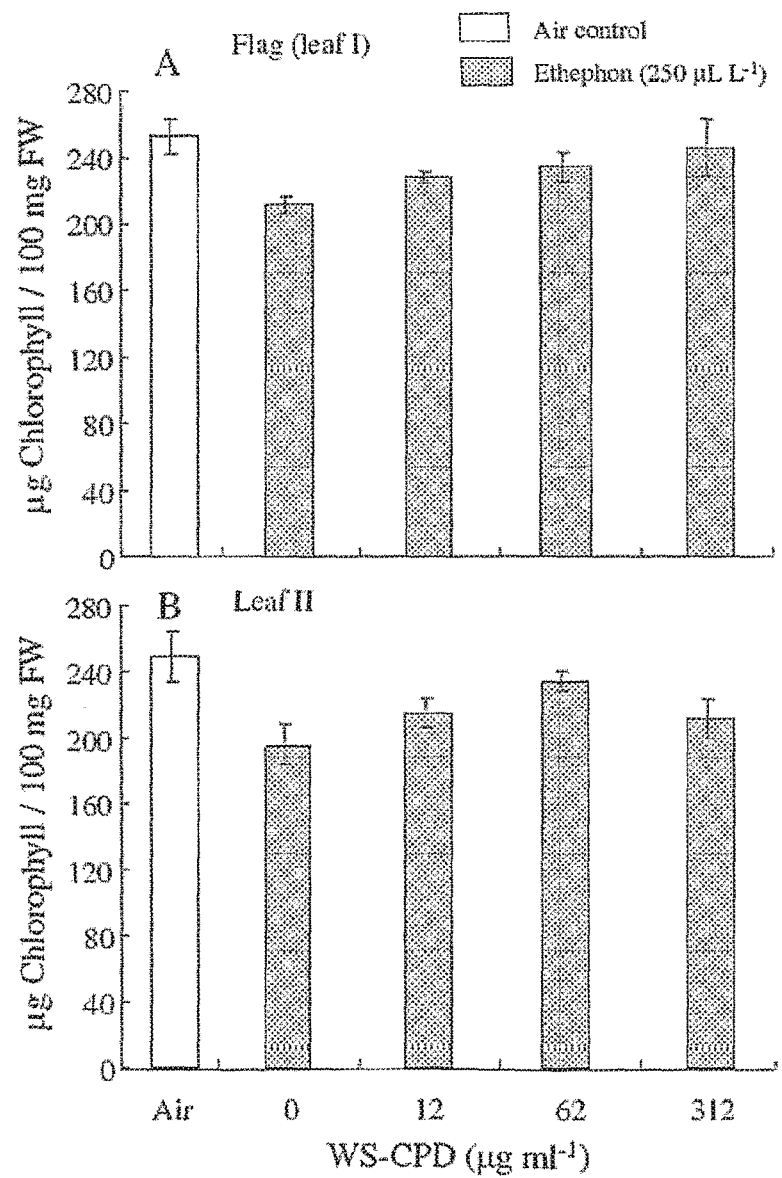
FIG. 39 Effect of pretreatment with WS-CPD (12-312 µg mL$^{-1}$) at the milky stage I of the spike, followed by Ethephon™ (250 µL L$^{-1}$) treatment, on the chlorophyll content of leaf I and II.
Figure 40:
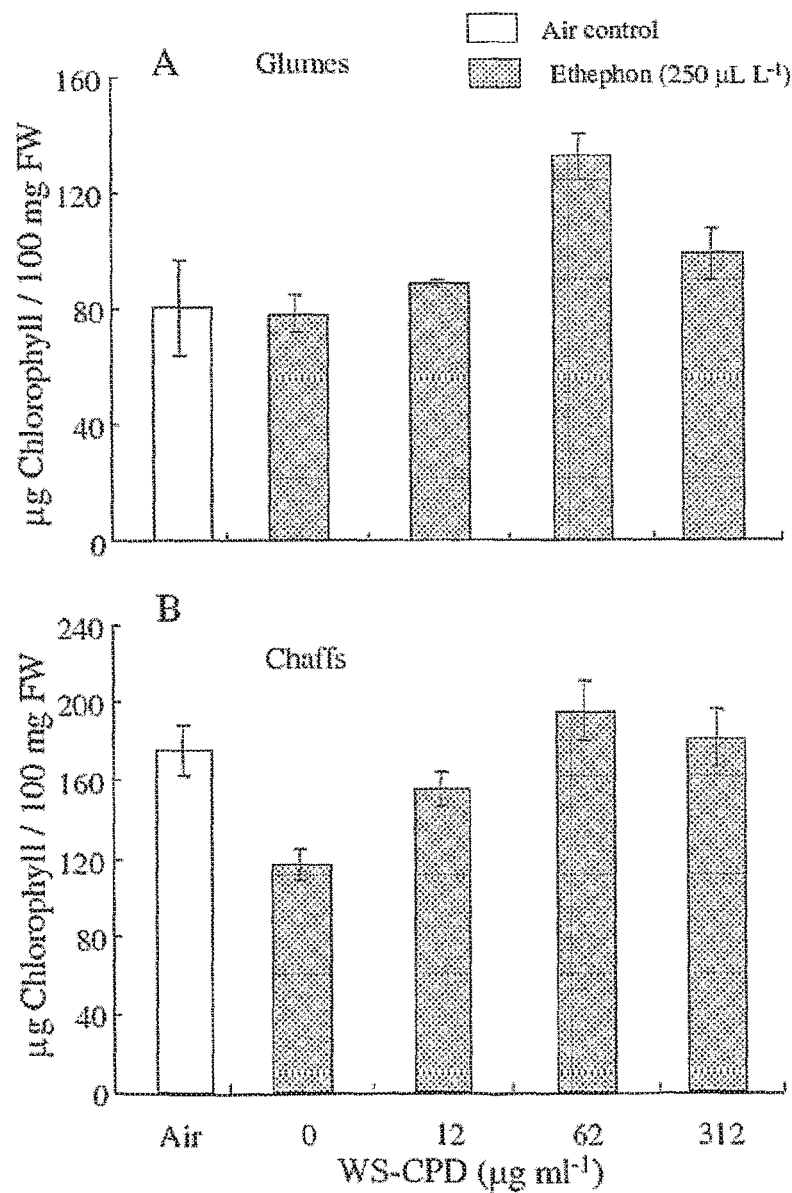
FIG. 40 Effect of pretreatment with WS-CPD (12-312 µg mL$^{-1}$) at the milky stage I of the spike, followed by Ethephon™ (250 µL L$^{-1}$) treatment, on the chlorophyll content of the glumes and chaffs.
Figure 41:
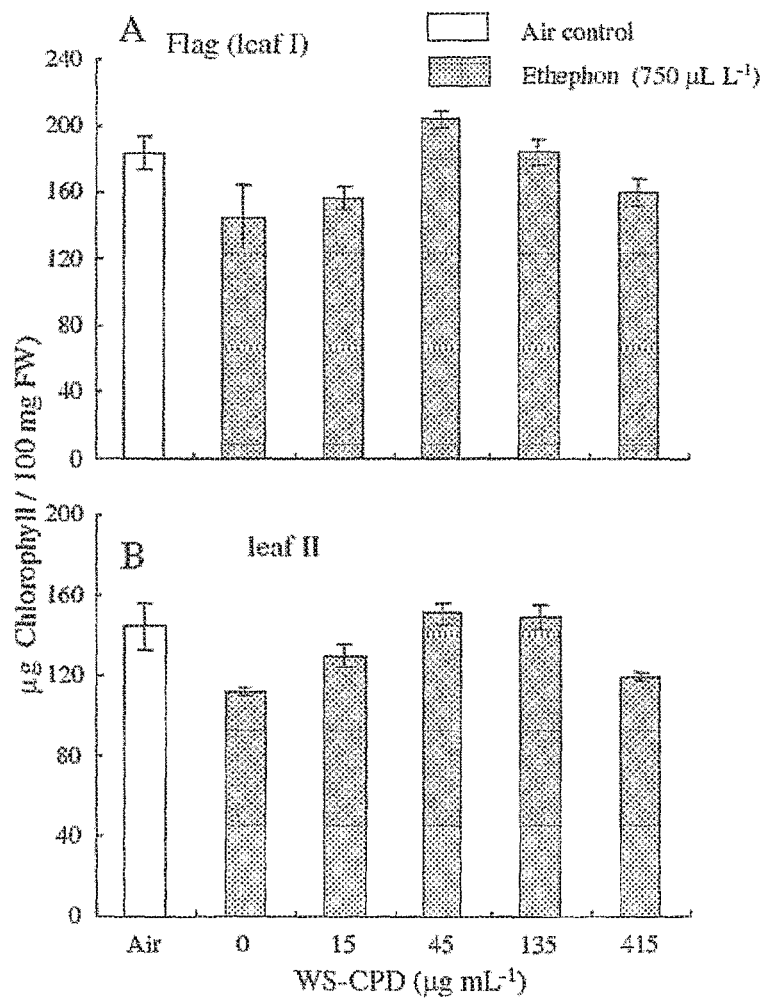
FIG. 41 Effect of pretreatment with WS-CPD (15-415 µg mL$^{-1}$) at the milky stage I of the spike followed by Ethephon™ (750 µL L$^{-1}$) treatment, on the chlorophyll content of leaf I and II.

About 6.5 months after germination the plants were sprayed with Ethephon™ at milky stage I (250 and 750 µL L$^{-1}$; FIGS. 39 and 41, respectively). After 5-6 days, the chlorophyll content significantly decreased, by 16-21% in the flag leaf and by 21-22% in leaf II. Pretreatment with 12 to 62 µg mL$^{-1}$ of WS-CPD significantly reduced the Ethephon™-induced decrease of chlorophyll, mainly in the flag leaf (leaf I), but also in leaf II. In both experiments, the chlorophyll content after the WS-CPD treatment only slightly decreased compared to control plants (FIGS. 39 and 41). Increasing the concentration of WS-CPD to 312 µg mL$^{-1}$ was more effective and almost completely antagonized the decrease of chlorophyll content in the flag leaf induced by 250 µL L$^{-1}$ Ethephon™ treatment (FIG. 39A). Increasing the concentration of WS-CPD to 415 µg mL$^{-1}$ was much less effective in both types of leaves and only slightly antagonized the chlorophyll decrease induced by Ethephon™ (750 µL L$^{-1}$, FIG. 41).

Figure 42:
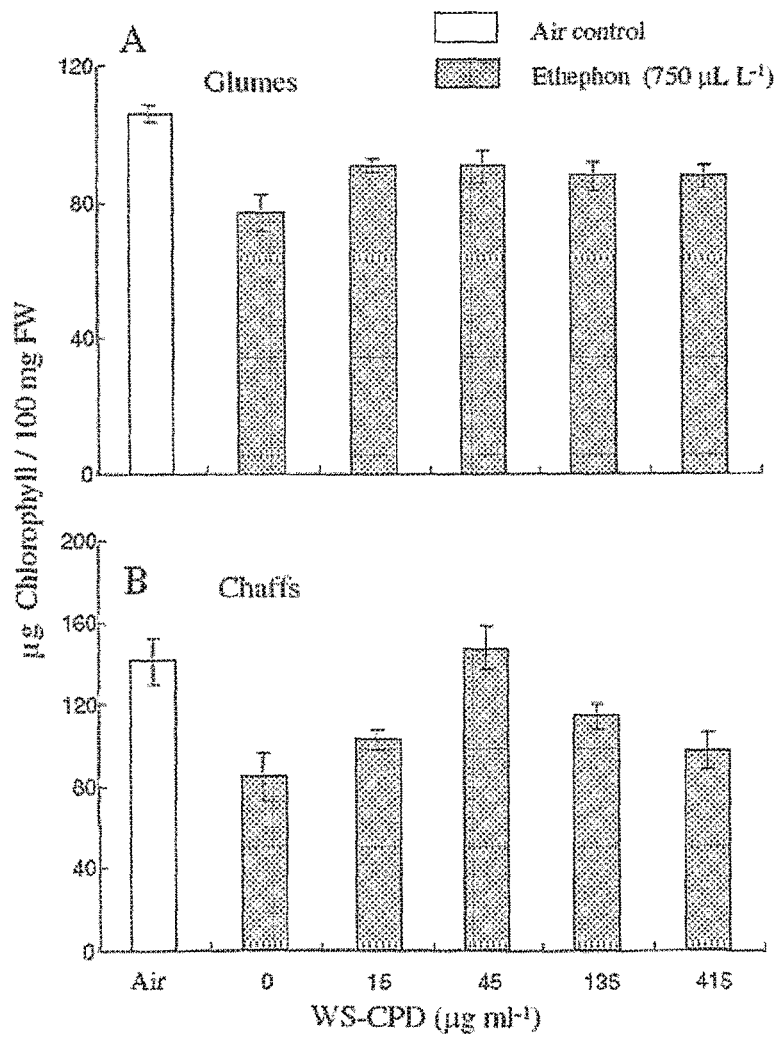
FIG. 42 Effect of pretreatment with WS-CPD (15-415 µg mL$^{-1}$) at the milky stage I of the spike followed by Ethephon™ (750 µL L$^{-1}$) treatment on the chlorophyll content of the glumes and chaffs.

Ethephon treatments with 250 and 750 µL L$^{-1}$ to the same plants significantly reduced the chlorophyll content by 33 and 28%, respectively, in the chaffes (FIGS. 40A and 42A). In the glumes the reduction in chlorophyll content was induced by the above Ethephon™ concentrations by 10 and 40%, respectively (FIGS. 40B and 42B). Similar to leaves, pretreatment with WS-CPD (62 µg mL$^{-1}$) completely reversed the Ethephon™ (250 µL L$^{-1}$)-induced chlorophyll degradation in the glumes and chaffs, and even increased their chlorophyll content (by 60 and 10%, respectively), above the content in the control untreated plants (FIGS. 40A and B). WS-CPD (45 µg mL$^{-1}$) markedly antagonized the Ethephon™ (750 µL L$^{-1}$)-induced decrease in the content of chlorophyll of the chaffs (FIG. 42B), but was much less effective on the glumes (FIG. 42A).

Figure 43:
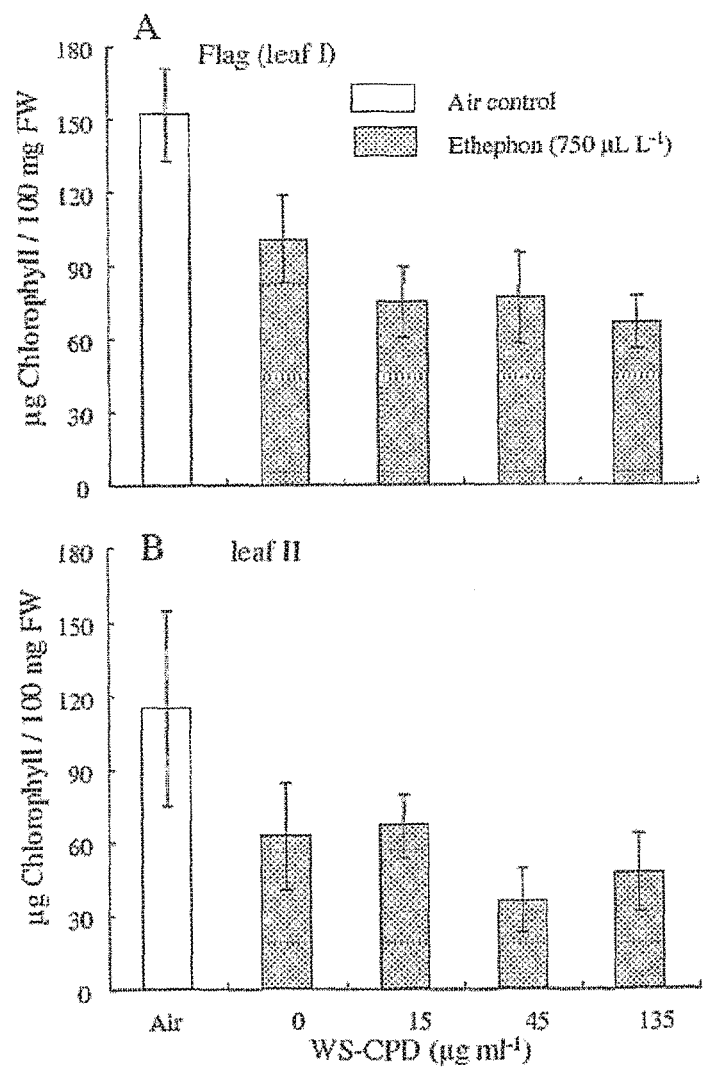
FIG. 43 Effect of pretreatment with WS-CPD (15-415 µg mL$^{-1}$) at milky stage II of the spike followed by Ethephon™ (750 µL L$^{-1}$) treatment on the chlorophyll content of the leaf I and II.
Figure 44:
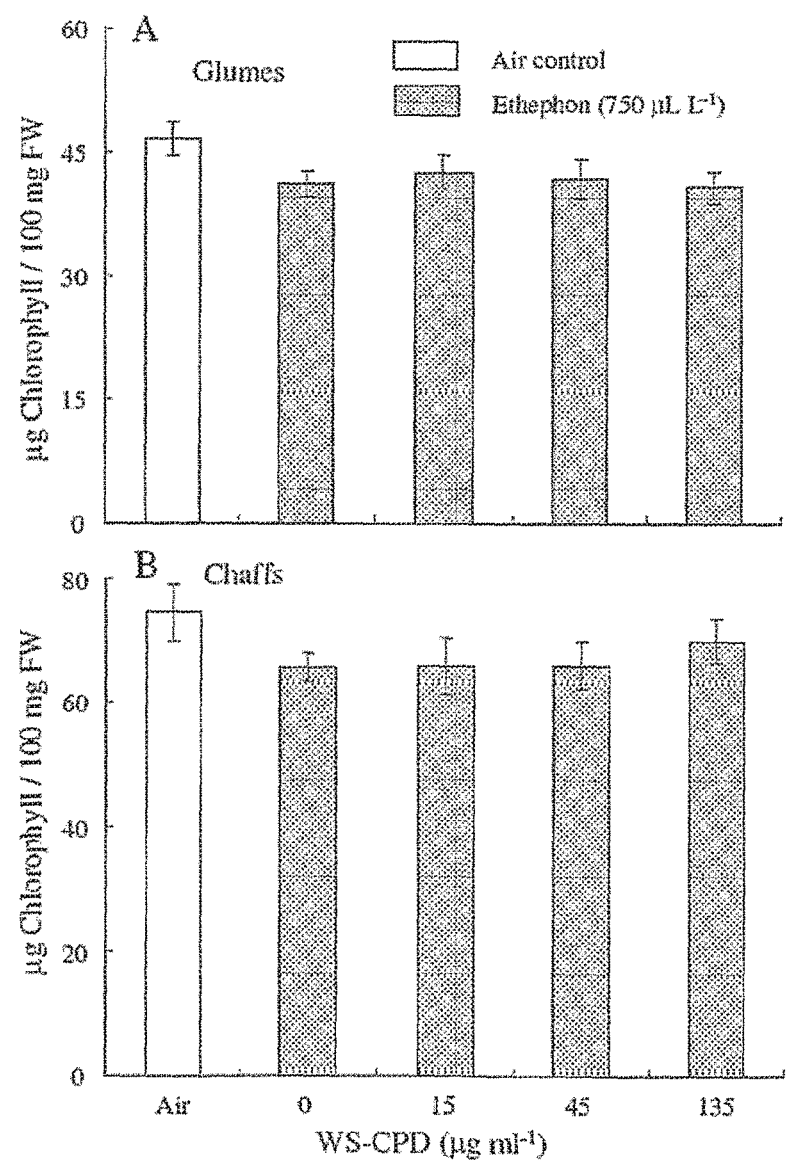
FIG. 44 Effect of pretreatment with WS-CPD (15-415 µg mL$^{-1}$) at milky stage II of the spike, followed by Ethephon™ (750 µl, L$^{-1}$) treatment on chlorophyll content of the glumes and chaffs.

The grains were still soft at the milky stage II, 7 months after germination, when they reached their final size. At this stage the chlorophyll content in untreated leaves declined by about 50% (FIG. 43), and the leaves became more sensitive to Ethephon™ (750 µL L$^{-1}$) reduced the content of chlorophyll by 33 and 47% in the flag leaf and leaf II, respectively (FIG. 43). The sensitivity of the glumes and the chaffs to Ethephon™ (750 µL L$^{-1}$) in terms of chlorophyll degradation was much smaller than that of leaves, only 12% lower compared with the untreated control spikes. Pretreatment spray of the plants with WS-CPD (15 to 135 µg L$^{-1}$), that was expected to reduce the titer of chlorophyll in the treated leaves with Ethephon™ (750 µL L$^{-1}$), was not effective (FIG. 43). It caused only an insignificant decrease of 3% in the chlorophyll titer in the treated spike-chaffs (FIG. 43).

Grain (Dry Seed) Weight at the Milky Stages

Figure 45:
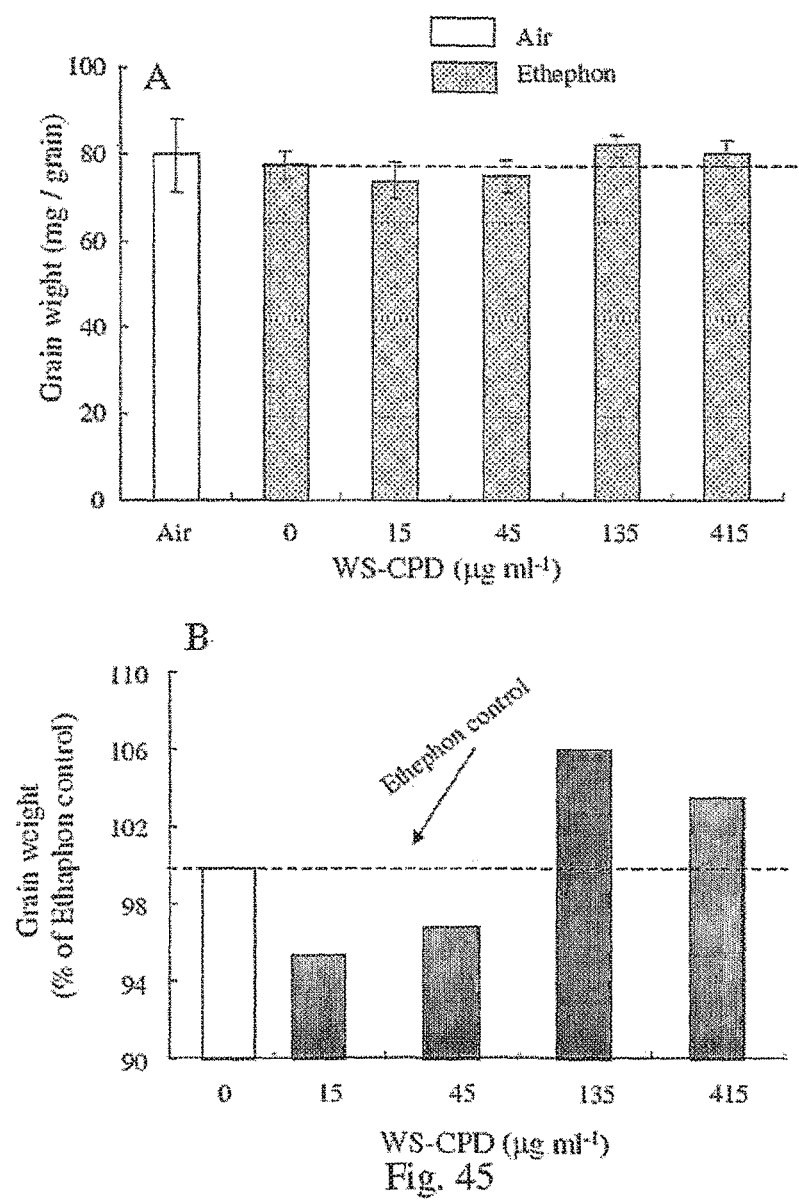
FIG. 45 Effect of pretreatment with WS-CPD (15-415 µg mL$^{-1}$) at the milky stage I of the spike, followed by Ethephon™ (750 µL L$^{-1}$) treatment on grain weight (A) in mg and (B) as percentage of ethylene alone.
Figure 46:
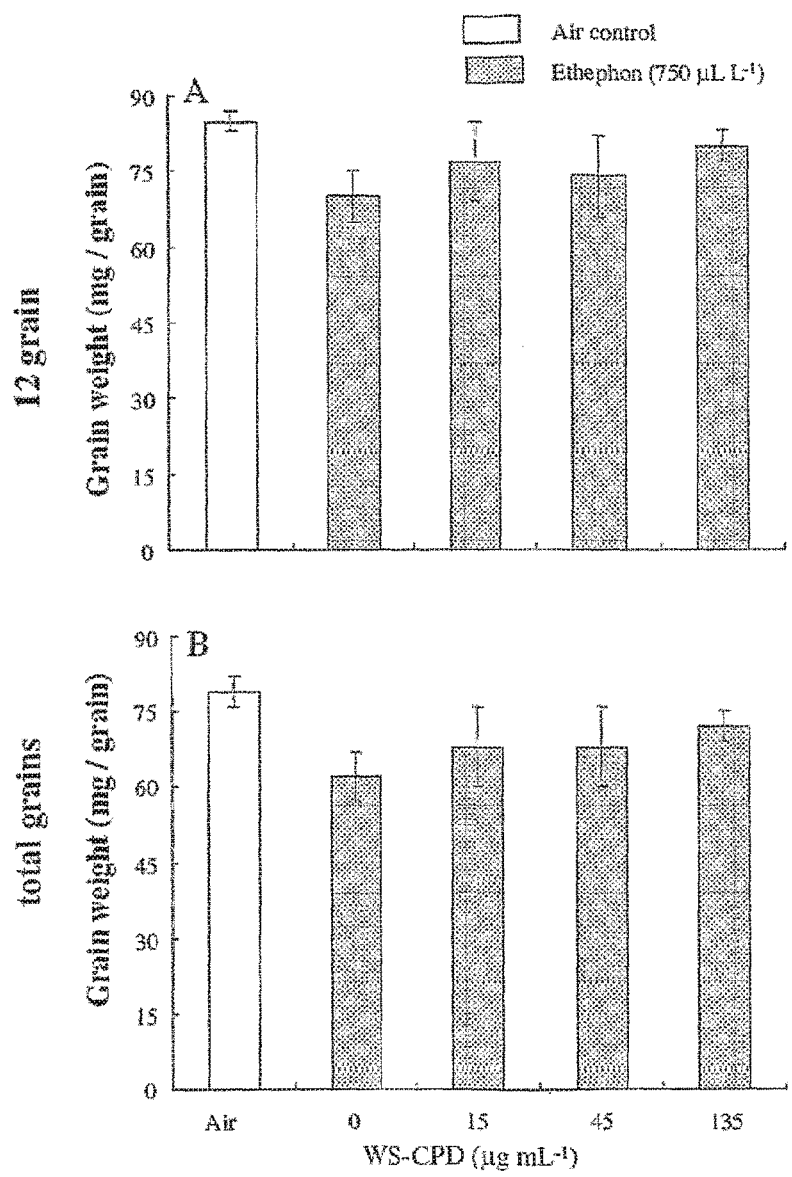
FIG. 46 Effect of pretreatment with WS-CPD (15-135 µg mL$^{-1}$) following Ethephon™ (750 µl L$^{-1}$) treatment on (A) the average weight (mg) of the 15 largest grains and (B) the average weight (mg) spike yield at milky stage II of wheat plants grown in sandy soil.

The fresh weight of the grains (grown on sandy soil) in both milky stages I and II, 6 to 7 months after germination, was similar, reaching 80 mg/grain FW. Ethephon™ (750 µL L$^{-1}$) reduced grain weight by 4% (stage I) and 18% (stage II) (FIGS. 45 and 46, respectively). Pretreatment with WS-CPD at milky stage I (135 µg mL$^{-1}$), which significantly antagonized the Ethephon™-induced degradation of chlorophyll in leaves (FIG. 41), prevented the decrease of Ethephon™-induced grain weight in both milky stages (FIGS. 45 to 47).

Figure 47:
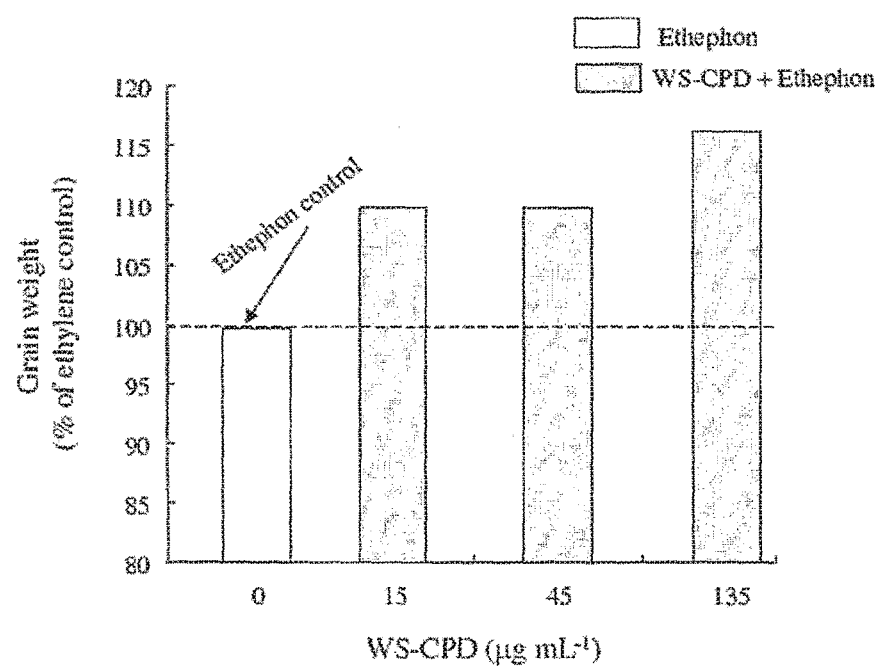
FIG. 47 Effect of pretreatment with WS-CPD (15-135 µg mL$^{-1}$) at the milky stage I of the spike, following Ethephon™ (750 µl L$^{-1}$) treatment on the weight of spike grains (as percent of ethylene alone)
Figure 48:
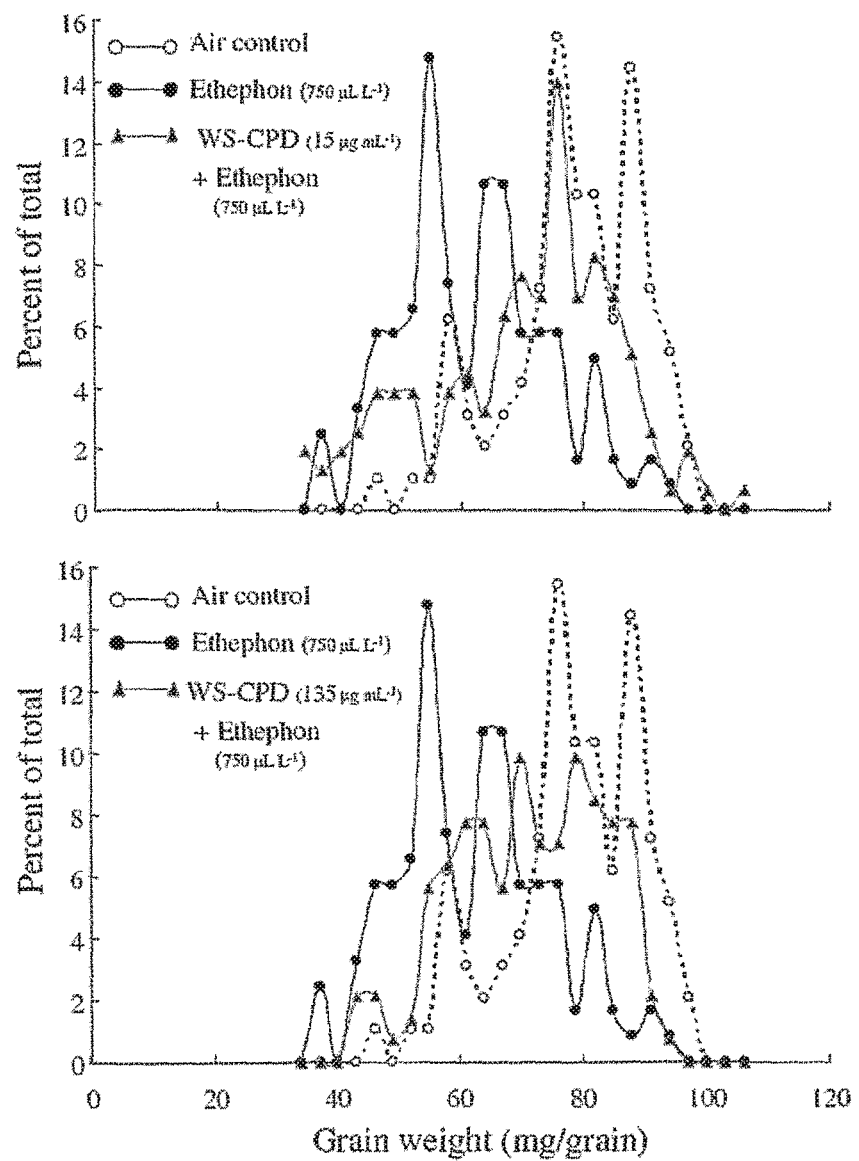
FIG. 48 Effect of one pretreatment spray with WS-CPD (45 or 135 µg mL$^{-1}$), at the milky stage II followed by Ethephon™ (750 µL L$^{-1}$), on the distribution of grain weight (percent of total spike grain yield)

From the data presented in FIGS. 45 to 47, which express the grain weight on a fresh weight basis, it is clear that by antagonizing of the effect of Ethephon™ by WS-CPD at milky stages I and II, the grain yield increased by ca. 5% and ca. 16%, respectively. The same is evident when calculating the grain weight distribution (as percentage of the total number of spike grains yield), and comparing it with the grain weight distribution from Ethephon™-treated plants. The data shows (FIG. 48) very clearly that a significant increase in grain weight was obtained almost in all grain sizes, and was very close to that of air control plants.

In accordance with the previous experiments, in which 80 to 180 µg mL$^{-1}$ of WS-CPD gave the best results in terms of overcoming the Ethephon™ reduction in grain weight, the concentration of 120 µg mL$^{-1}$ of WS-CPD was selected for studying its effect on the grain yield of wheat which was grown under natural conditions. The experiment was conducted with wheat plants grown in a greenhouse in sandy soil. The grain weight was determined at harvest, the dry stage. After spike heading, individual groups of wheat plants were sprayed once, twice, thrice and four times with WS-CPD (120 µg mL$^{-1}$), at 8 to 10 days intervals between treatments, starting at milky stage I.

Figure 49:
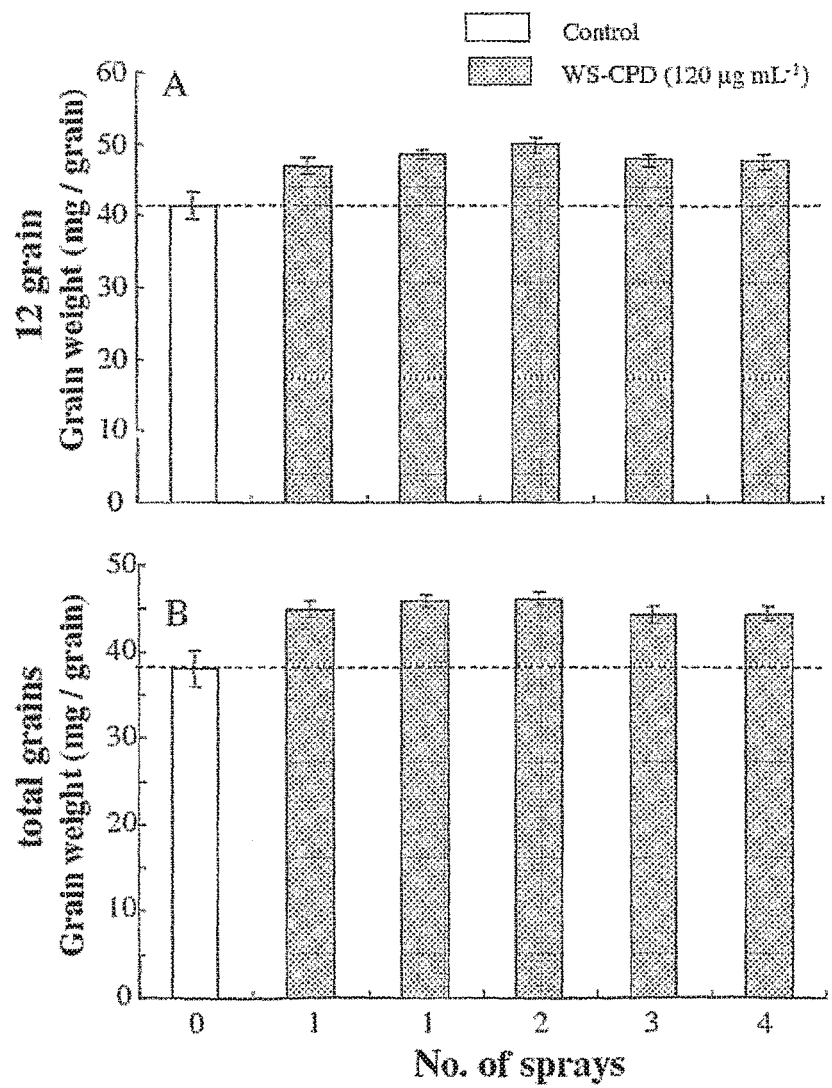
FIG. 49 Effect of the number of WS-CPD (120 µg mL$^{-1}$) sprays on (A) the average weight (mg) of the 15 largest grains and (B) the average weight (mg) spike grain yield at the mature (dry) stage of wheat plants grown in sandy soil.
Figure 50:
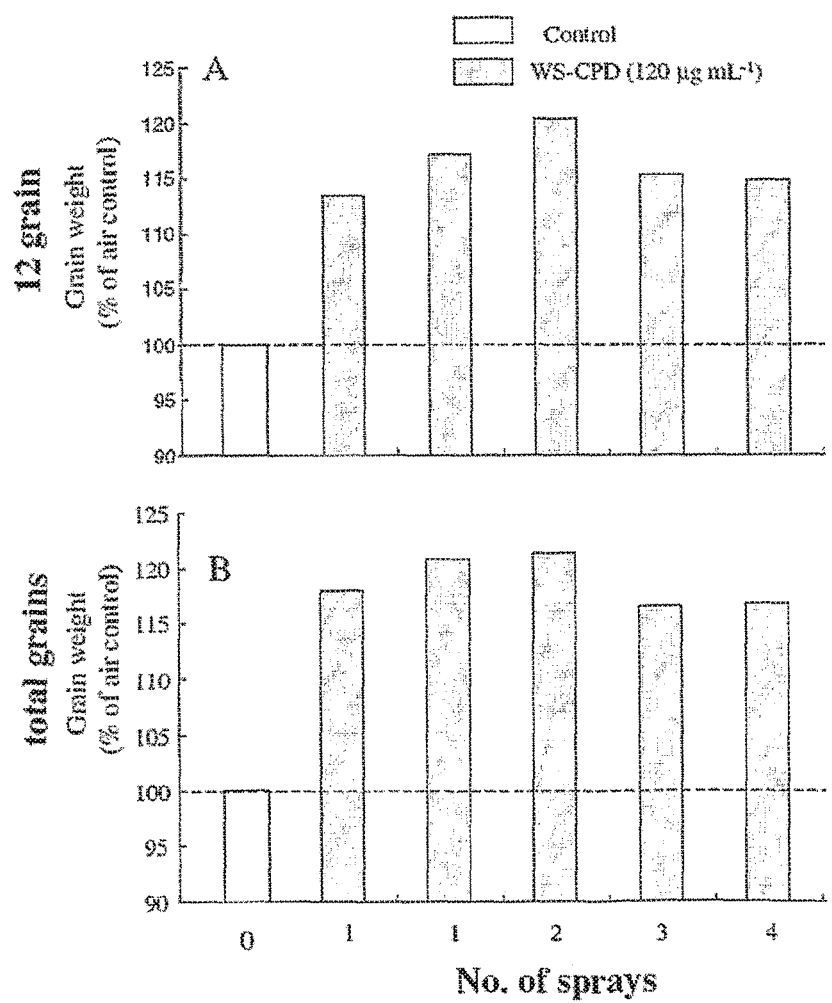
FIG. 50 Effect of number of WS-CPD (120 µg mL$^{-1}$) sprays on (A) the average weight (mg) of the 15 largest spike grains (as percent of untreated wheat plants) and (B) the average weight of all spike grain yield (as percent of ethylene alone), at the mature (dry) stage of wheat plants grown in sandy soil.

At harvest time, as the wheat spike dried (7 months after germination), the grain weight decreased by ca. 50%, and their final dry weight was 38-41 mg/grain (FIG. 49). It was found that even after only one spray of WS-CPD at milky stage I, the total yield increased by ca. 18% (FIG. 50B), and when treated in stage II, one month later, the yield increased after one spray by ca. 20%. There was no advantage to repeating sprays after stage II (FIG. 50B), and no difference in the above response between the average weight of 15 biggest grains and the average weight of all spike grains as compared to the control (compare FIG. 50A to FIG. 50B).

Figure 51:
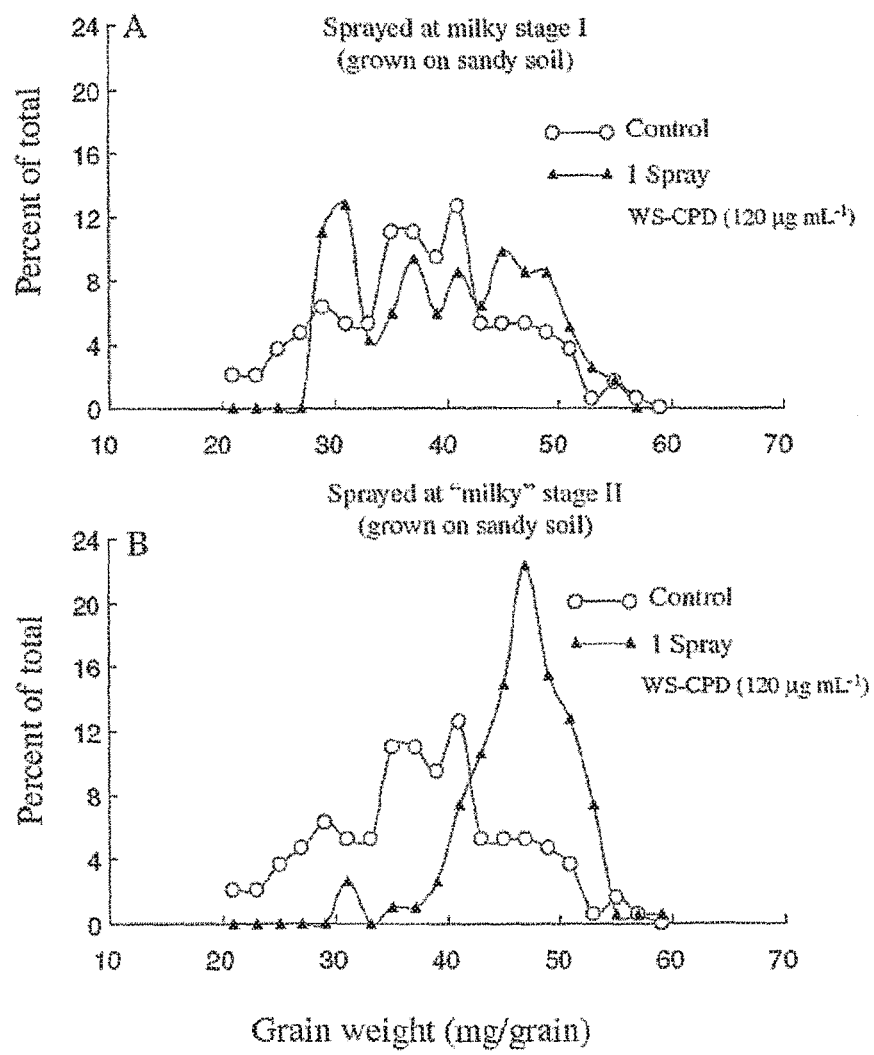
FIG. 51 Effect of one spray of WS-CPD (120 µg mL$^{-1}$) at (A) milky stage I and (B) milky stage II, on the distribution of grain weight (percent of total spike grain yield), from wheat plants grown in sandy soil.
Figure 52:
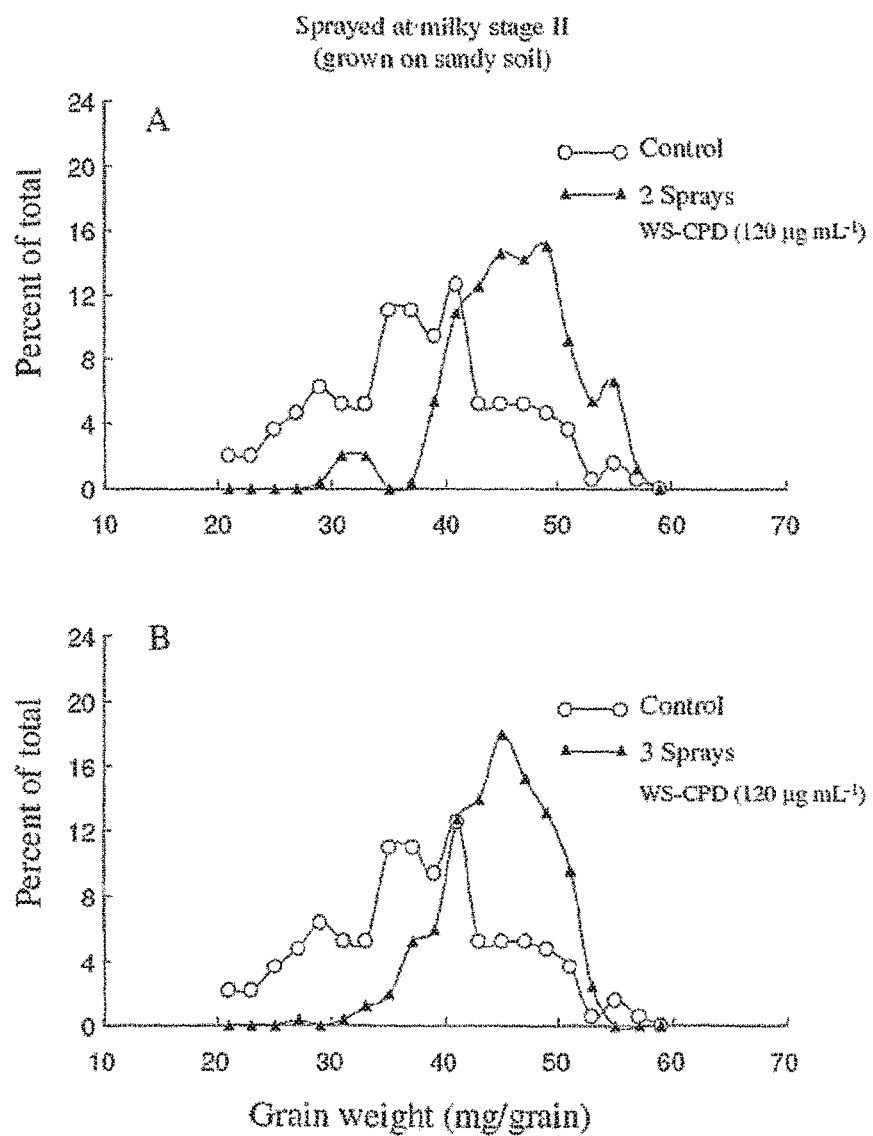
FIG. 52 Effect sprays with WS-CPD (120 µg mL$^{-1}$) at milky stage II on the distribution of grain weight (percent of total spike grain yield) (A) 2 sprays and (B) 3 sprays. Plants were grown in sandy soil.
Figure 53:
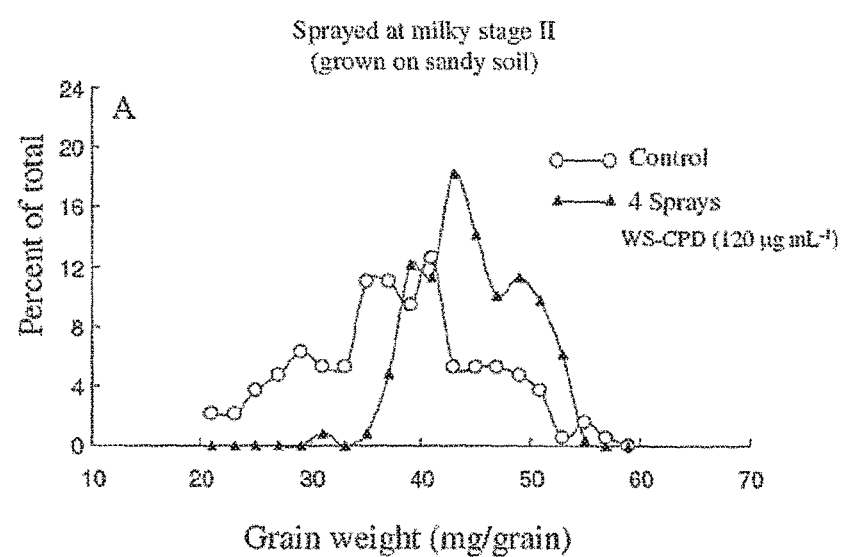
FIG. 53 Effect of 4 sprays of WS-CPD (120 µg mL$^{-1}$) at milky stage II, on distribution of grain weight (percent of total spike grain yield). Plants were grown in sandy soil.

The 20% increase in the weight of the dry grain (i.e., yield), and specially after one spray of WS-CPD at milky stage II, is also evident when calculating the distribution of grain weight (as percent from total number of grains) according to their individual weight (mg/grain), as compared to grain weight distribution of control plants. The data show very clearly that the significant increase in grain weight was obtained in almost in all grain sizes (FIGS. 51 to 53). There were almost no grains weighting less than 35 mg/grain in the spikes of the treated plants, while in the spikes of the untreated plants more than 30% of the grains were below this weight (FIG. 51 to 53).

Figure 54:
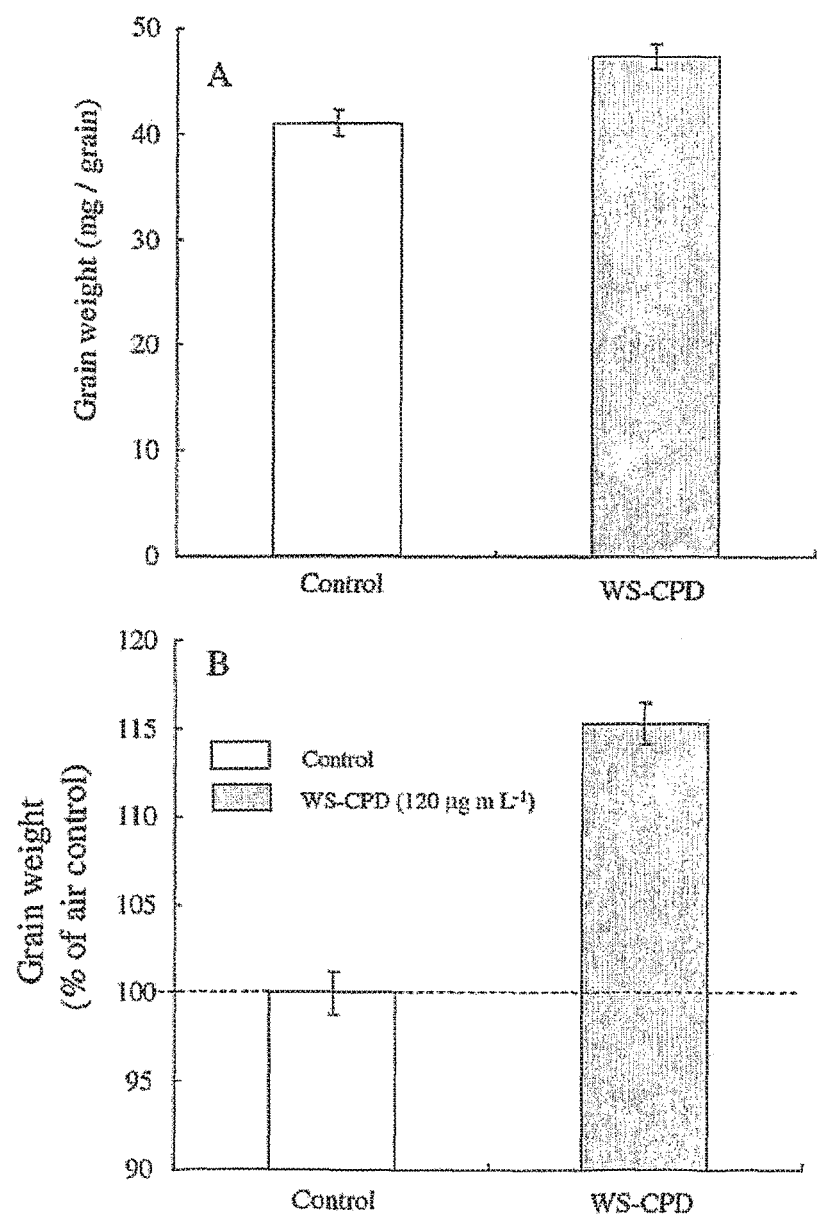
FIG. 54 Effect of one spray with WS-CPD (120 µg mL$^{-1}$) at milky stage II of the spike grain, on average grain weight (A) in mg and (B) as percent of untreated wheat plants. Wheat plants were grown in 450 mL pots, in peat-based medium.
Figure 55:
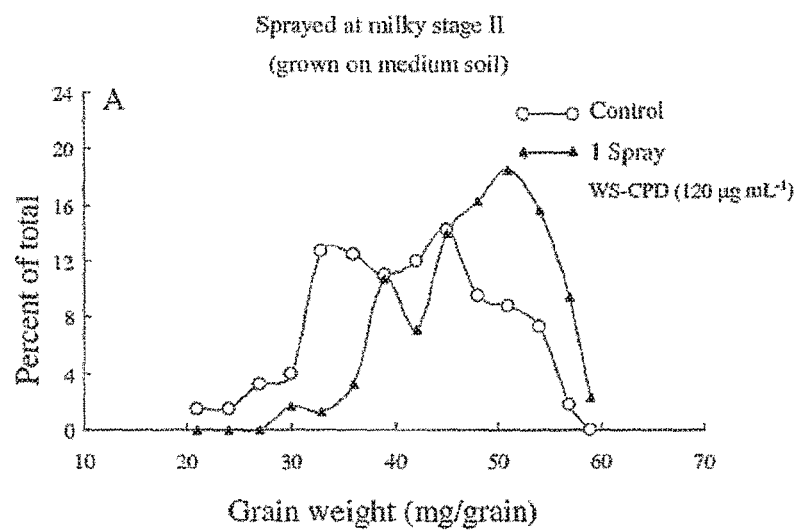
FIG. 55 Effect of one pretreatment spray of WS-CPD (120 µg mL$^{-1}$) at milky stage II, on distribution of grain weight (percent of total spike grain yield). Wheat plants were grown in 450 mL pots, in peat-based medium.

In another experiment the wheat plants were grown in 450 ml pots in a peat-based medium. The plants were sprayed once with WS-CPD (120 µl L$^{-1}$) at milky stage II, 7 months after germination. The results confirmed previous results, showing a −15% increase in grain yield over the weight of the grains of untreated control plants (FIG. 54). This is also evident when calculating the distribution of grain weight (as percentage of the total number of grains) and comparing them with grain weight distribution from control plants. The data shows very clearly that a significant increase in grain weight was again obtained in all grain sizes (FIG. 55).

WS-CPD Characteristics

WS-CPD has the molecular structure given by formula I. Its structure was confirmed by NMR spectroscopy and negative ion mass spectrometry.

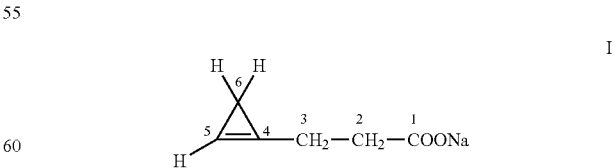

Figure 56:
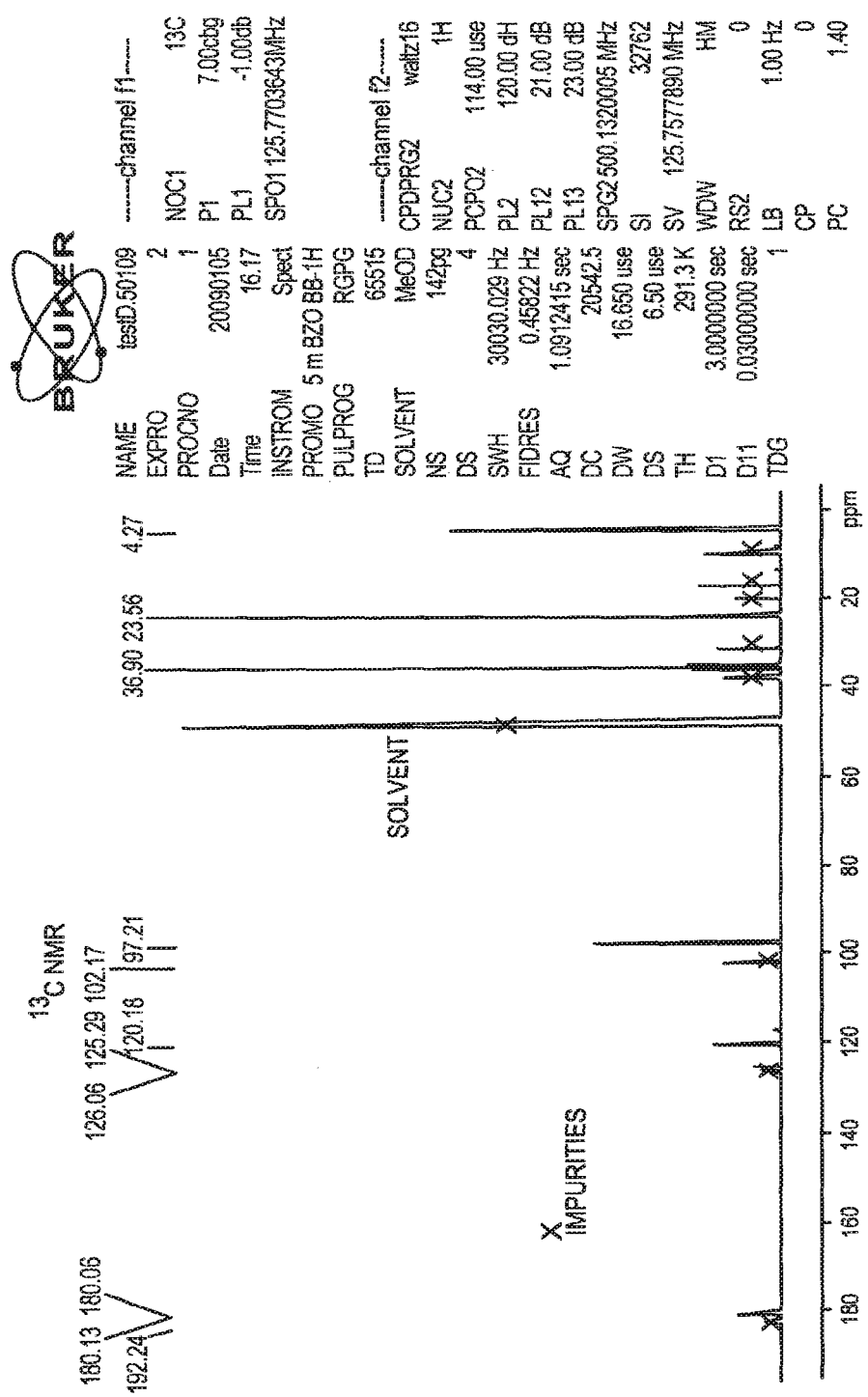
FIG. 56 The $^{13}$C NMR spectra of WS-CPD.
Figure 57:
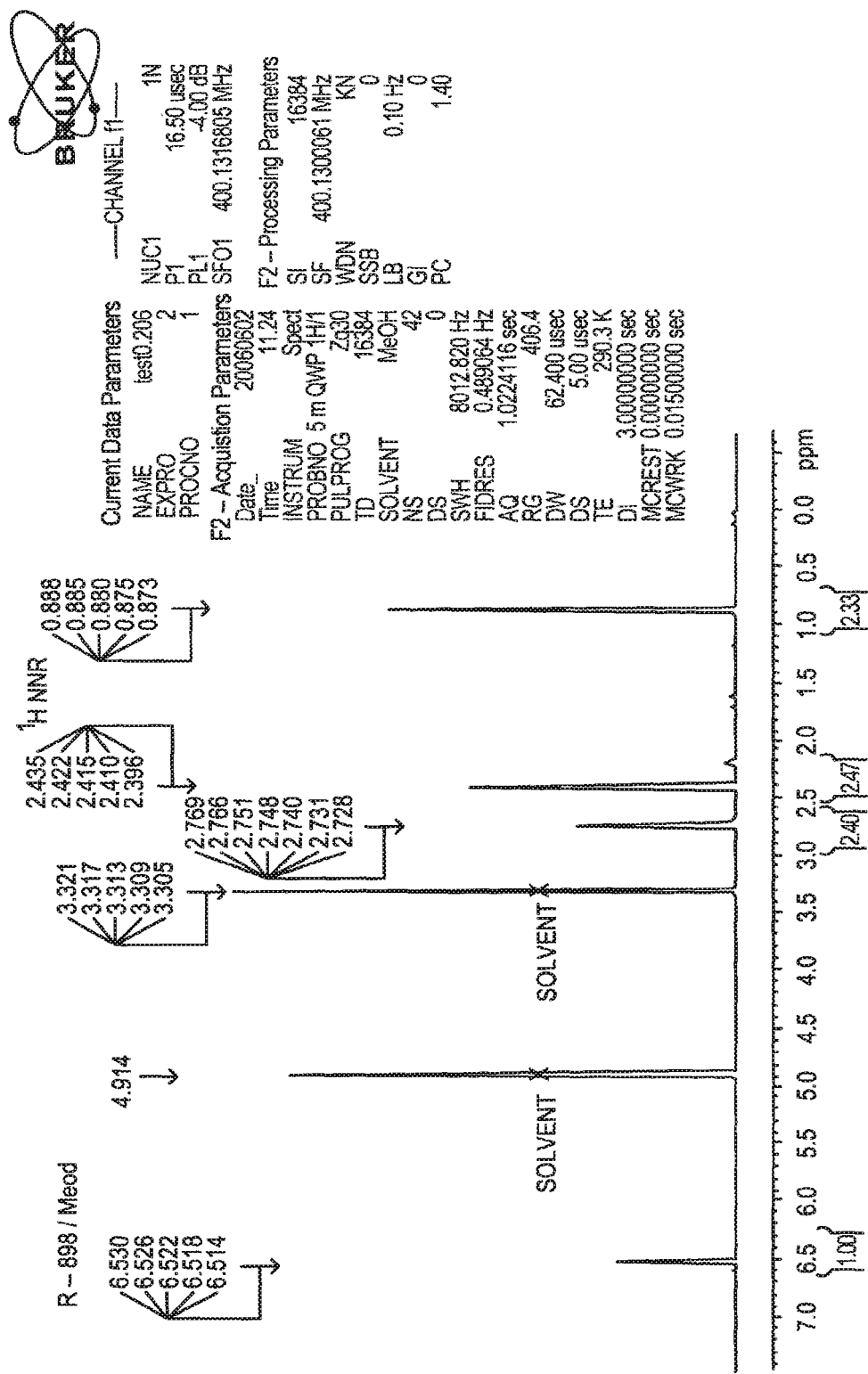
FIG. 57 The $^{1}$H NMR spectra of WS-CPD.
Figure 58:
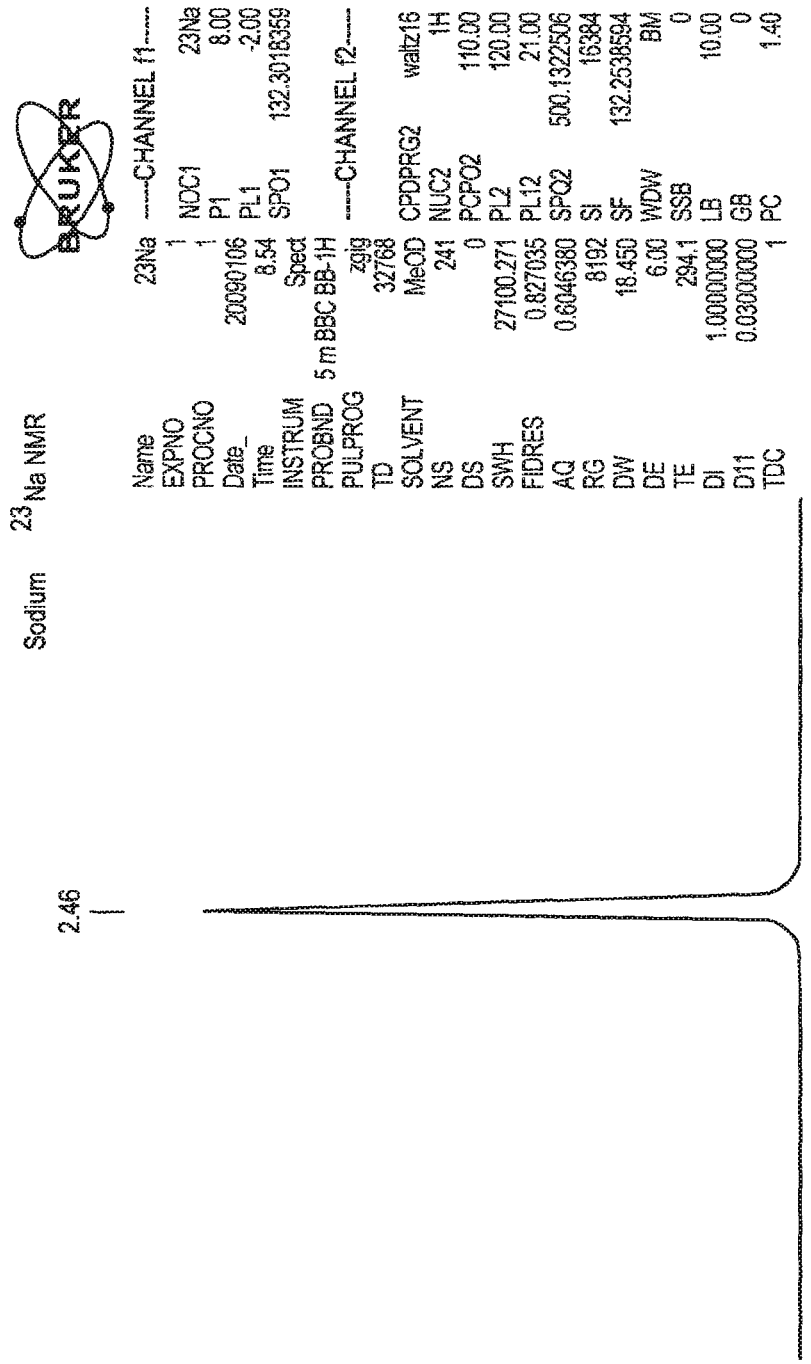
FIG. 58 The $^{23}$Na NMR spectrum of WS-CPD.

The $^{13}C\{^1H\}$, $^1H$, and $^{23}Na\{^1H\}$-NMR spectra of WS-CPD in methanol are presented in FIGS. 56-58. The six peaks in the $^{13}C\{^1H\}$ NMR spectrum of WS-CPD are assigned as follows: δ$_C$ 4.27 (C6), 23.58 (C2), 34.90 (C3), 97.21 (C5), 120.18 (C4), and 180.06 (C1). Four peaks are found in the $^1H$ NMR (FIG. 57). The peak positions ($\delta_H$), splittings, and assignments are as follows: 0.88 (s, 2H, C6); 2.42 (t, 2H, C2); 2.75 (t, 2H, C3); and 6.52 (s, 1H, C5). The $^{23}$Na{$^1$H}-NMR spectrum presented in FIG. 58 shows one signal at $\delta_{Na}$ −2.46 ppm, confirming that molecule I has one type of sodium atom.

Figure 59:
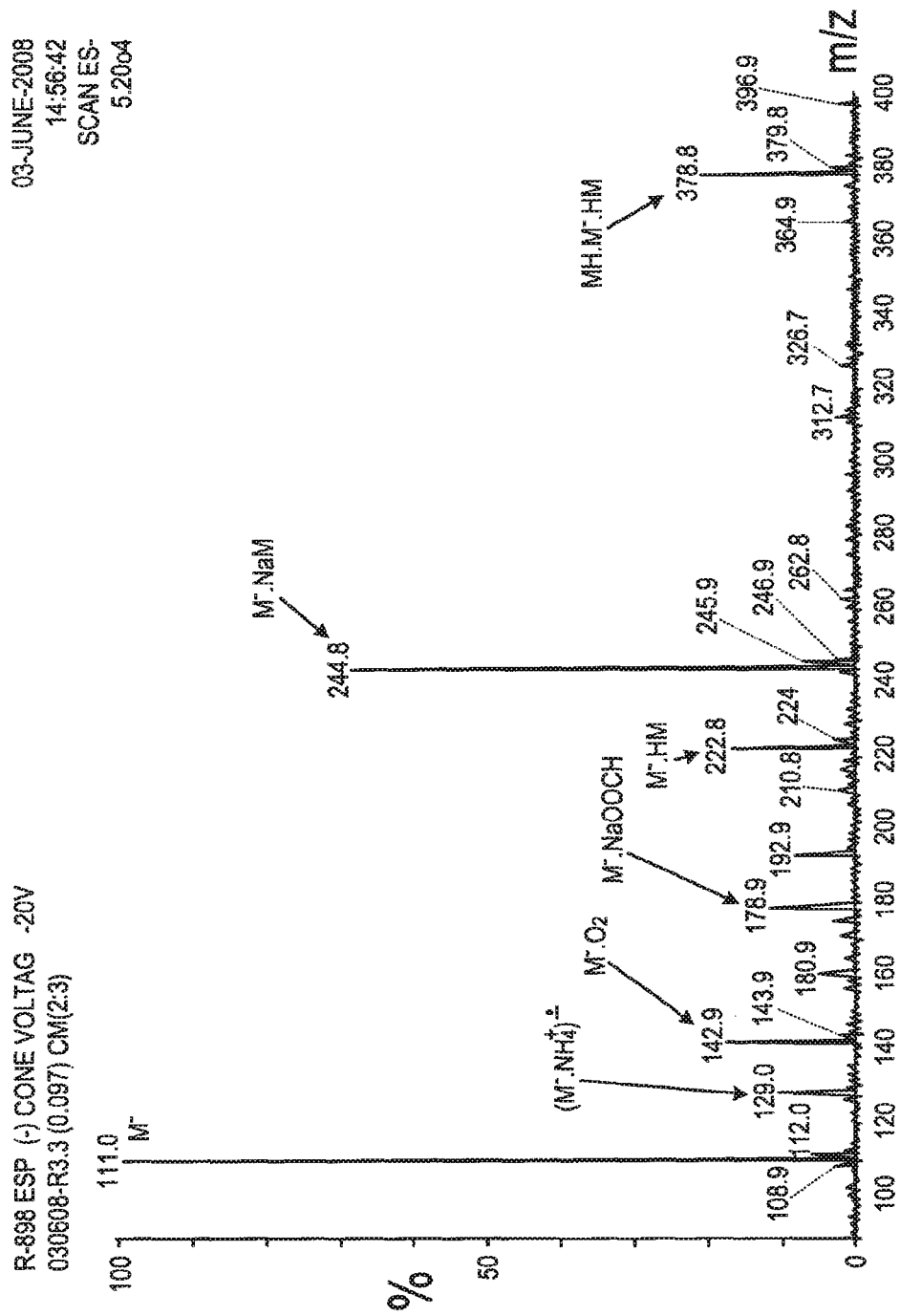
FIG. 59 The mass spectrum of WS-CPD.

The mass spectrum of WS-CPD (negative mode) is presented in FIG. 59. Two primary peaks are observed, one at m/z=111.0 ($C_6H_7O_2^-$), and one at m/z=244.8 ($C_6H_7O_2^-\cdot NaC_6H_7O_2$).

Figure 60:
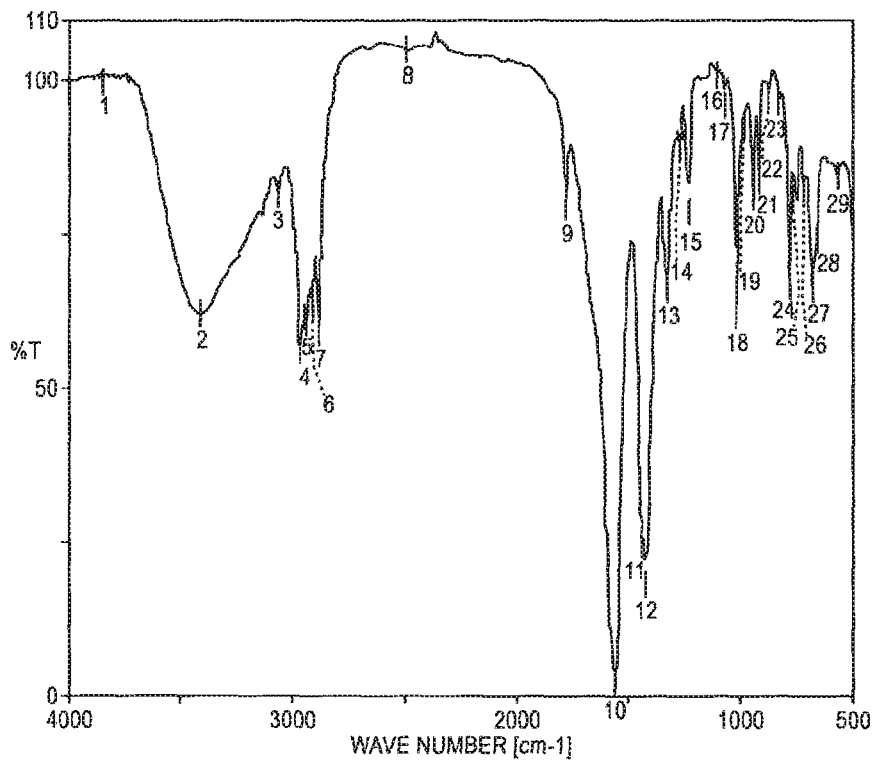
FIG. 60 The IR spectra of WS-CPD.
Figure 61:
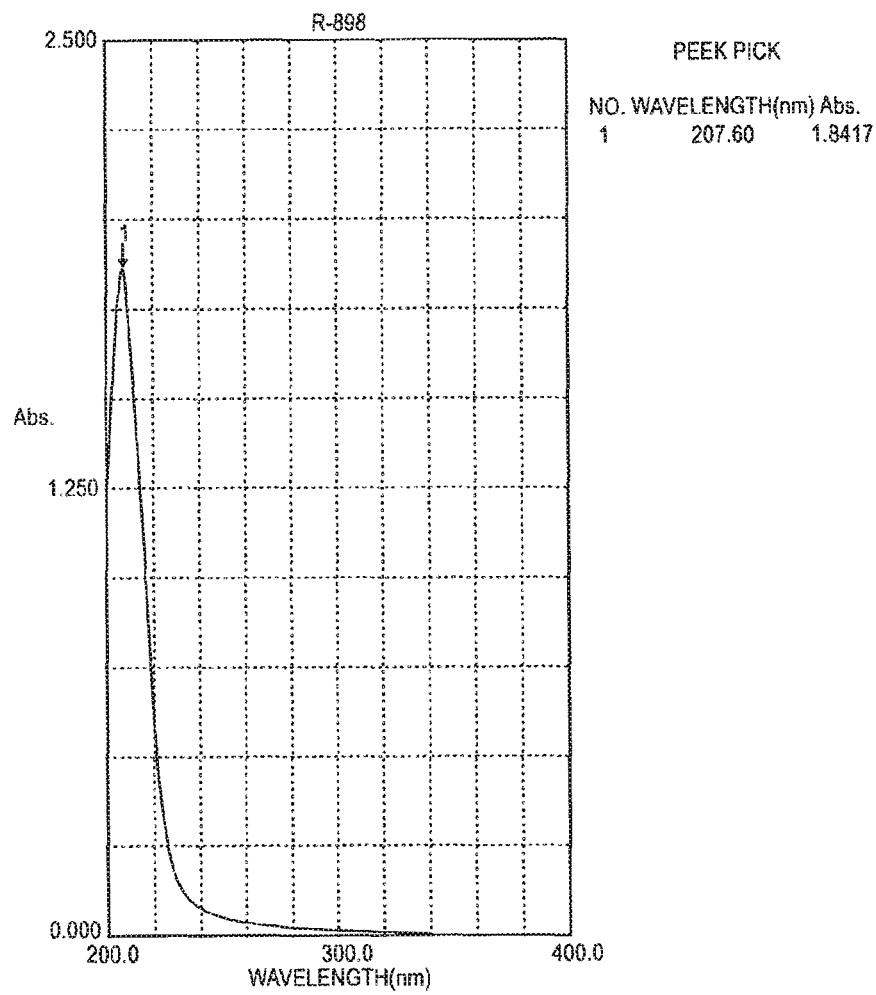
FIG. 61 The UV-Vis spectra of WS-CPD.

The IR spectrum (FIG. 60), UV-VIS spectrum (FIG. 61), and potentiometric titration (FIG. 62) are all consistent with the structure given above for WS-CPD. The IR peak of WS-CPD at $C_1$=1773 cm$^{-1}$, and the peak of the C=O stretch in the IR and the UV-VIS peak is $\lambda_{max}$ 206$_{nm}$.

Figure 63:
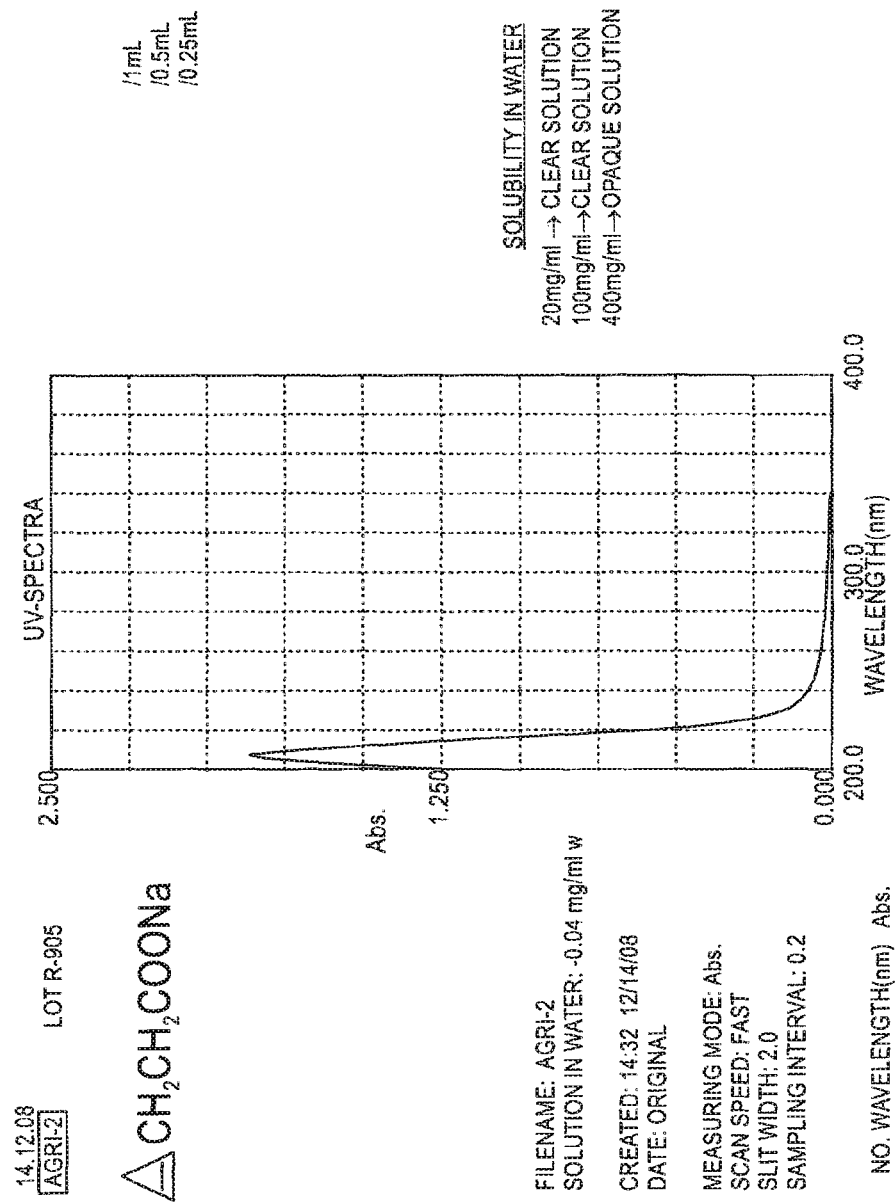
FIG. 63 Complete (up to 400 mg/ml or more) dissolution of WS-CPD in water at 25° C.

WS-CPD is highly soluble in water at 25° C. (≥400 mg mL$^{-1}$), FIG. 63. Upon heating, decomposition without melting occurs, beginning at 265-270° C. The HPLC trace shown in FIG. 64 further demonstrates that WS-CPD is produced as a single pure substance.

Figure 65:
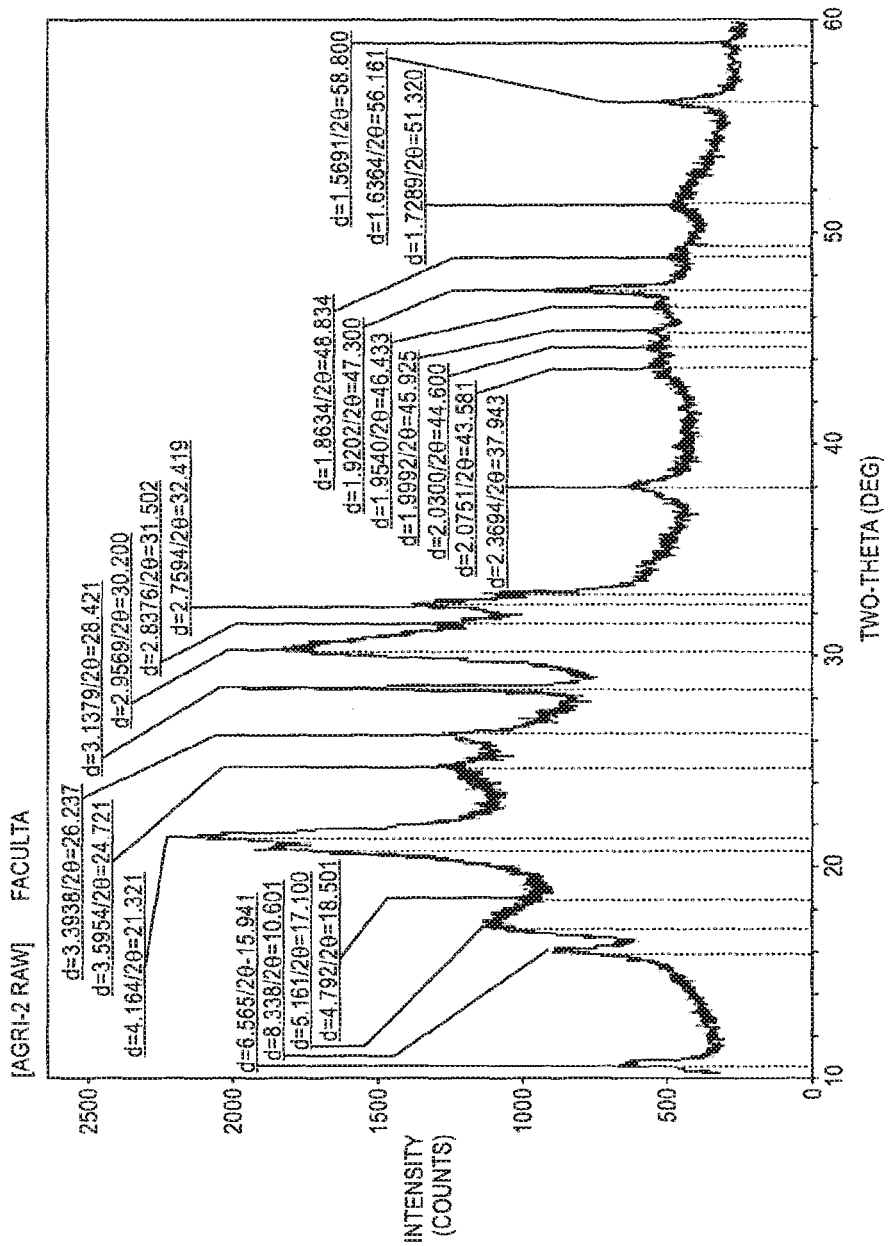
FIG. 65 The XRD diffraction pattern of WS-CPD.

At ambient temperature, the $pK_a$ of WS-CPD is greater than 4.5. Thus, under the normal conditions of use, e.g., pH 7.6-7.8, more than 99% of the compound is present in the anion form. Reference is now made to FIG. 65, which shows the XRD pattern of WS-CPD powder ground by a mortar and pestle and placed in a shallow depression in a background-free silicon disc. The XRD pattern was obtained in a Rigaku Ultima sealed tube theta-theta diffractometer operating at a power level of 1.6 kW, with a step size of 0.02°, angular range of 10-60°, and speed of 0.5°/min. Analysis of the XRD pattern was performed using the Jade 8 program (MDI, Inc.). From the diffraction pattern, it appears that the powdered material is not homogeneous, but rather that there appear to be three distinct structural forms present, namely, an amorphous form, a poor quality crystalline form, and a crystalline form. The presence of the amorphous form is indicated by the prominent diffuse peak centered at 2θ~23°. Superimposed on this broad peak are a number of sharp peaks, indicating the presence of a crystalline form. These peaks appear at 2θ=10.6°, 15.94°, 28.42°, 47.3°, and 56.16°. The remaining diffraction peaks, are between 16.5°-19°, 42°-46° are significantly broader than the five sharp peaks, but much narrower than the broad diffuse peak, and indicate the presence of a poor quality crystallite. The effective crystallite sizes of the crystalline form were calculated using the Scherrer formula and found to be in the range of 300-700 Å. The crystallite sizes of the poorly ordered crystalline form are much smaller. Quantitative determination of the relative amounts of the three forms present in the powder shows no impurities. The following volume fractions were measured: amorphous—57.5%; poorly crystalline—39.5%; crystalline—3%. To the extent that a given material has average atomic number higher than the others, its volume fraction would be smaller than that listed here.

Reference is now made to FIG. 66, which presents the Certificate Analysis Form of the chemical analysis of the WS-CPD product. The analysis of WS-CPD was performed by D-Parm Innovative Biopharmaceuticals Ltd, Rehovot, Israel.

The effect of WS-CPD on wheat was further studies in Field tests were. It was found that field experiments confirmed the results obtained in aforementioned greenhouse experiments; in the conditions of those field experiments, the most effective treatment was one spray at the Milky stage I; and that mechanical thresh separation reduced the net yield from about 15±2.6% by about 5 to 6%.

Field Experiments in Wheat

Plant material and experimental design—Winter wheat (*Ttriticum aestivum*, var. Galil) was sown in December 2008 in a medium-heavy soil in the farm of the Volcani Center, Agricultural Research Organization, Bet-Dagan, Israel. Winter rainfall between October and March was 515 mm. The crop was raised without irrigation. The plants were sprayed twice with insecticide in November with 'Tunex' (one L/acre) and in December with 'Oror Turbo' (200 g/acre). The experiment started in mid-March, 2009. Six blocks were randomly selected, and each block was further randomly divided into four treatment plots of two square meters each (FIG. 67A—right and left). Two-meter-wide strips of untreated plants served as border lines between the blocks (FIG. 67A—center). The following treatments were applied: 1. control; 2. spraying WS-CPD at the 'Milky' stage I (30.3.09); 3. spraying WS-CPD at the 'Milky' stage II (17.4.09); 4. two successive WS-CPD sprays as above (30.3.09 and 17.4.09).

Treatments—The treatment solution of WS-CPD contained 120 μg mL$^{-1}$ of WS-CPD in 10 mM K-phosphate buffer (pH 7.6) and 0.1% of 'Kinetic' surfactant. Spraying (about 0.8 L/two square meters) was applied with a portable sprayer (ACL 7-L, Great Brittan). The controls were sprayed with the treatment solution without WS-CPD. The spraying was aimed to cover the upper part of the plants, from the second leaf below the 'Flag leaf' and up, covering the whole spike.

Determination of seed development—In order to follow the dynamics of seed development from 'Milky' stage I to seed maturity, groups of 200 spikes were sampled from the border strips. Samples were taken on 30.3.09 ('Milky' stage I), 17.4.09 ('Milky' stage II), and 19.5.09 (seed maturity). The spikes were brought to the laboratory and dried in an oven (60° C.) until complete dryness. After drying, the seeds were separated from each spike, counted, and their weight was recorded to determine the average seed weight for each spike. The number of spikes with the same average seed weight of each treatment was expressed as percent of total spike number.

Harvesting—At the termination of the experiment (19.5.09), when the seeds reached full maturity, the spikes from all six blocks were harvested, counted, and placed on tables in the greenhouse for 12 days to reach complete dryness (FIG. 67B).

Hand seed separation—One hundred dried spikes were randomly sampled of each plot (n=6) after harvesting. The seeds of each spike were separated (FIGS. 67C and D) and counted and their weight was determined. The seed weight of each spike was divided by the number of seeds per spike to determine the average seed weight of each spike. The number of spikes of each treatment with the same average seed weight was expressed as percent of total spike number.

Mechanical thresh seed separation—The remaining dry spikes of each experimental plot were counted and mechanically thresh separated (Kurt Pelz Co., Germany) from their glumes and chafes, and their dry weight was recorded (g/plot). For comparison of the yield weight of the controls between mechanical thresh and hand separation, 200 seeds from each method were randomly sampled.

Determination of seed development—The distribution of seed weight, after hand separation from the spikes, of untreated plants during natural maturation (FIG. 68) showed a significant increase of weight in all seed sizes between 'Milky' stages I and II and between 'Milky' stage II and maturity. The average seed weight increased by 41% between 'Milky' stages I and II; and by 29% between 'Milky' stage II and maturity.

Figure 69:
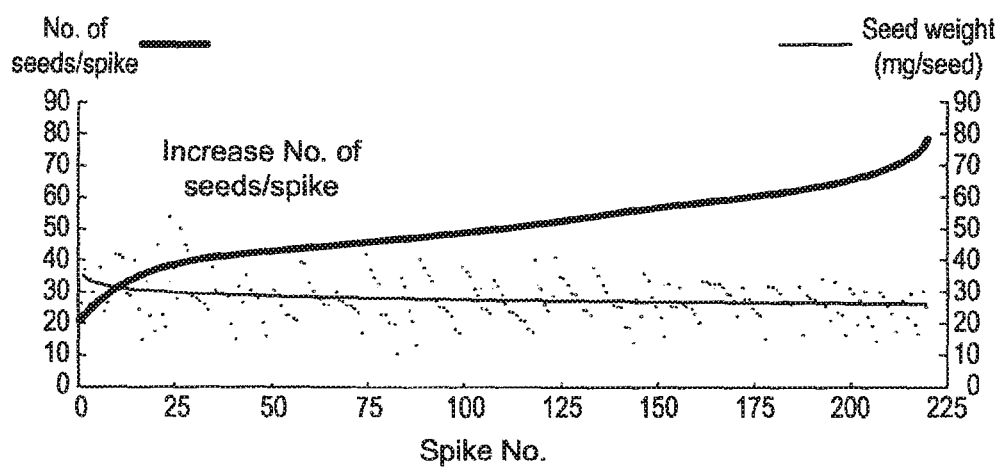
FIG. 69 Relation between increasing average seed number/spike and seed weight.
Figure 70:
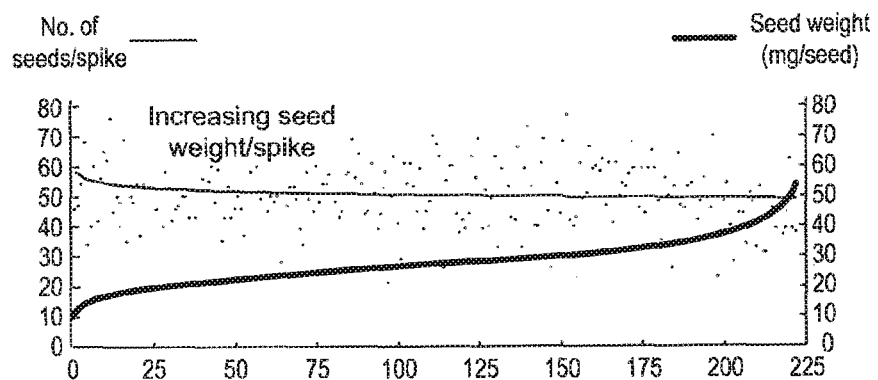
FIG. 70 Relationship between increasing average seed weight/spike and seed number.

Seed weight and number per spike—The relation between number of seeds (number of seeds/spike) and seed weight (mg/seed/spike) in untreated plots with 220 spikes that were harvested at random from untreated plants, as recorded at 'Milky stage II, showed that while the number of seeds/spike increased by about 3.75 fold (when calculating the lowest numbers of seeds/spike in relation to the highest number of seeds/spike), while the average weight of seeds/spike changed only by about 1.5 fold (FIG. 69). This relationship was also well expressed when testing the relationship between the increase in the average seed weight/spike and the number of seeds/spike. The data showed clearly that a significant increase in the number of seeds was not concomitantly related with a significant decrease of seed weight (FIG. 70).

Figure 67:
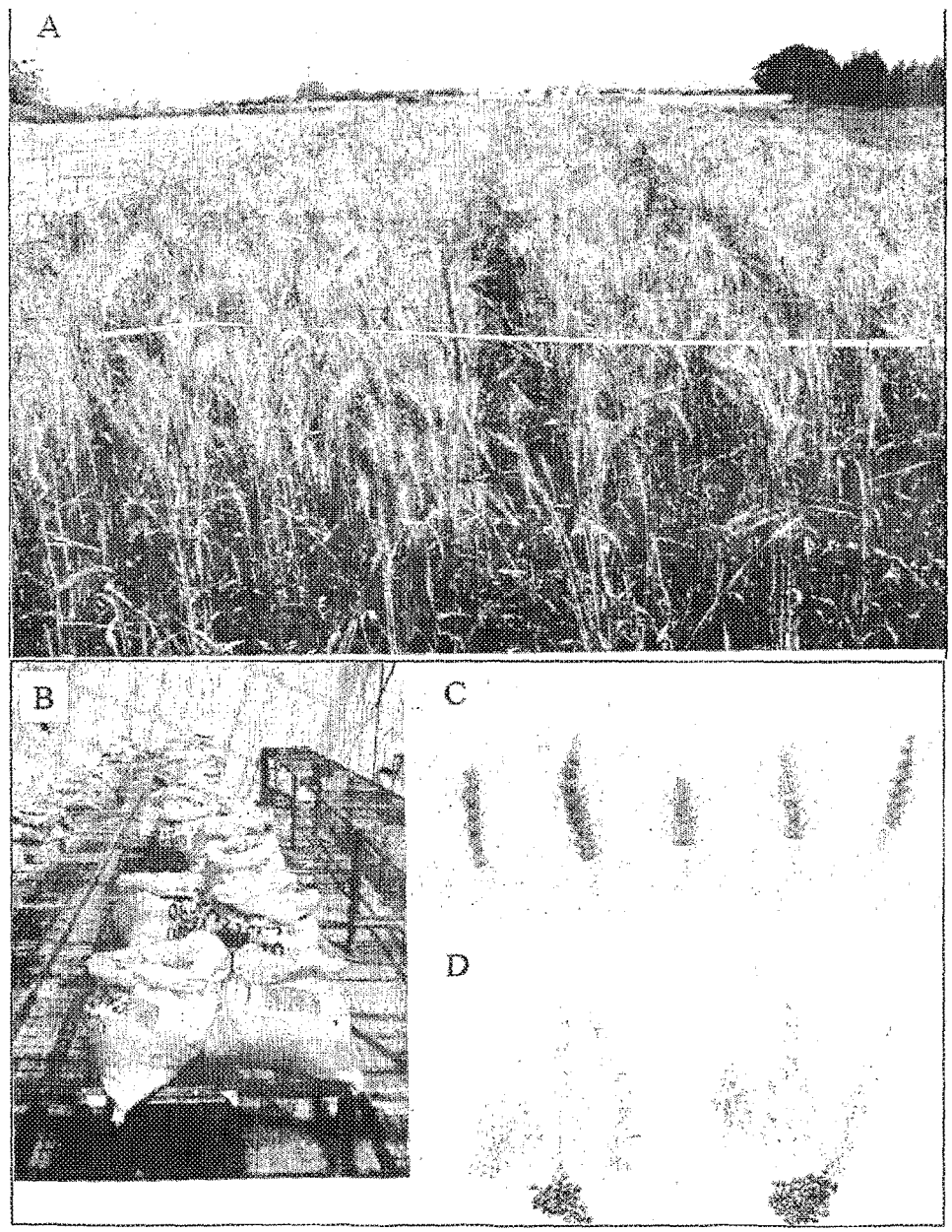
FIG. 67 Experiment design and data collection.

Reference is now made to FIG. 67, presenting the experiment design and data collection: A. Six blocks were randomly selected, and each block was further randomly divided in to four treatment plots of two square meters each (right and left). Two meter wide strips served as border lines between the blocks (center); B. Each replicate (plot) was collected separately, counted, and spread on tables in the greenhouse for 12 days to reach complete dryness; C. Individual spikes ready for hand seed separation; and D. separation of the seeds from the spikes, glumes, and chaffs.

Figure 68:
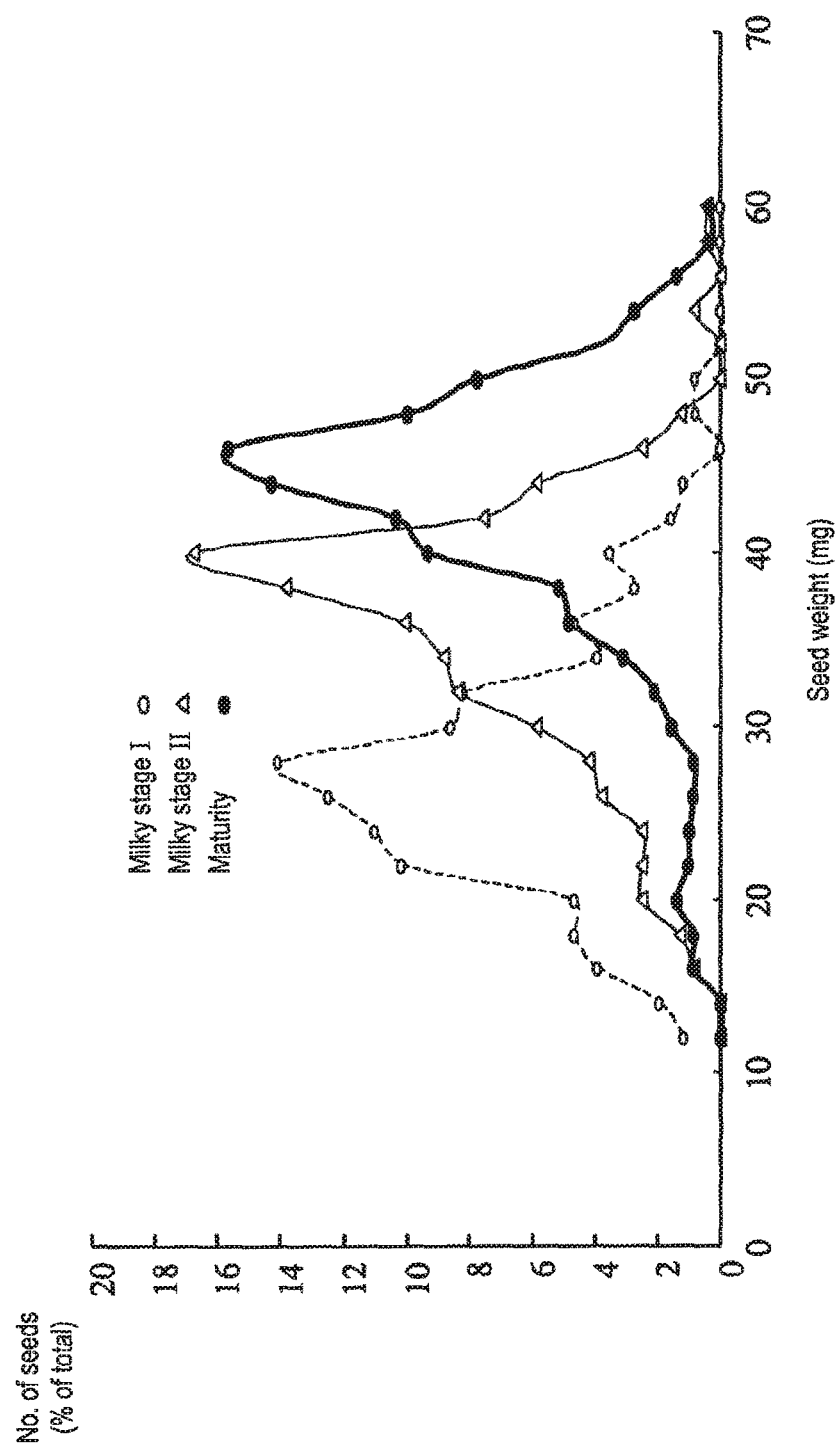
FIG. 68 Dynamics of seed development from 'Milky' stage I to maturity.

Reference is now-made to FIG. 68, presenting the dynamics of seed development from 'Milky' stage I to maturity. The numbers of seeds of 200 spikes of each developmental stage with the same average seed weight (mg/seed) were counted and presented as percent of the number of total spikes.

Reference is now made to FIG. 69, presenting the relation between increasing average seed number/spike and seed weight. The relationship between increasing seeds number per spike and seed weight (mg/seed), as recorded at 'Milky stage II in untreated plots.

Reference is now made to FIG. 70, presenting the relationship between increasing average seed weight/spike and seed number. The relationship between increasing average seed weight per spike and its seed number, as recorded at 'Milky stage II in untreated plots.

Figure 71:
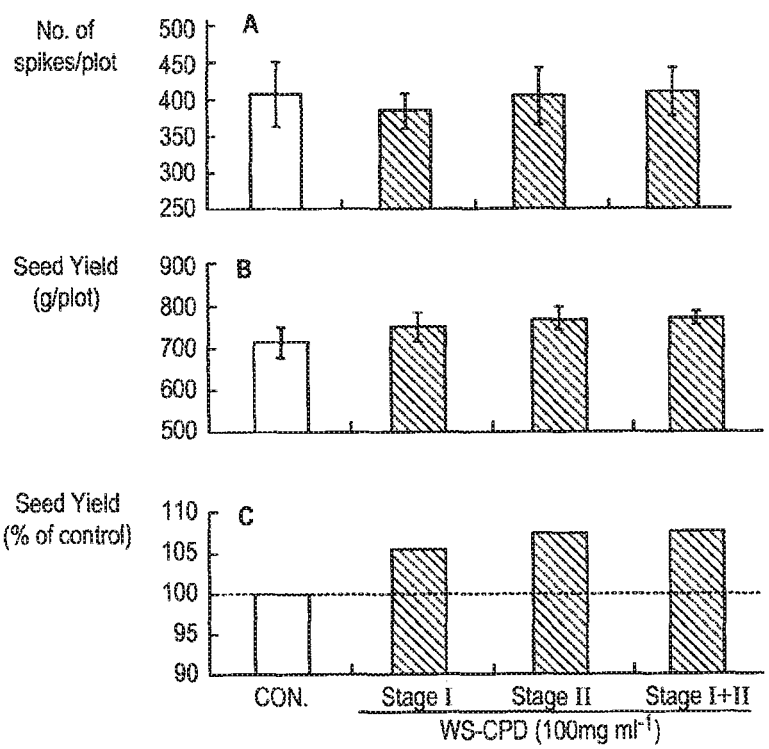
FIG. 71 Effect of WS-CPD on mechanically thresh-separated seed yield (g/plot)

Reference is now made to FIG. 71 presenting the effect of WS-CPD on mechanically thresh-separated seed yield (g/plot). After spiking, plants were randomly divided into six blocks, and plants were sprayed with WS-CPD (120 mg mL$^{-1}$; K-phosphate buffer, pH 7.6, 10 mM; 'Kinetic', 0.1%) at two seed development stages: a. 'Milky' stage I (30.3.09); b. and 'Milky' stage II (17.4.09); and c. at milky stages I and II (30.3.09 and 17.4.09). The controls were sprayed with the treatment solution without WS-CPD. (A) Total number of spikes, per plot, were counted at harvest. (B) Seed weight per plot of mechanical thresh separated seeds. (C) Yield of WS-CPD-treated plants presented as percent of control.

Figure 72:
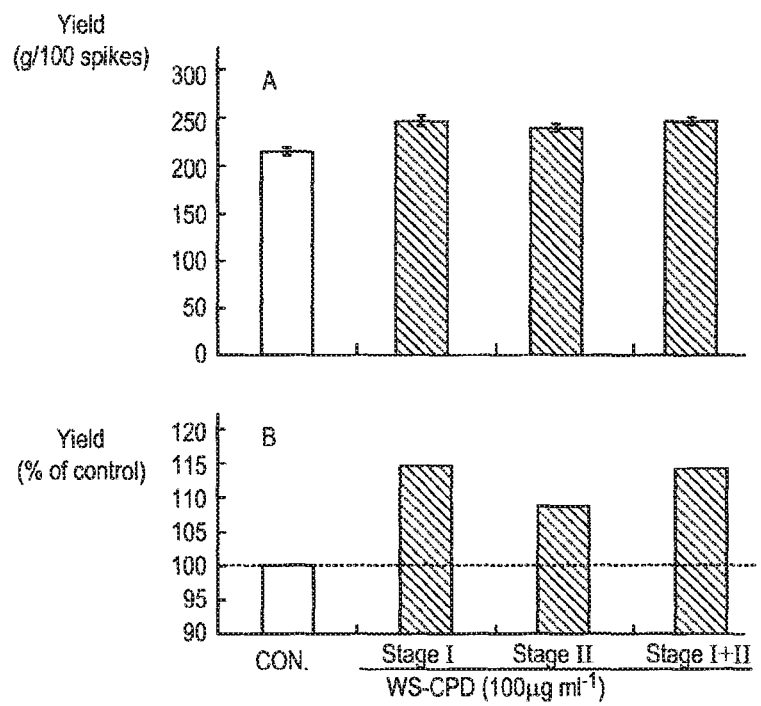
FIG. 72 Effect of WS-CPD on hand-harvested-yield (g/100 spikes)

Reference is now made to FIG. 72, presenting the effect of WS-CPD on hand-harvested-yield (g/100 spikes): (A) Yield weight per 100 spikes. (B) Yield weight per 100 spikes as percentage of control.

Figure 73:
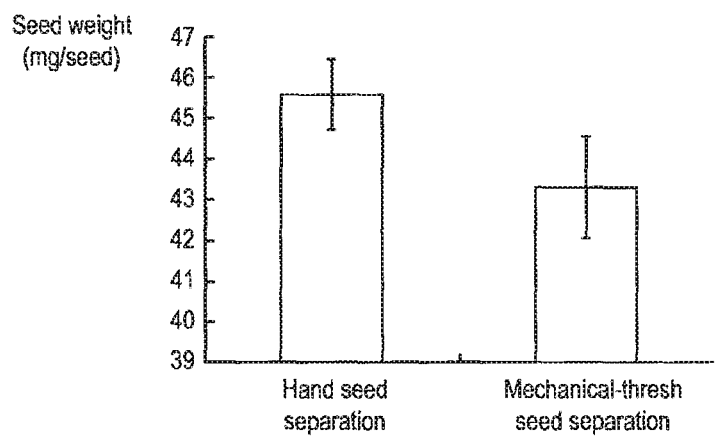
FIG. 73 Comparison of seed weight of control plants between mechanical thresh and hand-separated seeds.

Reference is now made to FIG. 73, presenting a comparison of seed weight of control plants between mechanical thresh and hand-separated seeds.

Figure 74:
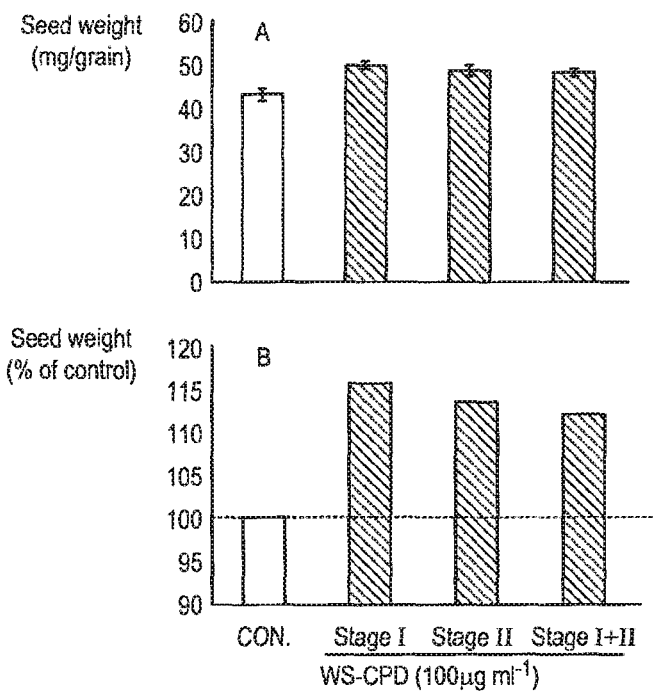
FIG. 74 Effect of WS-CPD on hand-separated seed weight (mg/seed)

Reference is now made to FIG. 74 presenting the effect of WS-CPD on hand-separated seed weight (mg/seed). (A) Seed weight (B) Seed weight as percentage of control.

Figure 75:
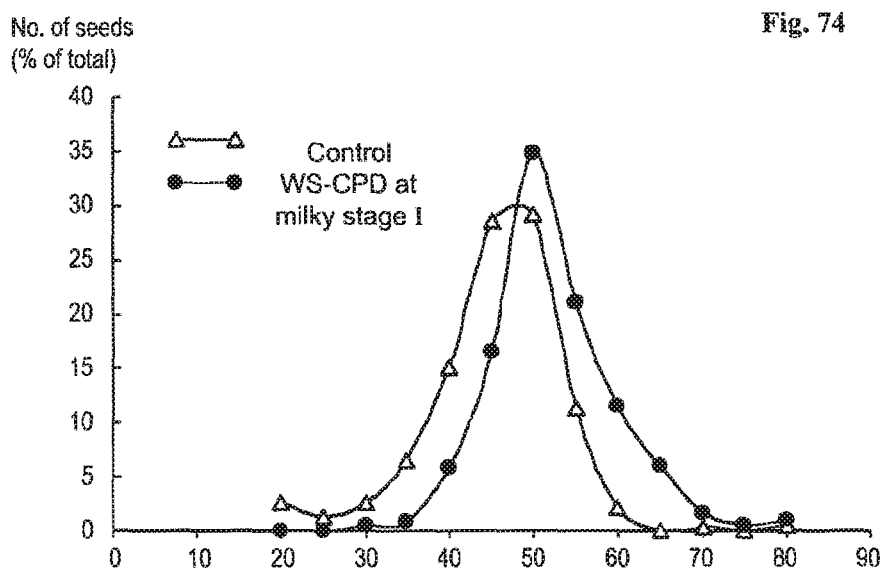
FIG. 75 Effect of WS-CPD on the distribution of seeds weight per spike, as percentage of total spikes at the 'Milky' stage I.

Reference is now made to FIG. 75 presenting the effect of WS-CPD on the distribution of seeds weight per spike, as percentage of total spikes at the 'Milky' stage I. The number of spikes with the same seed weight (mg) of 100 spikes was counted and presented as percentage of total spike number.

Figure 76:
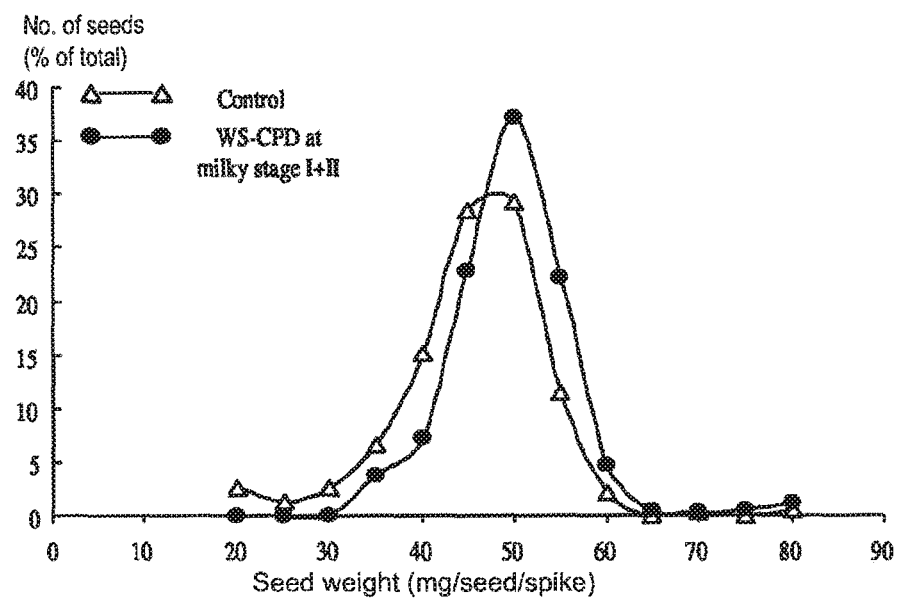
FIG. 76 Effect of WS-CPD on the distribution of seeds weight per spike, as percentage of total spikes at 'Milky' stage II; and, FIG. 77 Effect of WS-CPD on the distribution of seeds weight per spike, as percentage of total spikes at 'Milky' stages I and II.

Reference is now made to FIG. 76 presenting the effect of WS-CPD on the distribution of seeds weight per spike, as percentage of total spikes at 'Milky' stage II. The number of spikes with the same average seed weight (mg) of 100 spikes was counted and presented as percentage of total spike number.

Figure 77:
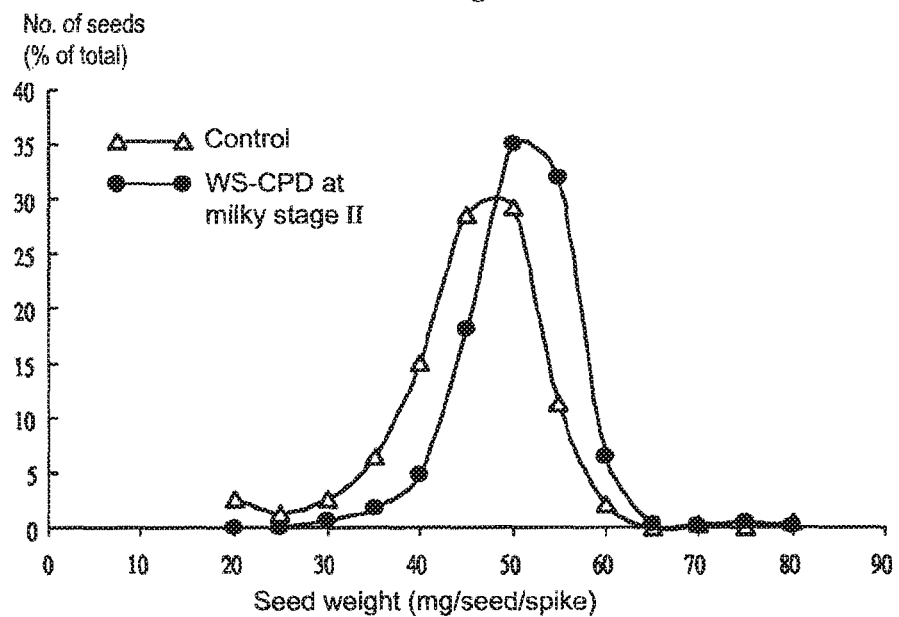

Reference is lastly made to FIG. 77 presenting the effect of WS-CPD on the distribution of seeds weight per spike, as percentage of total spikes at 'Milky' stages I and II. The number of spikes with the same average seed weight (mg) of 100 spikes was counted and presented as percentage of total spike number.

Effect of WS-CPD on Yield—This effect of WS-CPD was studied by two ways: a) calculating the yield of each experimental plot (g/plot) and; b) calculating the yield dry weight of 100 spikes randomly selected in each experimental plot (g/100 spikes). The data show:

In spite of the relatively high variability (SE about ±10%) of the number of spikes (360 to 450 spikes/plot), between the plots that were sprayed with WS-CPD at 'Milky' stage I or II (FIG. 71A), the seed yield (FIG. 71B), which was mechanically thresh separated from the spikes, increased by about 5% and 8%, respectively, compared to the untreated control (FIG. 71C). Spraying twice with WS-CPD at the 'Milky' stages I+II, had no advantage over spraying once in each of the two 'Milky' stages;

When recording the yield of 100 hand-separated spikes of each treatment (FIG. 72A), it was found that spraying WS-CPD at 'Milky' stage I significantly increased the yield over the control by about 15±2.6% (FIG. 72B, g/100 spikes), while spraying at 'Milky' stage II increased the yield by only about 8%. Spraying twice, at the 'Milky' stages I+II, had no advantage over one spray applied at the 'Milky' stage I (FIGS. 72A and B). The above data show that the increase in yield in WS-CPD-treated plants was lower than in mechanically thresh-separated seeds compared to hand-separated seeds. The different results were due to the loss of small seeds that were blown up by the strong wind of the mechanical thresh separation machine. This conclusion is based on the higher average seed weight mechanical thresh-separated seeds compared to hand-separated seeds (FIG. 73).

The increase in yield in WS-CPD-treated plants resulted from the increase in the average seed weight (FIG. 74A). One spray at the 'Milky' stage I increased the seed weight by about 15% (FIG. 74B). A later spraying at the 'Milky' stage II and two sprays gave similar results. It is evident that either when the yield was calculated as weight per 100 spikes (FIG. 72A), or on the basis of average weight (FIG. 74A), two sprays at the 'Milky' stages I+II did not show any advantage over one spray at 'Milky stage I.

Distribution of seed weight at maturity—In order to further evaluate the effect of WS-CPD on the increase in yield, the distribution of seed number in relation to their weight was calculated for the treatment applied at the 'Milky' stage I (FIG. 75) 'Milky' stage II (FIG. 76), and at both stages (FIG. 77). The distribution curves represent the effect of WS-CPD on the number of seed of a certain weight as percentage from total spikes tested. All the seeds of the treated plants were heavier than those of the control plants, irrespective of their number in each weighing group. In other words, from the lower weight of the seed groups to the highest weight seed groups, the seeds from spikes that were sprayed with WS-CPD were always significantly heavier than those from controls spikes (FIGS. 73 and 74). Again, it is obvious that the results of spraying twice were very similar to those obtained either after the first or the second spray (FIG. 77).

What is claimed is:

1. A method of inhibiting an ethylene response in a field crop, the method comprising applying to at least one portion of at least one plant of said field crop an amount of an aqueous solution of a water soluble salt of 3-(1-cyclopropenyl-propanoic acid having a formula

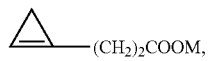—(CH$_2$)$_2$COOM, effective to produce inhibition of an ethylene response in said at least one plant,
wherein M is Na,
and wherein said inhibition of an ethylene response is manifested by a difference chosen from the group consisting of (a) increase in the yield; (b) decrease in the rate of petiole abscission; (c) decrease in the rate of leaf chlorophyll content degradation; (d) delay in the senescence of the flag leaf; (e) delay in the senescence of the green organs of the spike and ears; and (f) any combination of the above,
said difference being measured relative to an untreated plant in which said ethylene response is not inhibited.

2. The method according to claim 1, wherein said applying said solution is selected from the group consisting of (a) contacting said at least one plant with said solution; (b) dipping said at least part of said at least one plant in said solution; (c) spraying at least part of said at least one plant with said solution; (d) irrigating said at least one plant with said solution; (e) brushing at least part of said at least one plant with said solution; and (f) any combination of the above.

3. The method according to claim 1, wherein said ethylene response is selected from the group consisting of senescence, plant petiole abscission, and chlorophyll degradation.

4. The method according to claim 1, wherein said field crop is selected from the group consisting of cereals, legumes, oil-producing plants, fiber-producing plants, and tobacco.

5. The method according to claim 4, wherein said cereal is chosen from the group consisting of wheat, barley, rice, maize (corn), and oats.

6. The method according to claim 4, wherein said legume is chosen from the group consisting of soybeans, peas, peanuts, and beans.

7. The method according to claim 4, wherein said oil-producing plant is chosen from the group consisting of sunflower, safflower, castor plant, flax, sesame, perilla, and rape.

8. The method according to claim 4, wherein said fiber-producing plant is chosen from the group consisting of cotton and hemp.

9. The method of claim 1, further comprising adding to said solution an amount of a surfactant such that a surface-active aqueous solution containing said sodium salt of 3-(1-cyclopropenyl) propanoic acid is obtained.

* * * * *